(12) United States Patent
Whitman et al.

(10) Patent No.: US 8,056,786 B2
(45) Date of Patent: Nov. 15, 2011

(54) SURGICAL DEVICE

(75) Inventors: Michael P. Whitman, New Hope, PA (US); John E. Burbank, Ridgefield, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/780,197

(22) Filed: May 14, 2010

(65) Prior Publication Data

US 2010/0219227 A1    Sep. 2, 2010

Related U.S. Application Data

(63) Continuation of application No. 10/460,291, filed on Jun. 11, 2003, now Pat. No. 7,743,960.

(60) Provisional application No. 60/388,644, filed on Jun. 14, 2002.

(51) Int. Cl.
  *A61B 17/72* (2006.01)
(52) U.S. Cl. ................. 227/175.1; 227/19; 606/219
(58) Field of Classification Search .... 227/175.1–182.1, 227/19; 606/219
  See application file for complete search history.

(56) References Cited

U.S. PATENT DOCUMENTS

| | | |
|---|---|---|
| 1,881,706 A | 2/1931 | Larsen |
| 1,798,902 A | 3/1931 | Raney |
| 1,881,250 A | 10/1932 | Tomlinson |
| 2,031,682 A | 2/1936 | Wappler et al. |
| 2,226,789 A | 11/1938 | Tupy |
| 2,229,800 A | 3/1939 | Dean |

(Continued)

FOREIGN PATENT DOCUMENTS

DE   2330182   1/1975

(Continued)

OTHER PUBLICATIONS

New York Magazine, Jun. 10, 2002 The Best Doctors in New York, p. 80.

*Primary Examiner* — Lindsay Low

(57) ABSTRACT

A surgical device that includes a first jaw having a distal end and a second jaw having a distal end. The second jaw is disposed in opposed correspondence with the first jaw. The first jaw is pivotably coupled to the second jaw. The surgical device also includes a biasing element, such as a spring, that biases the distal end of the first jaw towards the distal end of the second jaw. The device may also include a first driver disposed in the second jaw and coupled to the first jaw. The first driver is configured to cause separation of the first jaw and the second jaw when the first driver is actuated for opening the jaws and to close the first jaw and the second jaw when the first driver is actuated for closing the jaws. The device may also include at least one of a cutting element and a stapling element disposed within the second jaw, preferably a blade rotatably mounted on a wedge. A second driver is configured to move the cutting element and/or the stapling element proximally from a distal end toward the proximal end of the second jaw to at least one of cut and staple a section of tissue disposed between the first and second jaws. By biasing the distal ends of the first and second jaws towards each other, the surgical device may prevent a section of tissue which is disposed between the first and second jaws from escaping out from between the distal ends of the first and second jaws.

22 Claims, 28 Drawing Sheets

U.S. PATENT DOCUMENTS

| | | |
|---|---|---|
| 2,174,219 A | 9/1939 | Balma |
| 2,246,647 A | 6/1941 | Vancura |
| 2,355,086 A | 10/1943 | Lang |
| 2,419,045 A | 4/1947 | Whittaker |
| 2,725,628 A | 12/1955 | O'Neilly et al. |
| 3,017,637 A | 7/1959 | Sampson |
| 3,079,606 A | 3/1963 | Bobrov et al. |
| 3,120,845 A | 2/1964 | Horner |
| 3,193,165 A | 7/1965 | Akhalaya et al. |
| 3,252,643 A | 5/1966 | Strekopytov et al. |
| 3,252,880 A | 5/1966 | Magat |
| 3,253,643 A | 5/1966 | Gudheim |
| 3,256,875 A | 6/1966 | Tsepelev et al. |
| 3,269,631 A | 8/1966 | Takaro |
| 3,275,211 A | 9/1966 | Hirsch et al. |
| 3,315,863 A | 4/1967 | O'Dea |
| 3,317,105 A | 5/1967 | Astafiev et al. |
| 3,388,847 A | 6/1968 | Kasulin et al. |
| 3,490,576 A | 1/1970 | Alessi et al. |
| 3,490,675 A | 1/1970 | Green et al. |
| 3,494,533 A | 2/1970 | Green et al. |
| 3,499,591 A | 3/1970 | Green |
| 3,552,626 A | 1/1971 | Astafiev et al. |
| 3,568,659 A | 3/1971 | Karnegis |
| 3,589,589 A | 6/1971 | Akopov |
| 3,593,903 A | 7/1971 | Astafiev et al. |
| 3,618,842 A | 11/1971 | Bryan |
| 3,638,652 A | 2/1972 | Kelley |
| 3,643,851 A | 2/1972 | Green |
| 3,662,939 A | 5/1972 | Bryan |
| 3,675,688 A | 7/1972 | Bryan et al. |
| 3,692,224 A | 9/1972 | Astafiev et al. |
| 3,717,294 A | 2/1973 | Green |
| 3,735,762 A | 5/1973 | Bryan et al. |
| 3,777,538 A | 12/1973 | Weatherly et al. |
| 3,788,303 A | 1/1974 | Hall |
| 3,795,034 A | 3/1974 | Strekopytov et al. |
| 3,815,476 A | 6/1974 | Green et al. |
| 3,819,100 A | 6/1974 | Noiles et al. |
| 3,837,555 A | 9/1974 | Green |
| 3,844,289 A | 10/1974 | Noiles |
| 3,858,577 A | 1/1975 | Bass et al. |
| 3,859,986 A | 1/1975 | Okada et al. |
| 3,879,104 A | 4/1975 | Shugarman et al. |
| 3,882,854 A | 5/1975 | Hulka et al. |
| 3,892,228 A | 7/1975 | Mitsui |
| 3,902,614 A | 9/1975 | Roberts et al. |
| 3,935,981 A | 2/1976 | Akopov et al. |
| 3,949,924 A | 4/1976 | Green |
| 3,952,748 A | 4/1976 | Kaliher et al. |
| RE28,932 E | 8/1976 | Noiles et al. |
| 3,985,050 A | 10/1976 | Lurie |
| 4,014,492 A | 3/1977 | Rothfuss |
| 4,027,510 A | 6/1977 | Hiltebrandt |
| 4,060,089 A | 11/1977 | Noiles |
| 4,064,881 A | 12/1977 | Meredith |
| 4,071,029 A | 1/1978 | Richmond et al. |
| 4,085,756 A | 4/1978 | Weaver |
| 4,086,926 A | 5/1978 | Green et al. |
| 4,092,986 A | 6/1978 | Schneiderman |
| 4,111,206 A | 9/1978 | Vishnevsky et al. |
| 4,169,476 A | 10/1979 | Hiltebrandt |
| 4,198,960 A | 4/1980 | Utsugi |
| 4,198,982 A | 4/1980 | Fortner et al. |
| 4,202,479 A | 5/1980 | Razgulov et al. |
| 4,202,480 A | 5/1980 | Annett |
| 4,207,873 A | 6/1980 | Kruy |
| 4,207,898 A | 6/1980 | Becht |
| 4,244,372 A | 1/1981 | Kapitanov et al. |
| 4,261,244 A | 4/1981 | Becht et al. |
| 4,273,111 A | 6/1981 | Tsukaya |
| 4,273,129 A | 6/1981 | Boebel |
| 4,286,585 A | 9/1981 | Ogawa |
| 4,289,131 A | 9/1981 | Mueller |
| 4,289,133 A | 9/1981 | Rothfuss |
| 4,296,881 A | 10/1981 | Lee |
| 4,304,236 A | 12/1981 | Conta et al. |
| 4,310,115 A | 1/1982 | Inoue |
| 4,319,576 A | 3/1982 | Rothfuss |
| 4,325,377 A | 4/1982 | Boebel |
| 4,334,539 A | 6/1982 | Childs et al. |
| 4,349,028 A | 9/1982 | Green |
| 4,351,466 A | 9/1982 | Noiles |
| 4,354,628 A | 10/1982 | Green |
| 4,360,110 A | 11/1982 | Sigman et al. |
| 4,367,729 A | 1/1983 | Ogiu |
| 4,379,457 A | 4/1983 | Gravener et al. |
| 4,383,634 A | 5/1983 | Green |
| 4,391,401 A | 7/1983 | Moshofsky |
| 4,402,311 A | 9/1983 | Hattori |
| 4,402,445 A | 9/1983 | Green |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,461,305 A | 7/1984 | Cibley |
| 4,473,077 A | 9/1984 | Noiles et al. |
| 4,476,863 A | 10/1984 | Kanshin et al. |
| 4,484,775 A | 11/1984 | Norkus |
| 4,485,817 A | 12/1984 | Swiggett |
| 4,487,270 A | 12/1984 | Huber |
| 4,488,523 A | 12/1984 | Shichman |
| 4,489,724 A | 12/1984 | Amegger |
| 4,489,875 A | 12/1984 | Crawford et al. |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,506,670 A | 3/1985 | Crossley |
| 4,506,671 A | 3/1985 | Green |
| 4,513,746 A | 4/1985 | Aranyi et al. |
| 4,519,532 A | 5/1985 | Foslien |
| 4,520,817 A | 6/1985 | Green |
| 4,534,352 A | 8/1985 | Korthoff |
| 4,534,420 A | 8/1985 | Goldelius |
| 4,535,773 A | 8/1985 | Yoon |
| 4,559,928 A | 12/1985 | Takayama |
| 4,566,620 A | 1/1986 | Green et al. |
| 4,573,468 A | 3/1986 | Conta et al. |
| 4,573,622 A | 3/1986 | Green et al. |
| 4,573,727 A | 3/1986 | Iikura |
| 4,574,806 A | 3/1986 | McCarthy |
| 4,576,167 A | 3/1986 | Noiles |
| 4,589,412 A | 5/1986 | Kensey |
| 4,589,416 A | 5/1986 | Green |
| 4,589,582 A | 5/1986 | Bilotti |
| 4,591,085 A | 5/1986 | Di Giovanni |
| 4,592,354 A | 6/1986 | Rothfuss |
| 4,593,679 A | 6/1986 | Collins |
| 4,600,357 A | 7/1986 | Coules |
| 4,603,693 A | 8/1986 | Conta et al. |
| 4,605,001 A | 8/1986 | Rothfuss et al. |
| 4,606,343 A | 8/1986 | Conta et al. |
| 4,607,638 A | 8/1986 | Crainich |
| 4,610,383 A | 9/1986 | Rothfuss et al. |
| D286,567 S | 11/1986 | Lichtman et al. |
| 4,623,183 A | 11/1986 | Aomori |
| 4,631,052 A | 12/1986 | Kensey |
| 4,633,861 A | 1/1987 | Chow et al. |
| 4,633,874 A | 1/1987 | Chow et al. |
| 4,643,190 A | 2/1987 | Heimberger |
| 4,644,952 A | 2/1987 | Patipa et al. |
| 4,646,745 A | 3/1987 | Noiles |
| 4,655,673 A | 4/1987 | Hawkes |
| 4,657,017 A | 4/1987 | Sorochenko |
| 4,664,305 A | 5/1987 | Blake, III et al. |
| 4,667,673 A | 5/1987 | Li |
| 4,669,471 A | 6/1987 | Hayashi |
| 4,671,445 A | 6/1987 | Barker et al. |
| 4,672,961 A | 6/1987 | Davies |
| 4,674,515 A | 6/1987 | Andou et al. |
| 4,676,542 A | 6/1987 | Besold |
| 4,688,555 A | 8/1987 | Wardle |
| 4,696,667 A | 9/1987 | Masch |
| 4,700,703 A | 10/1987 | Resnick et al. |

| Patent | | Date | Inventor |
|---|---|---|---|
| 4,703,887 | A | 11/1987 | Clanton et al. |
| 4,705,038 | A | 11/1987 | Sjostrom et al. |
| 4,708,141 | A | 11/1987 | Inoue et al. |
| 4,714,187 | A | 12/1987 | Green |
| 4,715,502 | A | 12/1987 | Salmon |
| 4,728,020 | A | 3/1988 | Green et al. |
| 4,732,156 | A | 3/1988 | Nakamura |
| 4,733,118 | A | 3/1988 | Mihalko |
| 4,742,815 | A | 5/1988 | Ninan et al. |
| 4,752,024 | A | 6/1988 | Green et al. |
| 4,754,909 | A | 7/1988 | Barker et al. |
| 4,756,309 | A | 7/1988 | Sachse et al. |
| 4,760,840 | A | 8/1988 | Fournier, Jr. et al. |
| 4,763,669 | A | 8/1988 | Jaeger |
| 4,767,044 | A | 8/1988 | Green |
| 4,771,774 | A | 9/1988 | Simpson et al. |
| 4,776,506 | A | 10/1988 | Green |
| 4,781,186 | A | 11/1988 | Simpson et al. |
| 4,784,137 | A | 11/1988 | Kulik et al. |
| 4,784,422 | A | 11/1988 | Jones et al. |
| 4,789,090 | A | 12/1988 | Blake, III |
| 4,796,793 | A | 1/1989 | Smith et al. |
| 4,805,823 | A | 2/1989 | Rothfuss |
| 4,815,469 | A | 3/1989 | Cohen et al. |
| 4,817,847 | A | 4/1989 | Redtenbacher et al. |
| 4,819,632 | A | 4/1989 | Davies |
| 4,819,853 | A | 4/1989 | Green |
| 4,841,888 | A | 6/1989 | Mills et al. |
| 4,848,637 | A | 7/1989 | Pruitt |
| 4,858,608 | A | 8/1989 | McQuilkin |
| 4,863,088 | A | 9/1989 | Redmond et al. |
| 4,867,158 | A | 9/1989 | Sugg |
| 4,869,415 | A | 9/1989 | Fox |
| 4,873,977 | A | 10/1989 | Avant et al. |
| 4,887,599 | A | 12/1989 | Muller |
| 4,887,612 | A | 12/1989 | Esser et al. |
| 4,890,602 | A | 1/1990 | Hake |
| 4,892,244 | A | 1/1990 | Fox et al. |
| 4,893,613 | A | 1/1990 | Hake |
| 4,893,622 | A | 1/1990 | Green et al. |
| 4,903,697 | A | 2/1990 | Resnick et al. |
| 4,907,591 | A | 3/1990 | Vasconcellos et al. |
| 4,917,114 | A | 4/1990 | Green et al. |
| 4,919,152 | A | 4/1990 | Ger |
| 4,928,699 | A | 5/1990 | Sasai |
| 4,930,494 | A | 6/1990 | Takehana et al. |
| 4,932,960 | A | 6/1990 | Green et al. |
| 4,936,845 | A | 6/1990 | Stevens |
| 4,941,454 | A | 7/1990 | Wood et al. |
| 4,941,623 | A | 7/1990 | Pruitt |
| 4,944,093 | A | 7/1990 | Falk |
| 4,944,443 | A | 7/1990 | Oddsen et al. |
| 4,955,882 | A | 9/1990 | Hakky |
| 4,955,959 | A | 9/1990 | Tompkins et al. |
| 4,957,499 | A | 9/1990 | Lipatov et al. |
| 4,962,877 | A | 10/1990 | Hervas |
| 4,976,688 | A | 12/1990 | Rosenblum |
| 4,976,710 | A | 12/1990 | Mackin |
| 4,977,900 | A | 12/1990 | Fehling et al. |
| 4,978,049 | A | 12/1990 | Green |
| 4,982,726 | A | 1/1991 | Taira |
| 4,991,764 | A | 2/1991 | Mericle |
| 4,994,060 | A | 2/1991 | Rink et al. |
| 4,995,877 | A | 2/1991 | Ams et al. |
| 5,005,749 | A | 4/1991 | Aranyi |
| 5,018,657 | A | 5/1991 | Pedlick et al. |
| 5,031,814 | A | 7/1991 | Tompkins et al. |
| 5,040,715 | A | 8/1991 | Green et al. |
| 5,059,203 | A | 10/1991 | Husted |
| 5,065,929 | A | 11/1991 | Schulze et al. |
| D322,143 | S | 12/1991 | Spreckelmeier |
| 5,071,430 | A | 12/1991 | de Salis et al. |
| 5,077,506 | A | 12/1991 | Krause |
| 5,100,041 | A | 3/1992 | Storace |
| 5,104,025 | A | 4/1992 | Main et al. |
| 5,108,391 | A | 4/1992 | Flachenecker et al. |
| 5,114,065 | A | 5/1992 | Storace |
| 5,119,983 | A | 6/1992 | Green et al. |
| 5,129,570 | A | 7/1992 | Schulze et al. |
| 5,133,359 | A | 7/1992 | Kedem |
| 5,133,713 | A | 7/1992 | Huang et al. |
| 5,139,513 | A | 8/1992 | Segato |
| 5,156,315 | A | 10/1992 | Green et al. |
| 5,157,837 | A | 10/1992 | Rose |
| 5,158,222 | A | 10/1992 | Green |
| 5,170,925 | A * | 12/1992 | Madden et al. ............ 227/175.1 |
| 5,171,247 | A | 12/1992 | Hughett et al. |
| 5,171,251 | A | 12/1992 | Bregen et al. |
| 5,173,133 | A | 12/1992 | Morin et al. |
| 5,192,292 | A | 3/1993 | Cezana et al. |
| 5,197,649 | A | 3/1993 | Bessler et al. |
| 5,201,325 | A | 4/1993 | McEwen et al. |
| 5,201,501 | A | 4/1993 | Fassler |
| 5,201,750 | A | 4/1993 | Hocherl et al. |
| 5,205,459 | A | 4/1993 | Brinkerhoff et al. |
| 5,207,691 | A | 5/1993 | Nardella |
| 5,207,697 | A | 5/1993 | Carusillo et al. |
| 5,217,003 | A | 6/1993 | Wilk |
| 5,217,460 | A | 6/1993 | Knoepfler |
| 5,221,279 | A | 6/1993 | Cook et al. |
| 5,224,951 | A | 7/1993 | Freitas |
| 5,226,426 | A | 7/1993 | Yoon |
| 5,237,884 | A | 8/1993 | Seto |
| 5,243,967 | A | 9/1993 | Hibino |
| 5,249,583 | A | 10/1993 | Mallaby |
| 5,253,793 | A | 10/1993 | Green |
| 5,254,117 | A | 10/1993 | Rigby et al. |
| 5,258,004 | A | 11/1993 | Bales et al. |
| 5,258,007 | A | 11/1993 | Spetzler et al. |
| 5,258,008 | A | 11/1993 | Wilk |
| 5,261,877 | A | 11/1993 | Fine et al. |
| 5,267,997 | A | 12/1993 | Farin et al. |
| 5,268,622 | A | 12/1993 | Philipp |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,609 | A | 1/1994 | Pingleton et al. |
| 5,279,565 | A | 1/1994 | Klein et al. |
| 5,285,945 | A | 2/1994 | Brinkerhoff et al. |
| 5,289,963 | A | 3/1994 | McGarry et al. |
| 5,290,299 | A | 3/1994 | Fain et al. |
| 5,290,303 | A | 3/1994 | Pingleton et al. |
| 5,292,053 | A | 3/1994 | Bilotti et al. |
| 5,295,990 | A | 3/1994 | Levin |
| 5,300,087 | A | 4/1994 | Knoepfler |
| 5,307,976 | A | 5/1994 | Olson et al. |
| 5,312,023 | A | 5/1994 | Green et al. |
| 5,312,434 | A | 5/1994 | Crainich |
| 5,318,221 | A | 6/1994 | Green et al. |
| 5,320,627 | A | 6/1994 | Sorensen et al. |
| 5,322,055 | A | 6/1994 | Davison et al. |
| 5,324,288 | A | 6/1994 | Billings et al. |
| 5,324,300 | A | 6/1994 | Elias et al. |
| 5,326,013 | A | 7/1994 | Green et al. |
| 5,330,471 | A | 7/1994 | Eggers |
| 5,330,486 | A | 7/1994 | Wilk |
| 5,333,772 | A | 8/1994 | Rothfuss et al. |
| 5,333,773 | A | 8/1994 | Main et al. |
| 5,336,229 | A | 8/1994 | Noda |
| 5,342,299 | A | 8/1994 | Snoke et al. |
| 5,342,381 | A | 8/1994 | Tidemand |
| 5,342,382 | A | 8/1994 | Brinkerhoff et al. |
| 5,344,420 | A | 9/1994 | Hilal et al. |
| 5,350,104 | A | 9/1994 | Main et al. |
| 5,352,222 | A | 10/1994 | Rydell |
| 5,352,223 | A | 10/1994 | McBrayer et al. |
| 5,352,235 | A | 10/1994 | Koros et al. |
| 5,354,266 | A | 10/1994 | Snoke |
| 5,356,408 | A | 10/1994 | Rydell |
| 5,358,506 | A | 10/1994 | Green et al. |
| 5,364,001 | A | 11/1994 | Bryan |
| 5,364,409 | A | 11/1994 | Kuwabara et al. |
| 5,366,133 | A | 11/1994 | Geiste |
| 5,366,476 | A | 11/1994 | Noda |
| 5,368,015 | A | 11/1994 | Wilk |
| 5,368,607 | A | 11/1994 | Freitas |

| Patent No. | Date | Name |
|---|---|---|
| 5,370,294 A | 12/1994 | Bauer |
| 5,380,321 A | 1/1995 | Yoon |
| 5,383,880 A | 1/1995 | Hooven |
| 5,389,098 A | 2/1995 | Tsuruta et al. |
| 5,391,156 A | 2/1995 | Hildwein et al. |
| 5,392,789 A | 2/1995 | Slater et al. |
| 5,395,030 A | 3/1995 | Kuramoto et al. |
| 5,395,033 A | 3/1995 | Byrne et al. |
| 5,395,369 A | 3/1995 | McBrayer et al. |
| 5,396,900 A | 3/1995 | Slater et al. |
| 5,397,046 A | 3/1995 | Savage et al. |
| 5,400,267 A | 3/1995 | Denen et al. |
| D357,535 S | 4/1995 | Grant et al. |
| 5,403,312 A | 4/1995 | Yates et al. |
| 5,403,326 A | 4/1995 | Harrison et al. |
| 5,403,327 A | 4/1995 | Thornton et al. |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson et al. |
| 5,425,705 A | 6/1995 | Evard et al. |
| 5,425,738 A | 6/1995 | Gustafson et al. |
| 5,425,745 A | 6/1995 | Green et al. |
| 5,431,322 A | 7/1995 | Green et al. |
| 5,431,645 A | 7/1995 | Smith et al. |
| 5,433,721 A | 7/1995 | Hooven et al. |
| 5,437,636 A | 8/1995 | Snoke et al. |
| 5,437,684 A | 8/1995 | Calabrese et al. |
| 5,441,507 A | 8/1995 | Wilk |
| 5,443,198 A | 8/1995 | Viola et al. |
| 5,447,265 A | 9/1995 | Vidal et al. |
| 5,454,825 A | 10/1995 | Van Leeuwen et al. |
| 5,456,684 A | 10/1995 | Schmidt et al. |
| 5,460,182 A | 10/1995 | Goodman et al. |
| 5,464,404 A | 11/1995 | Abela et al. |
| 5,465,894 A | 11/1995 | Clark et al. |
| 5,465,895 A | 11/1995 | Knodel et al. |
| 5,467,911 A | 11/1995 | Tsuruta et al. |
| 5,472,132 A | 12/1995 | Savage et al. |
| 5,474,223 A | 12/1995 | Viola et al. |
| 5,476,206 A | 12/1995 | Green et al. |
| 5,482,054 A | 1/1996 | Slater et al. |
| 5,482,197 A | 1/1996 | Green et al. |
| 5,485,947 A | 1/1996 | Olson et al. |
| 5,487,499 A | 1/1996 | Sorrentino et al. |
| 5,487,500 A | 1/1996 | Knodel et al. |
| 5,496,269 A | 3/1996 | Snoke |
| 5,496,317 A | 3/1996 | Goble et al. |
| 5,496,333 A | 3/1996 | Sackier et al. |
| 5,514,134 A | 5/1996 | Rydell et al. |
| 5,518,163 A | 5/1996 | Hooven |
| 5,518,164 A | 5/1996 | Hooven |
| 5,520,634 A | 5/1996 | Fox et al. |
| 5,524,180 A | 6/1996 | Wang et al. |
| 5,527,313 A | 6/1996 | Scott et al. |
| 5,529,235 A | 6/1996 | Boiarski et al. |
| 5,531,687 A | 7/1996 | Snoke et al. |
| 5,533,661 A | 7/1996 | Main et al. |
| 5,535,935 A | 7/1996 | Vidal et al. |
| 5,535,937 A | 7/1996 | Boiarski et al. |
| 5,549,565 A | 8/1996 | Ryan et al. |
| 5,553,765 A | 9/1996 | Knodel et al. |
| 5,554,169 A | 9/1996 | Green et al. |
| 5,562,677 A | 10/1996 | Hildwein et al. |
| 5,562,702 A | 10/1996 | Huitema et al. |
| 5,569,274 A | 10/1996 | Rapacki et al. |
| 5,571,116 A | 11/1996 | Bolanos et al. |
| 5,573,543 A | 11/1996 | Akopov et al. |
| 5,575,799 A | 11/1996 | Bolanos et al. |
| 5,578,052 A | 11/1996 | Koros et al. |
| 5,580,067 A | 12/1996 | Hamblin et al. |
| 5,582,611 A | 12/1996 | Tsukagoshii et al. |
| 5,584,425 A | 12/1996 | Savage et al. |
| 5,588,579 A | 12/1996 | Schnut et al. |
| 5,591,186 A | 1/1997 | Wurster et al. |
| 5,591,196 A | 1/1997 | Marin et al. |
| 5,597,107 A | 1/1997 | Knodel et al. |
| 5,599,347 A | 2/1997 | Hart et al. |
| 5,603,443 A | 2/1997 | Clark et al. |
| 5,607,094 A | 3/1997 | Clark et al. |
| 5,609,285 A | 3/1997 | Grant et al. |
| 5,609,381 A | 3/1997 | Thom et al. |
| 5,609,560 A | 3/1997 | Ichikawa et al. |
| 5,618,303 A | 4/1997 | Marlow et al. |
| 5,618,307 A | 4/1997 | Donlon et al. |
| 5,626,607 A | 5/1997 | Malecki et al. |
| 5,639,008 A | 6/1997 | Gallagher et al. |
| 5,651,780 A | 7/1997 | Jackson et al. |
| 5,653,374 A | 8/1997 | Young et al. |
| 5,665,100 A | 9/1997 | Yoon |
| 5,667,473 A | 9/1997 | Finn et al. |
| 5,667,478 A | 9/1997 | McFarcin et al. |
| 5,667,517 A | 9/1997 | Hooven |
| 5,667,526 A | 9/1997 | Levin |
| 5,676,674 A | 10/1997 | Bolanos et al. |
| 5,688,269 A | 11/1997 | Newton et al. |
| 5,692,668 A | 12/1997 | Schulze et al. |
| 5,693,031 A | 12/1997 | Ryan et al. |
| 5,697,542 A | 12/1997 | Knodel et al. |
| 5,709,335 A | 1/1998 | Heck |
| 5,711,472 A | 1/1998 | Bryan |
| 5,732,871 A | 3/1998 | Clark et al. |
| 5,732,872 A | 3/1998 | Bolduc et al. |
| 5,735,848 A | 4/1998 | Yates et al. |
| 5,735,849 A | 4/1998 | Baden et al. |
| 5,735,861 A | 4/1998 | Peifer et al. |
| 5,741,285 A | 4/1998 | McBrayer et al. |
| 5,749,885 A | 5/1998 | Sjostrom et al. |
| 5,749,893 A | 5/1998 | Vidal et al. |
| 5,752,644 A | 5/1998 | Bolanos et al. |
| 5,758,814 A | 6/1998 | Gallagher et al. |
| 5,762,458 A | 6/1998 | Wang et al. |
| 5,776,147 A | 7/1998 | Dolendo |
| 5,779,130 A | 7/1998 | Alesi et al. |
| 5,779,132 A | 7/1998 | Knodel et al. |
| 5,782,396 A | 7/1998 | Mastri et al. |
| 5,782,397 A | 7/1998 | Koukline |
| 5,792,135 A | 8/1998 | Madhani et al. |
| 5,797,835 A | 8/1998 | Green |
| 5,797,900 A | 8/1998 | Madhani et al. |
| 5,797,944 A | 8/1998 | Nobles et al. |
| 5,807,377 A | 9/1998 | Madhani et al. |
| 5,807,402 A | 9/1998 | Yoon |
| 5,814,044 A | 9/1998 | Hooven |
| 5,815,640 A | 9/1998 | Wang et al. |
| 5,817,113 A | 10/1998 | Gifford, III et al. |
| 5,823,956 A | 10/1998 | Roth et al. |
| 5,826,776 A | 10/1998 | Schulze et al. |
| 5,829,662 A | 11/1998 | Allen et al. |
| 5,836,503 A | 11/1998 | Ehrenfels et al. |
| 5,846,221 A | 12/1998 | Snoke et al. |
| 5,855,583 A | 1/1999 | Wang et al. |
| 5,855,590 A | 1/1999 | Malecki et al. |
| 5,857,996 A | 1/1999 | Snoke |
| 5,860,953 A | 1/1999 | Snoke et al. |
| 5,868,760 A | 2/1999 | McGuckin, Jr. |
| 5,871,471 A | 2/1999 | Ryan et al. |
| 5,878,193 A | 3/1999 | Wang et al. |
| 5,881,943 A | 3/1999 | Heck et al. |
| 5,893,553 A | 4/1999 | Pinkous |
| 5,893,875 A | 4/1999 | O'Connor et al. |
| 5,895,084 A | 4/1999 | Mauro |
| 5,897,562 A | 4/1999 | Balanos et al. |
| 5,907,664 A | 5/1999 | Wang et al. |
| 5,913,842 A | 6/1999 | Boyd et al. |
| 5,915,616 A | 6/1999 | Viola et al. |
| 5,925,055 A | 7/1999 | Adrian et al. |
| 5,931,848 A | 8/1999 | Saadat |
| 5,947,363 A | 9/1999 | Bolduc et al. |
| 5,951,549 A | 9/1999 | Richardson et al. |
| 5,954,259 A | 9/1999 | Viola et al. |
| 5,954,731 A | 9/1999 | Yoon |
| 5,957,363 A | 9/1999 | Heck |
| 5,957,882 A | 9/1999 | Nita et al. |
| 5,957,884 A | 9/1999 | Hooven |
| 5,976,159 A | 11/1999 | Bolduc et al. |
| 5,984,919 A | 11/1999 | Hilal et al. |
| 5,989,215 A | 11/1999 | Delmotte et al. |

| | | |
|---|---|---|
| 5,993,378 A | 11/1999 | Lemelson |
| 5,993,454 A | 11/1999 | Longo |
| 5,997,510 A | 12/1999 | Schwemberger |
| 6,001,108 A | 12/1999 | Wang et al. |
| 6,004,335 A | 12/1999 | Vaitekunas et al. |
| 6,007,512 A | 12/1999 | Hooven |
| 6,007,531 A | 12/1999 | Snoke et al. |
| 6,010,054 A | 1/2000 | Johnson et al. |
| 6,010,493 A | 1/2000 | Snoke |
| 6,017,322 A | 1/2000 | Snoke et al. |
| 6,017,354 A | 1/2000 | Culp et al. |
| 6,024,741 A | 2/2000 | Williamson, IV et al. |
| 6,063,095 A | 5/2000 | Wang et al. |
| 6,068,627 A | 5/2000 | Orszulak et al. |
| 6,074,402 A | 6/2000 | Peifer et al. |
| 6,083,163 A | 7/2000 | Wegner et al. |
| 6,086,600 A | 7/2000 | Kortenbach |
| 6,090,120 A | 7/2000 | Wright et al. |
| 6,099,466 A | 8/2000 | Sano et al. |
| 6,106,512 A | 8/2000 | Cochran et al. |
| 6,110,188 A | 8/2000 | Narciso, Jr. |
| 6,119,913 A | 9/2000 | Adams et al. |
| 6,126,058 A | 10/2000 | Adams et al. |
| 6,126,591 A | 10/2000 | McGarry et al. |
| 6,132,368 A | 10/2000 | Cooper |
| 6,162,220 A | 12/2000 | Nezhat |
| 6,165,191 A | 12/2000 | Shibata et al. |
| 6,174,324 B1 | 1/2001 | Egan et al. |
| 6,179,837 B1 | 1/2001 | Hooven |
| 6,193,129 B1 | 2/2001 | Bittner et al. |
| D438,617 S | 3/2001 | Cooper et al. |
| 6,201,984 B1 | 3/2001 | Funda et al. |
| 6,206,903 B1 | 3/2001 | Ramans |
| D441,076 S | 4/2001 | Cooper et al. |
| 6,209,773 B1 | 4/2001 | Bolduc et al. |
| 6,217,591 B1 | 4/2001 | Egan et al. |
| D441,862 S | 5/2001 | Cooper et al. |
| 6,231,587 B1 | 5/2001 | Makower |
| 6,244,809 B1 | 6/2001 | Wang et al. |
| 6,246,200 B1 | 6/2001 | Blumenkranz et al. |
| 6,264,087 B1 | 7/2001 | Whitman |
| 6,309,397 B1 | 10/2001 | Julian et al. |
| 6,312,435 B1 | 11/2001 | Wallace et al. |
| 6,315,184 B1 | 11/2001 | Whitman |
| 6,331,181 B1 | 12/2001 | Tierney et al. |
| 6,346,072 B1 | 2/2002 | Cooper |
| 6,348,061 B1 | 2/2002 | Whitman |
| 6,364,888 B1 | 4/2002 | Niemeyer et al. |
| 6,368,340 B2 | 4/2002 | Malecki et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,533,157 B1 | 3/2003 | Whitman |
| 6,790,217 B2 | 9/2004 | Schulze et al. |
| 2001/0016750 A1 | 8/2001 | Malecki et al. |
| 2001/0031975 A1 | 10/2001 | Whitman et al. |
| 2002/0032451 A1 | 3/2002 | Tierney et al. |
| 2002/0032452 A1 | 3/2002 | Tierney et al. |
| 2002/0042620 A1 | 4/2002 | Julian et al. |
| 2002/0045888 A1 | 4/2002 | Ramans et al. |
| 2002/0049454 A1 | 4/2002 | Whitman et al. |
| 2002/0055795 A1 | 5/2002 | Niemeyer et al. |
| 2002/0072736 A1 | 6/2002 | Tierney et al. |
| 2002/0165444 A1 | 11/2002 | Whitman |
| 2003/0105478 A1 | 6/2003 | Whitman et al. |
| 2003/0130677 A1 | 7/2003 | Whitman et al. |

FOREIGN PATENT DOCUMENTS

| | | |
|---|---|---|
| DE | 29 03 159 | 7/1980 |
| DE | 3114135 | 10/1982 |
| DE | 33 00 768 | 7/1984 |
| DE | 42 13 426 | 10/1992 |
| DE | 4312147 | 10/1992 |
| EP | 41022 | 12/1981 |
| EP | 0 116 220 | 8/1984 |
| EP | 0 121 474 | 10/1984 |
| EP | 0 142 225 | 5/1985 |
| EP | 0 156 774 | 10/1985 |
| EP | 0 203 375 | 12/1986 |
| EP | 0 216 532 | 4/1987 |
| EP | 293123 | 1/1988 |
| EP | 324166 | 7/1989 |
| EP | 324637 | 7/1989 |
| EP | 365153 | 4/1990 |
| EP | 369324 | 5/1990 |
| EP | 373762 | 6/1990 |
| EP | 0 399 701 | 11/1990 |
| EP | 0 514 139 | 11/1992 |
| EP | 0 536 903 | 4/1993 |
| EP | 0 539 762 | 5/1993 |
| EP | 0 552 050 | 7/1993 |
| EP | 0 593 920 | 4/1994 |
| EP | 0 598 579 | 5/1994 |
| EP | 0 621 006 | 10/1994 |
| EP | 630612 | 12/1994 |
| EP | 0 634 144 | 1/1995 |
| EP | 639349 | 2/1995 |
| EP | 679367 | 11/1995 |
| EP | 0 705 571 | 4/1996 |
| EP | 552423 | 1/1998 |
| EP | 0 878 169 | 11/1998 |
| EP | 0 947 167 | 10/1999 |
| EP | 0 653 922 | 12/1999 |
| EP | 581400 | 5/2000 |
| EP | 484677 | 7/2000 |
| FR | 2660851 | 10/1991 |
| GB | 1 082 821 | 9/1967 |
| GB | 1352554 | 5/1974 |
| GB | 1452185 | 10/1976 |
| GB | 2 044 108 | 10/1980 |
| GB | 2048685 | 12/1980 |
| GB | 2165559 | 4/1986 |
| GB | 2180455 | 4/1987 |
| NL | 77 11 347 | 4/1979 |
| NL | 7711347 | 4/1979 |
| RU | 659146 | 4/1979 |
| WO | WO 82/03545 | 10/1982 |
| WO | WO 83/00992 | 3/1983 |
| WO | WO 90/05489 | 5/1990 |
| WO | WO 90/05491 | 5/1990 |
| WO | WO 9006085 | 6/1990 |
| WO | WO 91/07136 | 5/1991 |
| WO | WO 92/16141 | 10/1992 |
| WO | WO 93/08754 | 5/1993 |
| WO | WO 93/14706 | 8/1993 |
| WO | WO 95/35065 | 12/1995 |
| WO | WO 95/18572 | 7/1996 |
| WO | WO 97/12555 | 4/1997 |
| WO | WO 98/14129 | 4/1998 |
| WO | WO 99/20328 | 4/1999 |
| WO | WO 99/58076 | 11/1999 |
| WO | WO 00/72765 | 12/2000 |
| WO | WO 01/03587 | 1/2001 |
| WO | WO 01/08572 | 2/2001 |
| WO | WO 01/17448 | 3/2001 |
| WO | WO 01/35813 | 5/2001 |
| WO | WO 01/62163 | 8/2001 |
| WO | WO 02/058539 | 8/2002 |
| WO | WO 03/077769 | 9/2003 |

* cited by examiner

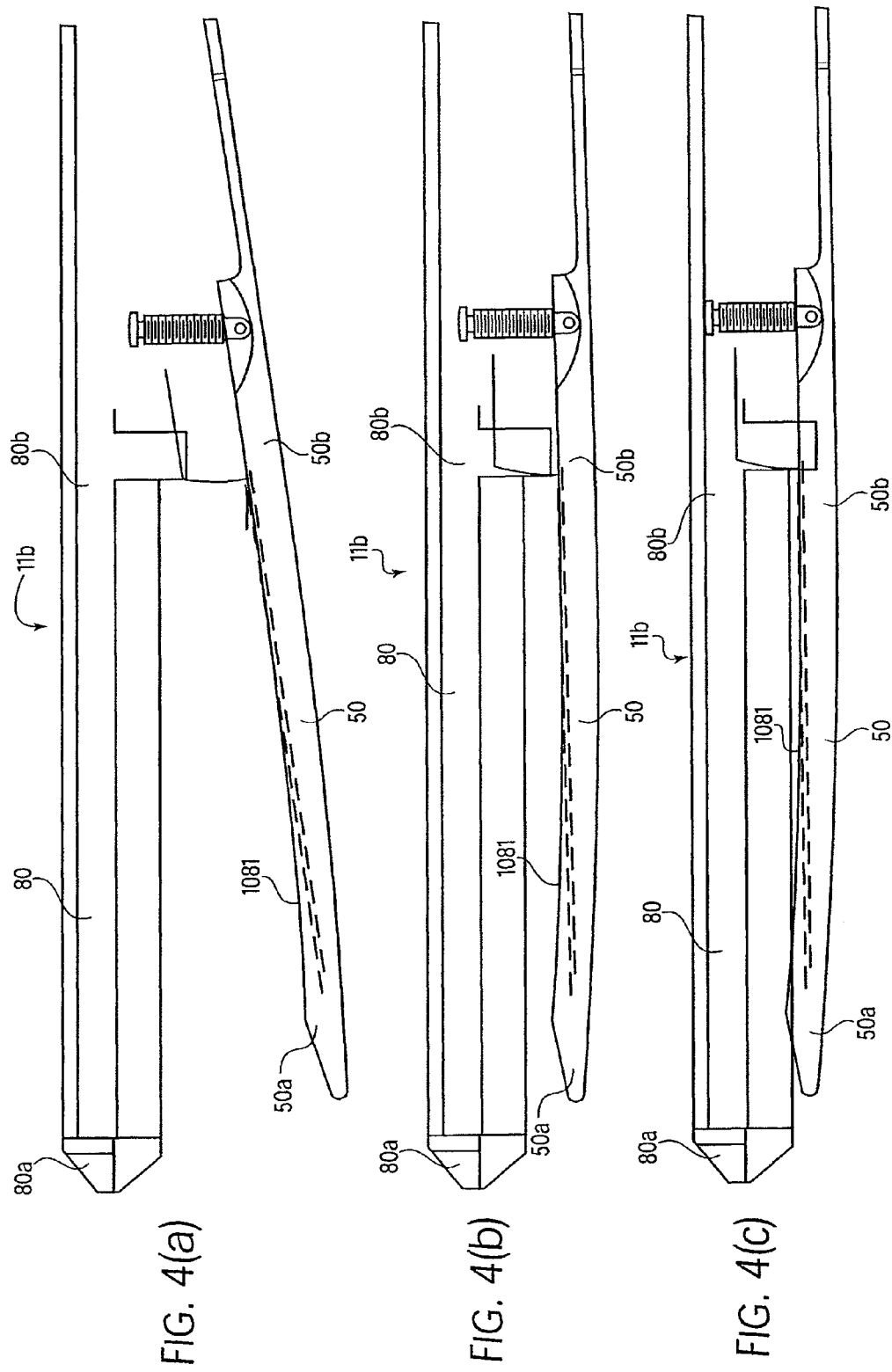

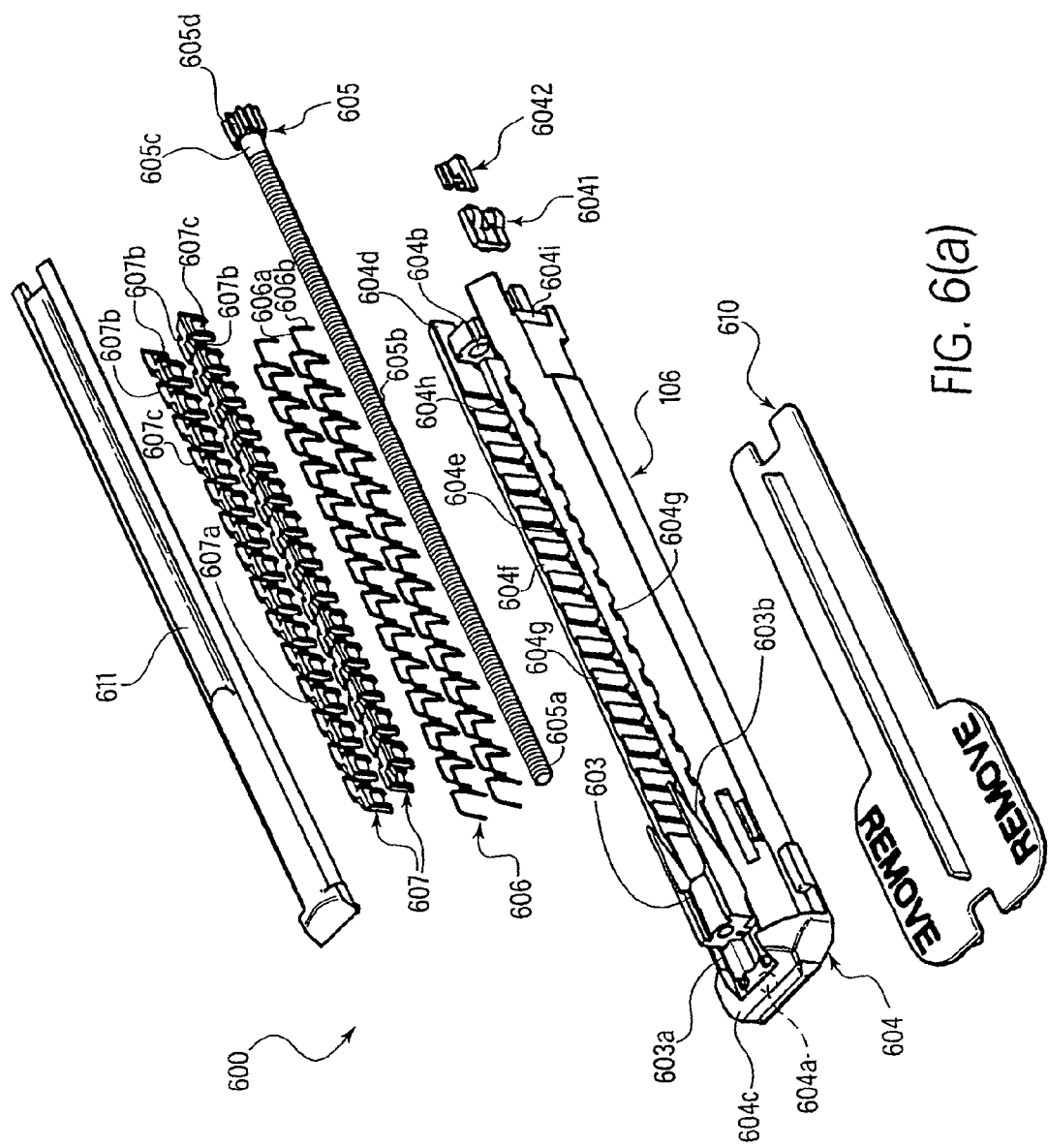

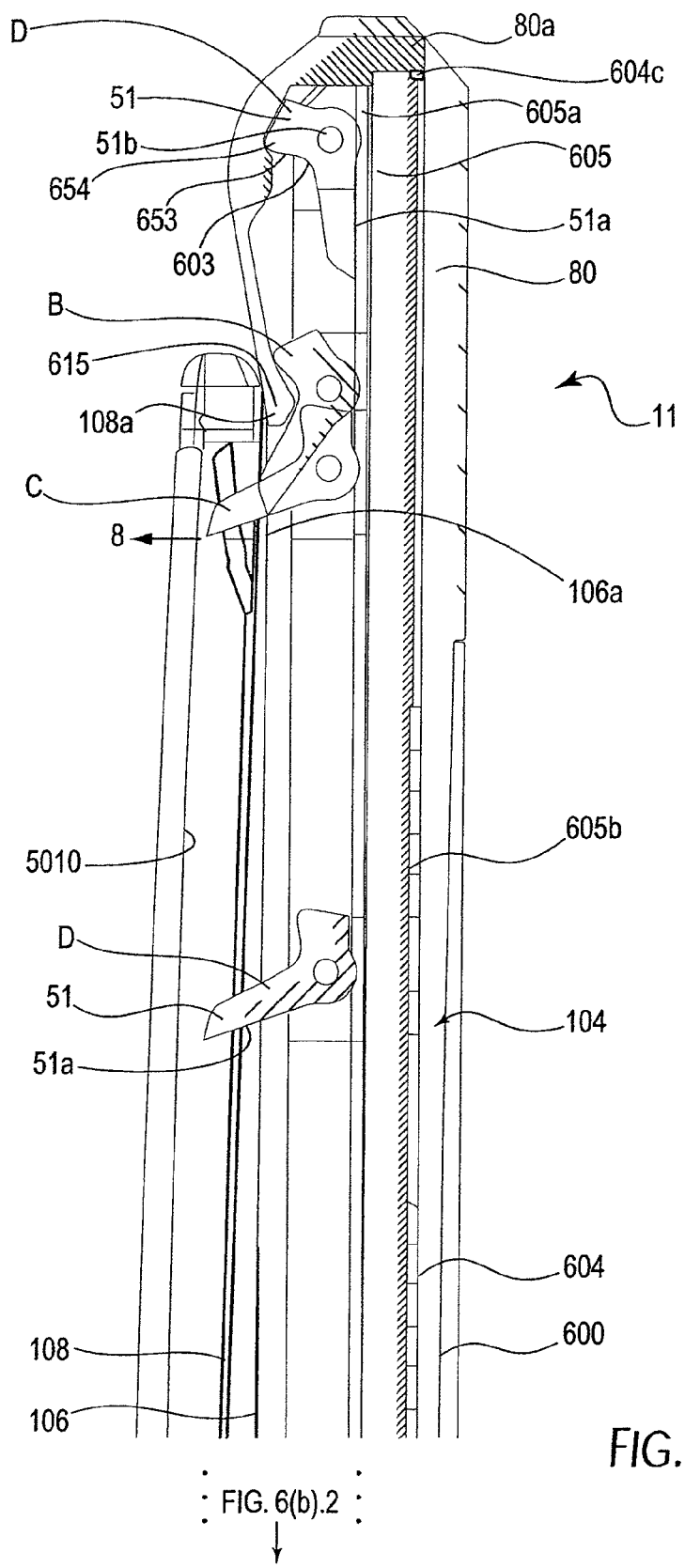
FIG. 6(b).1

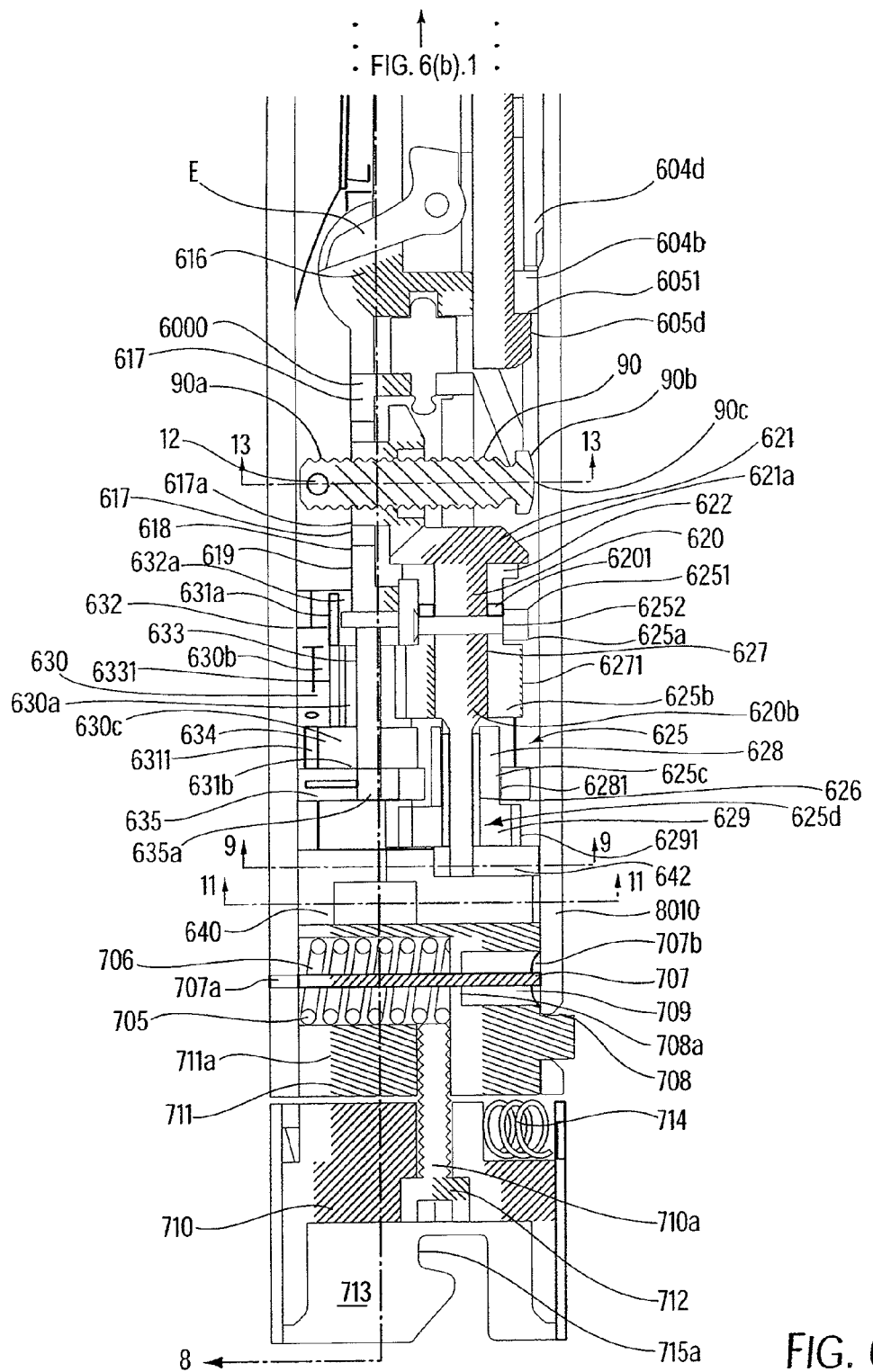
FIG. 6(b).2

SURGICAL DEVICE

CROSS-REFERENCE TO RELATED APPLICATIONS

The present application is a Continuation application which claims the benefit of and priority to U.S. patent application Ser. No. 10/460,291, filed on Jun. 11, 2003, now U.S. Pat. No. 7,743,960 which claims the benefit of and priority to U.S. provisional application Ser. No. 60/388,644, filed on Jun. 14, 2002, the entire content of each of which being incorporated herein by reference.

The present application expressly incorporates herein by reference each of the following in its entirety: U.S. patent application Ser. No. 09/999,546, filed on Nov. 30, 2001 (now U.S. Pat. No. 7,695,485); U.S. patent application Ser. No. 09/887,789, filed on Jun. 22, 2001 (now U.S. Pat. No. 7,032,798); U.S. patent application Ser. No. 09/836,781, filed on Apr. 17, 2001 (now U.S. Pat. No. 6,981,941); U.S. patent application Ser. No. 09/723,715, filed on Nov. 28, 2000 (now U.S. Pat. No. 6,793,652); U.S. patent application Ser. No. 09/324,451, filed on Jun. 2, 1999 (now U.S. Pat. No. 6,315,184); U.S. patent application Ser. No. 09/324,452, filed on Jun. 2, 1999 (now U.S. Pat. No. 6,443,973); U.S. patent application Ser. No. 09/351,534, filed on Jul. 12, 1999 (now U.S. Pat. No. 6,264,087); U.S. patent application Ser. No. 09/510,923, filed on Feb. 22, 2000 (now U.S. Pat. No. 6,517,565); and U.S. patent application Ser. No. 09/510,927, filed on Feb. 22, 2000 (now U.S. Pat. No. 6,716,233).

FIELD OF THE INVENTION

The present invention relates to a surgical device. More specifically, the present invention relates to a linear clamping, cutting and stapling device for clamping, cutting and stapling tissue.

BACKGROUND INFORMATION

One type of surgical device is a linear clamping, cutting and stapling device. Such a device may be employed in a surgical procedure to resect a cancerous or anomalous tissue from a gastro-intestinal tract. One conventional linear clamping, cutting and stapling instrument is shown in FIG. 1. The device includes a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

One problem with the foregoing surgical devices, and in particular with the foregoing linear clamping, cutting and stapling devices such as that illustrated in FIG. 1, is that the opposing jaws of the clamping mechanism do not provide adequate clamping at the distal ends of the scissors-styled gripping elements to insure that a section of tissue clamped between the gripping elements is prevented from being pushed out from between the distal ends of the gripping elements.

SUMMARY OF THE INVENTION

In accordance with one example embodiment of the present invention, a surgical device is provided that includes a first jaw having a distal end and a second jaw having a distal end. The second jaw is disposed in opposed correspondence with the first jaw. The first jaw is pivotably coupled to the second jaw. The surgical device also includes a biasing element that biases the distal end of the first jaw towards the distal end of the second jaw. The biasing element may include a spring coupling the proximal end of the first jaw and the proximal end of the second jaw.

The device may also include a first driver disposed in the second jaw and coupled to the first jaw. The first driver is configured to cause separation of the first jaw and the second jaw when the first driver is actuated for opening the jaws and to close the first jaw and the second jaw when the first driver is actuated for closing the jaws. The device may also include at least one of a cutting element and a stapling element disposed within the second jaw, preferably a blade rotatably mounted on a wedge. A second driver is configured to move the cutting element and/or the stapling element proximally from a distal end toward the proximal end of the second jaw to at least one of cut and staple a section of tissue disposed between the first and second jaws.

By biasing the distal ends of the first and second jaws towards each other, the surgical device may, in accordance with one example embodiment of the present invention, prevent a section of tissue which is disposed between the first and second jaws from escaping out from between the distal ends of the first and second jaws.

BRIEF DESCRIPTION OF THE DRAWINGS

FIGS. 4(a) to 4(c) are side views of a linear clamping, cutting and stapling attachment, at various stages of its operation, according to another example embodiment of the present invention;

FIG. 6(a) is an exploded view of a replaceable staple cartridge for use in the linear clamping, cutting and stapling attachment illustrated in FIG. 5(a);

FIG. 6(b) is a cross-sectional view of the linear clamping, cutting and stapling attachment taken along the line 6-6 shown in FIG. 5(b);

DETAILED DESCRIPTION

Figure 1:
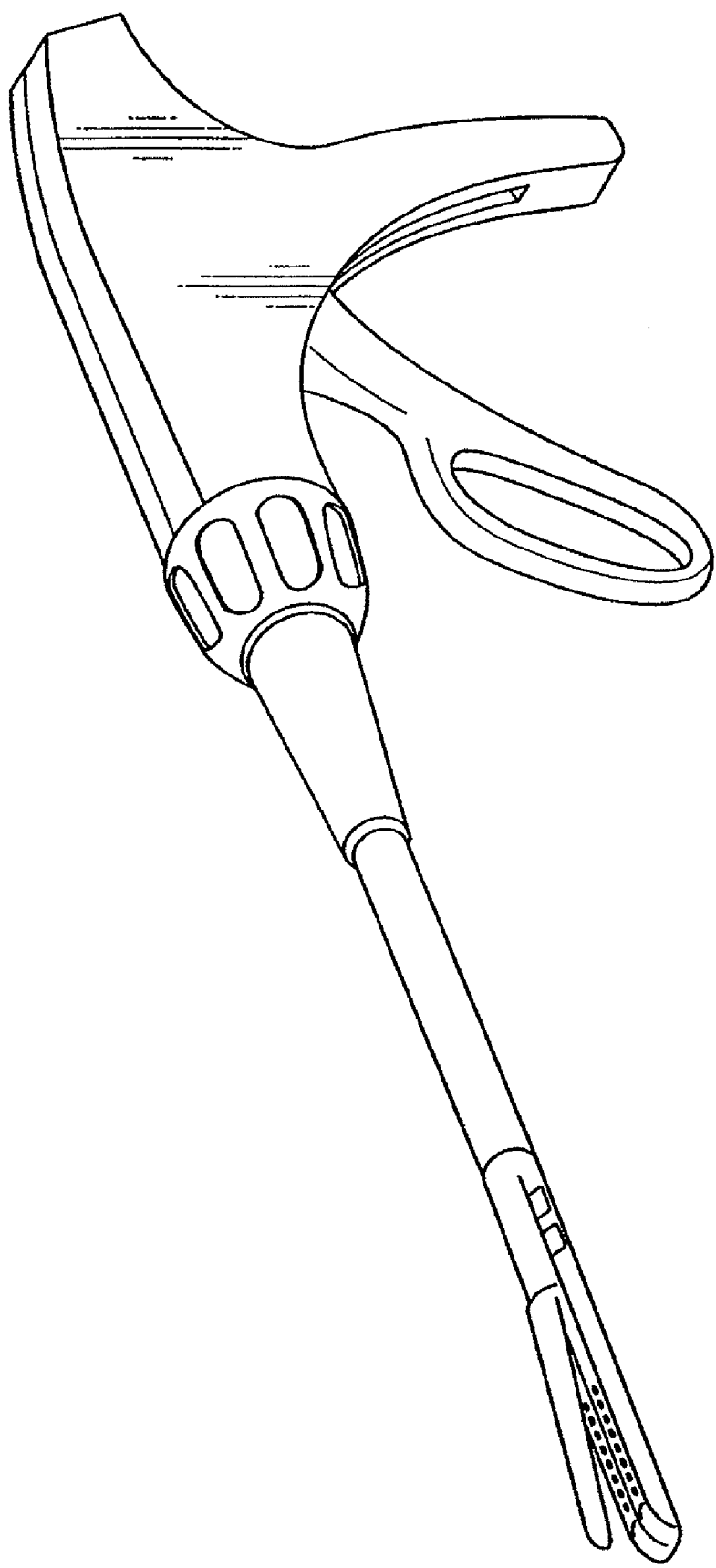
FIG. 1 is a perspective view of a conventional linear clamping, cutting and stapling device.

One example embodiment of a surgical device according to the present invention is schematically illustrated in FIGS. 3(*a*) to 3(*d*). Referring to FIGS. 3(*a*) to 3(*d*), an example embodiment of the surgical device 11*a*, e.g., a linear clamping, cutting and stapling device, is illustrated. In this embodiment, a surgical device 11*a* includes a first jaw 50 having a distal end 50*a* and a proximal end 50*b*, and a second jaw 80 having a distal end 80*a* and a proximal end 80*b*. The first jaw 50 and the second jaw 80 are pivotably coupled at or near their respective proximal ends 50*b*, 80*b*. The proximal end 50*b* of the first jaw 50 and the proximal end 80*b* of the second jaw 80 are biased away from each other via a biasing element 82. In this example embodiment, the biasing element 82 may be a spring. The surgical device 11*a* includes a stop element that limits the distance that the proximal end 50*b* of the first jaw 50 can be separated from the proximal end 80*b* of the second jaw 80. In the example embodiment of the present invention illustrated in FIGS. 3(*a*) to 3(*d*), the stop element includes a pin 84 disposed near the proximal end 80*b* of the second jaw 80 that engages a slot 86 near the proximal end 50*b* of the first jaw 50, whereby an upper slot surface 86*a* of the slot 86 contacts the pin 84 so as to limit the distance that the proximal end 50*b* of the first jaw 50 can be separated from the proximal end 80*b* of the second jaw 80.

In addition, the first jaw 50 and the second jaw 80 are coupled to each other at a location between their respective distal ends 50*a*, 80*a* and proximal ends 50*b*, 80*b* by an externally threaded rod 90. In the example embodiment of the present invention illustrated in FIGS. 3(*a*) to 3(*d*), the externally-threaded rod 90 is pivotably coupled at a lower end 90*a* to a pin 92 mounted in the first jaw 50. A first driver 88 engages the externally-threaded rod 90 so as to extend and retract the externally-threaded rod 90 relative to the second jaw 80, thereby opening and closing the first jaw 50 relative to the second jaw 80. In addition, a first drive socket 654 of the first driver 88 is coupled to a first motor 96 by a first drive shaft 94. As will be explained in more detail below, the first driver 88, when engaged by the first motor 96 via the first drive shaft 94, operates to open and close first jaw 50 relative to second jaw 80.

The first jaw 50 includes a clamping surface 108 that has a distal end 108*a* and a proximal end 108*b*. Similarly, the second jaw 80 includes a clamping surface 106 that has a distal end 106*a* and a proximal end 106*b*. The second jaw 80 also includes a cutting and stapling element 104, which may form at least part of the clamping surface 106 of the second jaw 80. As explained in greater detail below, the cutting and stapling element 104 is configured to cut and staple a section of tissue, e.g., tissue 52, when the first jaw 50 and the second jaw 80 are in the fully closed position illustrated in FIG. 3(*d*). The second jaw 80 also includes a second driver 98 having a second drive socket 694 that is coupled to a second motor 100 by a second drive shaft 102. The second driver 98, when engaged by the second motor 100 via the second drive shaft 102, operates to drive the cutting and stapling element 104 to cut and staple a section of tissue 52. While two drive sockets, e.g., the first drive socket 654 and the second drive socket 694, and two corresponding drive shafts, e.g., the first drive shaft 94 and the second drive shaft 102, are illustrated, it is possible to provide any suitable number of drive sockets and drive shafts. For example, a single drive shaft may be provided to operate the surgical device 11*a*.

FIG. 3(*a*) illustrates the surgical device 11*a* in a fully open position, wherein the first jaw 50 and the second jaw 80 are fully separated. In the fully open position, the externally-threaded rod 90 of the first driver 88 is in a fully extended position relative to the second jaw 80. The upper slot surface 86*a* of the slot 86 contacts the pin 84 of the second jaw 80. Thus, the distal end 50*a* of the first jaw 50 is at a maximum distance from the distal end 80*a* of the second jaw 80, and the proximal end 50*b* of the first jaw 50 is at a maximum distance from the proximal end 80*b* of the second jaw 80.

When the first driver 88 is driven in a first direction, the surgical device 11*a* is moved into a first partially closed position, as illustrated in FIG. 3(*b*). In the first partially closed position illustrated in FIG. 3(*b*), the first jaw 50 and the second jaw 80 are approximately parallel to each other, e.g., the distance between the distal end 108*a* of the clamping surface 108 of the first jaw 50 and the distal end 106*a* of the clamping surface 106 of the second jaw 80 is approximately equal to the distance between the proximal end 108*b* of the clamping surface 108 of the first jaw 50 and the proximal end 106*b* of the clamping surface 106 of the second jaw 80. As shown in FIG. 3(*b*), the externally-threaded rod 90 is partially retracted, e.g., via the first driver 88, to a position between its fully extended position and its fully retracted position. The upper slot surface 86a of the slot 86 maintains contact with the pin 84 of the second jaw 80. Thus, in moving the surgical device 11a from the fully open position illustrated in FIG. 3(a) to the first partially closed position illustrated in FIG. 3(b), the first jaw 50 pivots relative to the second jaw 80 around the stop element, e.g., around the pin 84 in contact with the upper slot surface 86a. In this embodiment, the first jaw 50 pivots due to the retraction of the externally threaded rod 90, in combination with the force of the biasing element 82. Accordingly, the biasing member 82 not only biases the proximal ends 50b, 80b of the jaws 50, 80 apart, but also biases the distal ends 50a, 80a of the jaws 50, 80 towards each other.

Figure 3A:
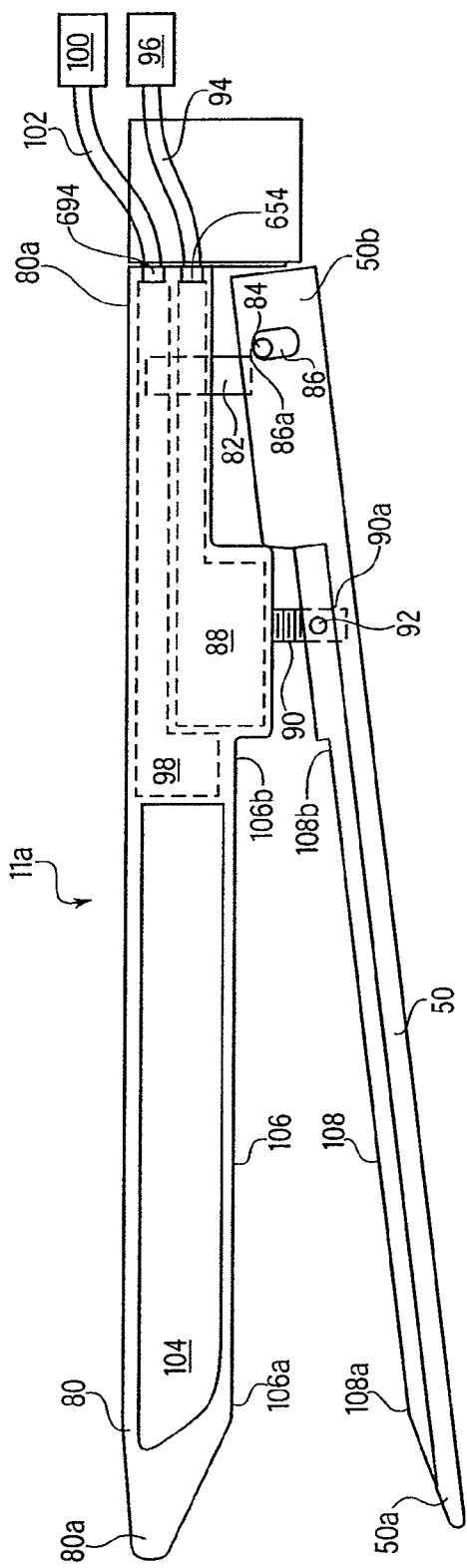
FIGS. 3(a) to 3(d) are side views of a linear clamping, cutting and stapling attachment, at various stages of its operation, according to one example embodiment of the present invention.
Figure 3B:
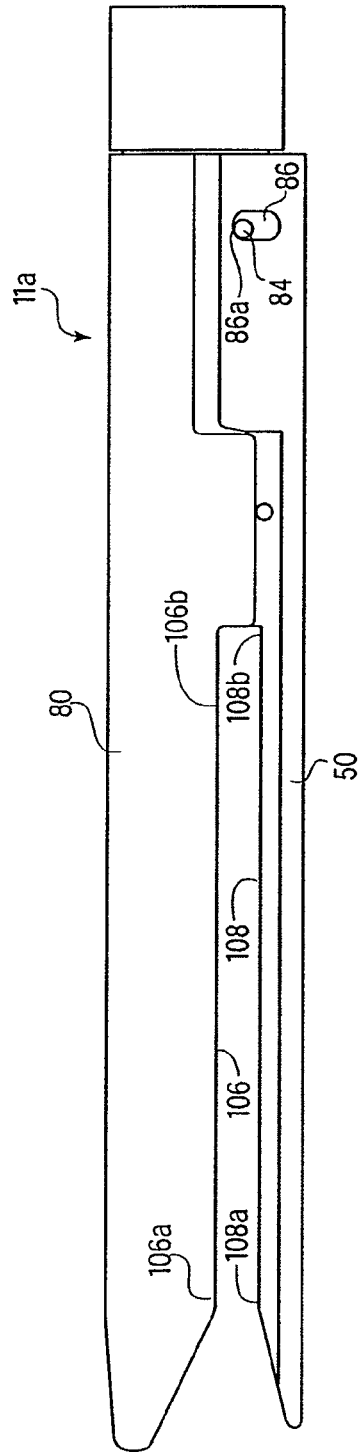
Figure 3C:
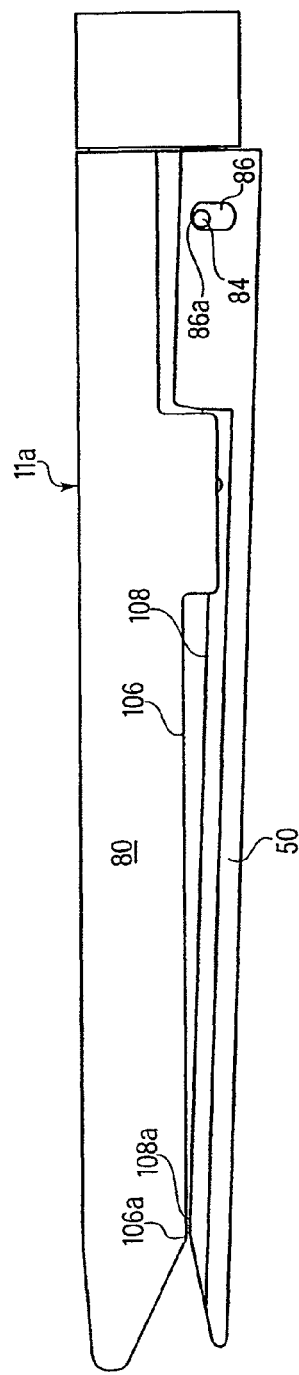

Upon further engagement of the first driver 88, the surgical device 11a is moved into a second partially closed position, as illustrated in FIG. 3(c). In the second partially closed position illustrated in FIG. 3(c), and due to the biasing element 82, the distance between the distal end 108a of the clamping surface 108 of the first jaw 50 and the distal end 106a of the clamping surface 106 of the second jaw 80 is less than the distance between the proximal end 108b of the clamping surface 108 of the first jaw 50 and the proximal end 106b of the clamping surface 106 of the second jaw 80. As shown in FIG. 3(c), the externally-threaded rod 90 is still further retracted, e.g., via the first driver 88, relative to the partially retracted position illustrated in FIG. 3(b). The upper slot surface 86a of the slot 86 still maintains contact with the pin 84 of the second jaw 80. Thus, in moving the surgical device 11a from the first partially closed position illustrated in FIG. 3(b) to the second partially closed position illustrated in FIG. 3(c), the first jaw 50 continues to pivot relative to the second jaw 80 around the stop element, e.g., around the pin 84 in contact with the upper slot surface 86a.

Figure 3D:
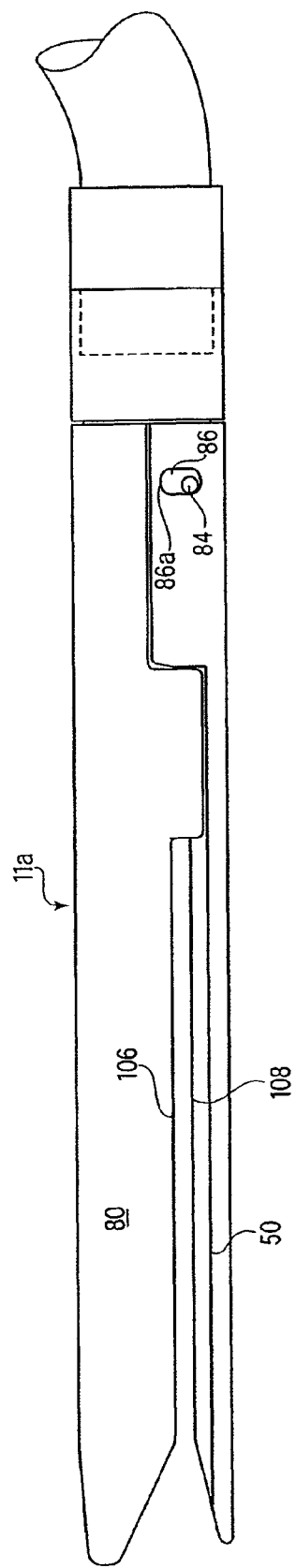

Upon still further engagement of the first driver 88, the surgical device 11a is moved into a fully closed position, as illustrated in FIG. 3(d). In the fully closed position illustrated in FIG. 3(d), the clamping surface 108 of the first jaw 50 is generally parallel to the clamping surface 106 of the second jaw 80. As shown in FIG. 3(d), the externally-threaded rod 90 is fully retracted, e.g., via the first driver 88, relative to the partially retracted position illustrated in FIG. 3(c). With the distal ends 106a, 108a of the clamping surfaces 106, 108 of the first and second jaws 50, 80 in contact as shown in FIG. 3(c), this further retraction of the externally-threaded rod 90 causes the upper slot surface 86a of the slot 86 to separate from the pin 84 of the second jaw 80. Thus, in moving the surgical device 11a from the second partially closed position illustrated in FIG. 3(c) to the fully closed position illustrated in FIG. 3(d), the first jaw 50 pivots relative to the second jaw 80 first around the distal ends 106a, 108a of the clamping surfaces 106, 108 of the first and second jaws 50, 80, and then, as the distal ends 106a and 108a are gradually separated, around the section of tissue 52. The biasing element 82, which is compressed in the position illustrated in FIG. 3(d), continues to bias apart the proximal ends 50b, 80b of the first and second jaws 50, 80, and also to bias the distal end 50a of the first jaw 50 towards the distal end 80a of the second jaw 80.

FIGS. 4(a) to 4(c) are side views of a linear clamping, cutting and stapling attachment according to another example embodiment of the present invention. Specifically, FIG. 4(a) illustrates a surgical device 11b in an open position, FIG. 4(b) illustrates the surgical device 11b in a partially closed position, and FIG. 4(c) illustrates the surgical device 11b in a closed position. In the example embodiment of the present invention illustrated in FIGS. 4(a) to 4(c), the first jaw 50 of the surgical device 11b has a curved surface 1081. In particular, the distal end 50a of the first jaw 50 is curved towards the distal end 80a of the second jaw 80. Thus, a clamping force that is exerted on a section of tissue (not shown) that is disposed between the first jaw 50 and the second jaw 80 is greater at the distal ends 50a, 80a of the first and second jaws 50, 80 than at the proximal ends 50b, 80b of the first and second jaws 50, 80, thereby helping to reduce the tendency of the section of tissue to escape out from between the distal ends 50a, 80a of the first and second jaws 50, 80. According to one example embodiment of the present invention, the first jaw 50 of the surgical device 11b is formed of a resilient, deformable material such that the first jaw 50 is configured to at least partially straighten, relative to the curved position shown in FIGS. 4(a) to 4(c), when a sufficient clamping force is exerted at the distal ends 50a, 80a of the first and second jaws 50, 80. In addition, the surgical device 11b may employ a biasing element, such as a spring coupled to the proximal ends 50b, 80b of the jaws 50, 80, as discussed above, in order to further bias the distal end 50a of the first jaw 50 towards the distal end 80a of the second jaw 80 and to provide a still greater clamping force at the distal ends 50a, 80a of the first and second jaws 50, 80 of the surgical device 11b.

Figure 5A:
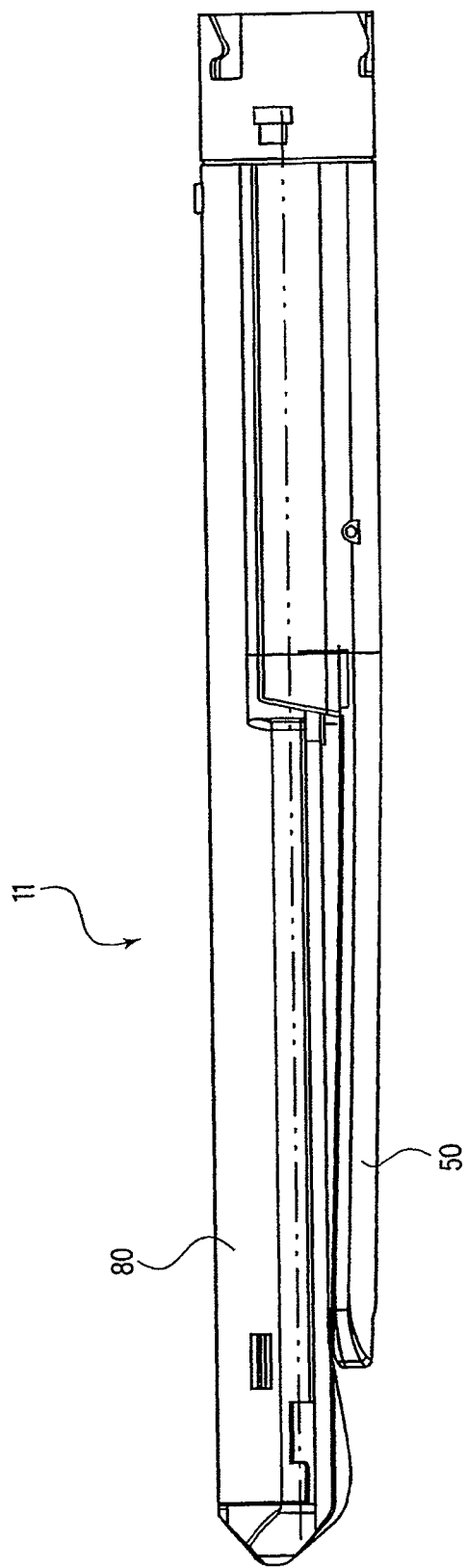
FIG. 5(a) is a side view of a linear clamping, cutting and stapling attachment according to another example embodiment of the present invention.
Figure 5B:
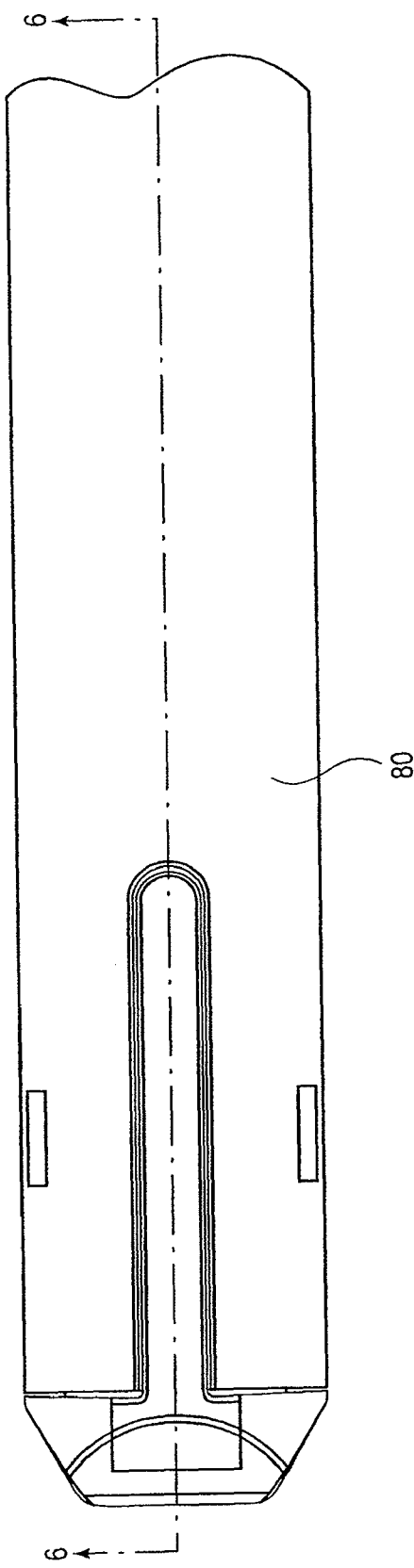
FIG. 5(b) is a partial top view of the linear clamping, cutting and stapling attachment illustrated in FIG. 5(a)

FIGS. 5(a) to 14 illustrate various views of a linear clamping, cutting and stapling attachment, according to another example embodiment of the present invention. Specifically, FIG. 5(a) is a side view of a linear clamping, cutting and stapling attachment according to one example embodiment of the present invention. The surgical device 11 is configured so as to be particularly well-suited for endoscopic insertion into the body of a patient via a cannula (not shown). FIG. 5(a) illustrates the first jaw 50 in opposed correspondence with the second jaw 80. FIG. 5(b) is a partial top view of the surgical device 11, particularly the second jaw 80, illustrated in FIG. 5(a).

FIG. 6(a) is an exploded view of a replaceable staple cartridge 600, that is configured to be employed in the example embodiment of the present invention illustrated in FIG. 5(a) to FIG. 14. The replaceable staple cartridge 600 includes a staple tray 604. The staple tray 604 has a slot 604i at its proximal end 604d in which a memory module 6041 is retained by a memory module retainer 6042. The memory module 6041 may store information as described, for example, in U.S. patent application Ser. No. 09/723,715, filed on Nov. 28, 2000, U.S. patent application Ser. No. 09/836,781, filed on Apr. 17, 2001, U.S. patent application Ser. No. 09/887,789, filed on Jun. 22, 2001(?) and U.S. patent application Ser. No. 10/099,634, filed on Mar. 15, 2002 each of which is expressly incorporated herein by reference in its entirety. A wedge driver 605 is configured to be rotatably disposed through a central channel 604e of the staple tray 604. Specifically, the wedge driver 605 has a distal end 605a that is configured to be rotatably mounted within a distal orifice 604a of the staple tray 604. The wedge driver 605 also includes an externally threaded region 605b, a non-threaded portion 605c that rotatably extends through a proximal orifice 604b in the proximal end 604b of the staple tray 604, and a spur gear 605d at its proximal-most end.

The replaceable staple cartridge 600 also includes a wedge 603 having an internally threaded bore 603a. The externally threaded region 605b of the wedge driver 605 is configured to extend through the internally threaded bore 603a of the wedge 603. The threads of the internally threaded bore 603a of the wedge 603 match the threads of the externally threaded region 605b of the wedge driver 605. As is discussed further below, upon rotation of the wedge driver 605, the wedge 603 is moved between the distal end 604*c* of the staple tray 604 and the proximal end 604*d* of the staple tray 604 through a central channel 604*e*.

The staple tray 604 also includes a plurality of vertically-disposed slots 604*f* in opposing walls 604*g* of the central channel 604*e*. On each side of the central channel 604*e*, a staple pusher 607 is configured to be slideably disposed within the slots 604*f*. More specifically, each of the staple pushers 607 has a top surface 607*a* running longitudinally between two rows 607*b* of staple pushing fingers 607*c*. The staple pushing fingers 607*c* are configured such that each staple pushing finger 607*c* in the row 607*b* that abuts the wall 604*g* of the staple tray 604 is retained within a corresponding slot 604*f* of the wall 604*g* so as to be vertically slideable therein. The staple pushing fingers 607*c* are positioned over slots 604*h* in the staple tray 604. The slots 604*h* in the staple tray 604 house a plurality of fasteners, e.g., staples 606. Each of the staples 606 includes a butt 606*a* and a pair of prongs 606*b*.

The wedge 603 also includes a pair of sloped edges 603*b* that slideably engage respective top surfaces 607*a* of the staple pushers 607. When the wedge 603 is moved from the distal end 604*c* to the proximal end 604*d* of the staple tray 604 through the central channel 604*e*, the pair of sloped edges 603*b* of the wedge 603 is configured to slideably engage the respective top surfaces 607*a* of the staple pushers 607 in order to successively push the staple pushing fingers 607*c* of the staple pushers 607 into, and thus the staples 606 out of, the slots 604*h* in the staple tray 604. A cartridge top 611 is configured to fit over the central channel 604*a* of the staple tray 604, while a staple retainer 610 is configured to cover the clamping surface 106 of the staple tray 604.

FIG. 6(*b*) is a cross-sectional view of the linear clamping, cutting and stapling attachment taken along the line 6-6 shown in FIG. 5(*b*). FIG. 6(*b*) illustrates the surgical device 11 in a fully closed position, in which the externally threaded rod 90 is fully retracted. In FIG. 6(*b*), the surgical device 11 is illustrated absent a section of tissue between the clamping surfaces 106, 108 of the first and the second jaws 50, 80, and thus the surgical device 11 is shown in this fully closed position having the distal end 108*a* of the clamping surface 108 of the first jaw 50 in contact with the distal end 106*a* of the clamping surface 106 of the second jaw 80.

As illustrated in FIG. 6(*b*), the surgical device 11 includes a cutting and stapling element 104 disposed within the second jaw 80. According to the example embodiment of the present invention shown, the cutting and stapling element 104 includes the replaceable staple cartridge 600 of FIG. 6(*b*) that is replaceably mountable within the second jaw 80. The replaceable staple cartridge 600, which was shown in an exploded view in FIG. 6(*a*), is shown assembled and mounted within the second jaw 80 in FIG. 6(*b*).

As illustrated in FIG. 6(*b*), the wedge 603 has disposed thereon a blade 51 having a cutting edge 51*a*. In an alternative example embodiment, the cutting and stapling elements may be separately disposed. In the example embodiment illustrated in FIG. 6(*b*), the surgical device 11 includes a blade 51 having a tail region 654 with a contact face 653. The blade 51 is rotatably coupled to the wedge 603 around pivot 51*b* to allow the blade 51 to rotate between a first and a second position. FIG. 6(*b*) illustrates the wedge 603 and the blade 51 in several positions, labeled as positions A to E, as the wedge 603 and the blade 51 travel from the distal end 604*c* to the proximal end 604*d* of the staple tray 604.

In the position labeled A, the wedge 603 and the blade 51 are positioned at the distal end 604*c* of the staple tray 604. In the position labeled A, the wedge 603 and the blade 51 are housed within a housing 615 and the blade 51 is rotated relative to the wedge 603 so as to be in a retracted position, e.g., the cutting edge 51*a* facing upwards and is not exposed. The contact face 653 initially faces the proximal end 604*d* of the staple tray 604.

In operation, the second driver 98 causes the wedge 603 and the blade 51 to advance to the position labeled B, via, for example, rotation of the wedge driver 605. In the position labeled B, the wedge 603 and the blade 51 are positioned proximally relative to the distal end 604*c* of the staple tray 604. Specifically, in the position labeled B, the wedge 603 and the blade 51 are positioned such that the contact face 653 of the blade 51 begins to contact an actuating lip 615*a* of the housing 615. As the contact face 653 of the blade 51 begins to contact the actuating lip 615*a* of the housing 615, the blade 51 begins to rotate relative to the wedge 603.

Further operation of the second driver 98 causes the wedge 603 and the blade 51 to advance to the position labeled C. In the position labeled C, the wedge 603 and the blade 51 are positioned still further proximally relative to the distal end 604*c* of the staple tray 604. Specifically, in the position labeled C, the wedge 603 and the blade 51 are positioned such that the contact face 653 of the blade 51 has fully contacted the actuating lip 615*a* of the housing 615. When the contact face 653 of the blade 51 has fully contacted the actuating lip 615*a* of the housing 615, the blade 51 is fully rotated relative to the wedge 603 such that the cutting edge 51*a* of the blade 51 is in an extended position, e.g., the cutting edge 51*a* faces the proximal end 604*d* of the staple tray 604.

Further operation of the second driver 98 causes the wedge 603 and the blade 51 to advance to the position labeled D. In the position labeled D, the wedge 603 and the blade 51 are positioned approximately at the midpoint between the distal end 604*c* and the proximal end 604*d* of the staple tray 604. In the position labeled D, the blade 51 is maintained in the extended position having the cutting edge 51*a* facing the proximal end 604*d* of the staple tray 604 so as to cut a section of tissue (not shown) that is clamped between the first jaw 50 and the second jaw 80.

Further operation of the second driver 98 causes the wedge 603 and the blade 51 to advance to the position labeled E. In the position labeled E, the wedge 603 and the blade 51 are positioned at the proximal end 604*d* of the staple tray 604. In the position labeled E, the blade 51 is still maintained in the extended position with the cutting edge 51*a* facing the proximal end 604*d* of the staple tray 604. Here, however, the blade 51 is enclosed within a housing 616 so that the cutting edge 51*a* is not exposed.

As illustrated in FIG. 6(*b*), the first jaw 50 includes an anvil member 700 in opposed correspondence with the second jaw 80. The anvil member 700 includes the clamping surface 108, which, along with the clamping surface 106 of the second jaw 80, clamps a section of tissue to be cut and stapled.

The surgical device 11 also includes a biasing element 82 that biases the proximal end 50*b* of the first jaw 50 apart from the proximal end 80*b* of the second jaw 80, and a stop member that limits the distance that the proximal end 50*b* of the first jaw 50 can be separated from the proximal end 80*b* of the second jaw 80. In the example embodiment of the present invention illustrated in FIG. 6(*b*), the biasing element 82 includes a spring 705 maintained in a cylindrical housing 706 of the surgical device 11. Specifically, a first end of the spring 705 contacts an interior surface 5010 of the first jaw 50 and a second end of the spring 705 contacts a housing wall 708 of the cylindrical housing 706. A stop member 707 is fixedly connected at a first end 707*a* to the first jaw 50, extends through the center of the spring 705 and through an orifice 708a of the housing wall 708 and into a cylindrical housing 709. A second end 707b of the stop member 707 contacts an interior surface of the second jaw 80 when the first jaw 50 and the second jaw 80 are in the closed position illustrated in FIG. 6(b). The second end 707b of the stop member 707 preferably has a T-shape that contacts the cylindrical housing wall 709 but can not extend through the orifice 708a. Thus, the contact of the second end 707b of the stop member 707 against the cylindrical housing wall 708 operates to limit the distance that the proximal end 50b of the first jaw 50 can be separated from the proximal end 80b of the second jaw 80.

Similar to the embodiment discussed above with respect to FIGS. 3(a) to 3(d), the second jaw 80 of the surgical device 11 also includes a first driver 88 that is coupled to a first motor 96 by a first drive shaft 94 such that, when engaged by the first motor 96 via the first drive shaft 94, the first driver 88 operates to open and close first jaw 50 relative to second jaw 80. In the example embodiment shown in FIG. 6(b), the first driver 88 includes an externally-threaded rod 90 that is pivotably coupled at a lower end 90a to a pin 92 in the first jaw 50. The externally threaded rod 90 has a stopper 90c at an upper end 90b. FIG. 6(b) illustrates a bevel gear nut 617 that forms a part of the first driver 88. The bevel gear nut 617 is rotatably seated within a bearing nut 618. The bearing nut 618 is non-rotatably seated within an orifice of a housing plate 619 that is horizontally and fixedly disposed within the surgical device 11. The bevel gear nut 617 has an internally threaded bore 617a through which is disposed the externally threaded rod 90 whereby the threads of the internally threaded bore 617a of the bevel gear nut 617 match the threads of the externally threaded rod 90. The bevel gear nut 617 also includes a plurality of gear teeth 617b.

FIG. 6(b) illustrates a bevel gear driver 620 that also forms a part of the first driver 88. The bevel gear driver 620 has a bevel gear 621 at one end that is rotatably seated within a bevel bearing 622. The bevel bearing 622 is non-rotatably seated within an orifice of a housing plate 623 that is vertically and fixedly disposed within the surgical device 11. The plurality of gear teeth 617b of the bevel gear nut 617 engage a corresponding plurality of gear teeth 621a of the bevel gear 621. The bevel gear driver 620 also includes a first longitudinal region 620b and a second longitudinal region 620c. The second longitudinal region 620b of the bevel gear driver 620 extends through an orifice in a housing plate 624 that is vertically and fixedly disposed within the surgical device 11.

In this embodiment, a gear cluster 625 also forms a part of the first driver. The gear cluster 625 has an interior central bore 626 through which the bevel gear driver 620 extends. The gear cluster 625 has several longitudinally disposed regions. A first region 625a of the gear cluster 625 has a smooth cylindrical outer surface with a circular cross-section. In addition, the first region 625a of the gear cluster 625 has a radially disposed bore 6251 through which is disposed a pin 6252. The pin 6252 extends through the bore 6251 of the first region 625a of the gear cluster 625 and into a corresponding radially disposed bore 6201 in the first longitudinal region 620b of the bevel gear driver 620 in order to non-rotatably couple the gear cluster 625 to the bevel gear driver 620. A second region 625b of the gear cluster 625 defines a spur gear 627 having a plurality of circumferentially-disposed spur gear teeth 6271. A third region 625c of the gear cluster 625 also defines a spur gear 628 having a plurality of circumferentially-disposed spur gear teeth 6281. A fourth region 625d of the gear cluster 625 also defines a spur gear 629 having a plurality of circumferentially-disposed spur gear teeth 6291.

Additionally, in this example embodiment, the first driver further includes a gear cluster 630. The gear cluster 630 has an interior central bore 630a through which a gear pin 631 extends. The gear pin 631 has a distal end 631a that is rotatably housed within an orifice 632a of a vertically-disposed housing plate 632 of a gearbox 6000 fixedly mounted within the surgical device 11, and a proximal end 631b that rotatably extends through an orifice 635a in a verticaly-disposed housing plate 635 of the gearbox 6000. The gear cluster 630 has several longitudinally disposed regions. A first region 630b of the gear cluster 630 defines a spur gear 633 having a plurality of circumferentially-disposed spur gear teeth 6331. A second region 630c of the gear cluster 630 also defines a spur gear 634 having a plurality of circumferentially-disposed spur gear teeth 6341. The surgical device 11 is configured such that the spur gear teeth 6331 of the spur gear 633 of the gear cluster 630 engage the spur gear teeth 6271 of the spur gear 627 of the gear cluster 625. Simultaneously, the spur gear teeth 6341 of the spur gear 634 of the gear cluster 630 engage the spur gear teeth 6281 of the spur gear 628 of the gear cluster 625.

The surgical device 11 also includes a keyplate assembly 710 that is connected to the proximal end of the surgical device 11. The keyplate 710 includes an internally threaded bore 710a that is aligned with an internally threaded bore 711a of a housing wall 711 of the gearbox 6000 of the surgical device 11. An externally threaded screw 712, the threads of which mate with the threads of internally threaded bores 710a and 711a, extends through the keyplate assembly 710 and the housing wall 711 so as to fixedly connect the keyplate assembly 710 to the housing wall 711. The keyplate assembly 710 also includes a quick connect sleeve 713 that has quick connect slots 713a that engage complementary quick connect elements 1664 of a flexible drive shaft 1620, which is described in further detail below. In order to retain the quick connect elements 1664 of the flexible drive shaft 1620 in the quick connect slots 713a of the quick connect sleeve 713, the keyplate assembly 710 also includes a keyplate spring 714.

Figure 7:
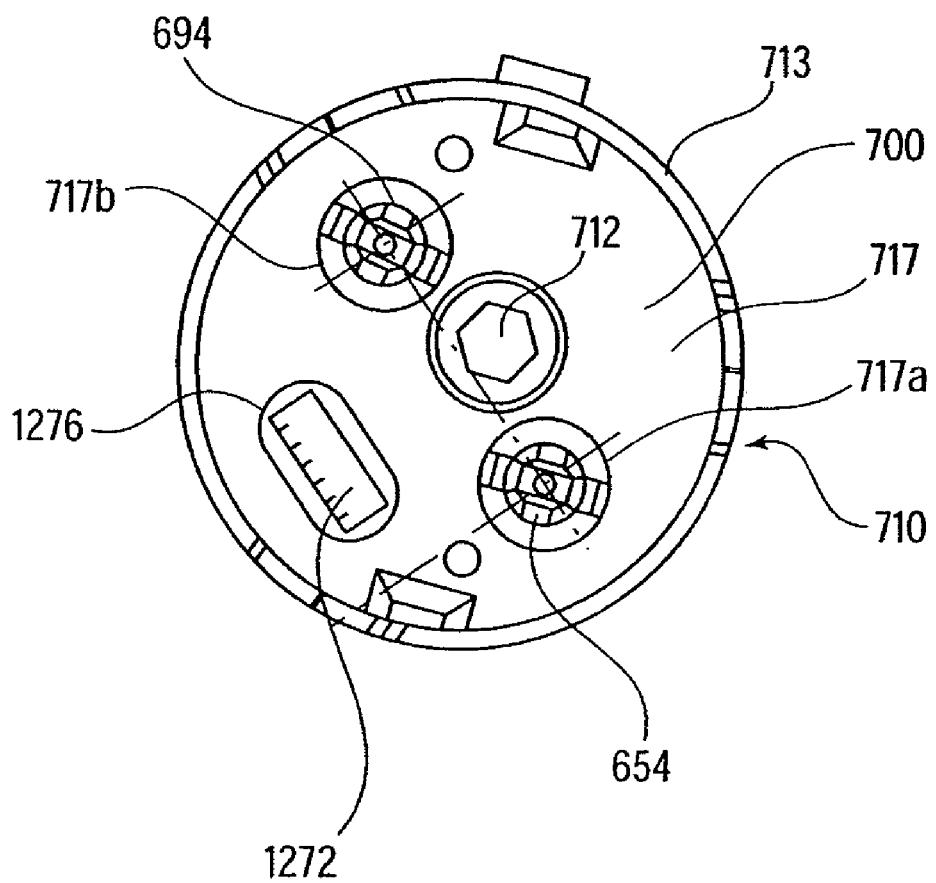
FIG. 7 is a rear view of the linear clamping, cutting and stapling attachment illustrated in FIG. 5(a)

Additional features of the keyplate assembly 710 are illustrated in FIG. 7, which is a rear view of the linear clamping, cutting and stapling attachment illustrated in FIG. 5(a). Referring now to FIG. 7, a backstop plate 717 is disposed between the keyplate assembly 710 and the housing wall 711. The backstop plate 717 is held in place by the screw 712 and has orifices 717a and 717b through which extend the first drive socket 654 of the first driver 88 and the second drive socket 694 of the second driver 98. The keyplate assembly 710 also includes a data connector 1272 that includes electrical contacts 1276. The data connector 1272 of the keyplate assembly 710 is electrically and logically connected to the memory module 6041 housed at the proximal end 604b of the staple tray 604, by a flexible data transfer cable (not shown) extending therebetween.

Figure 8:
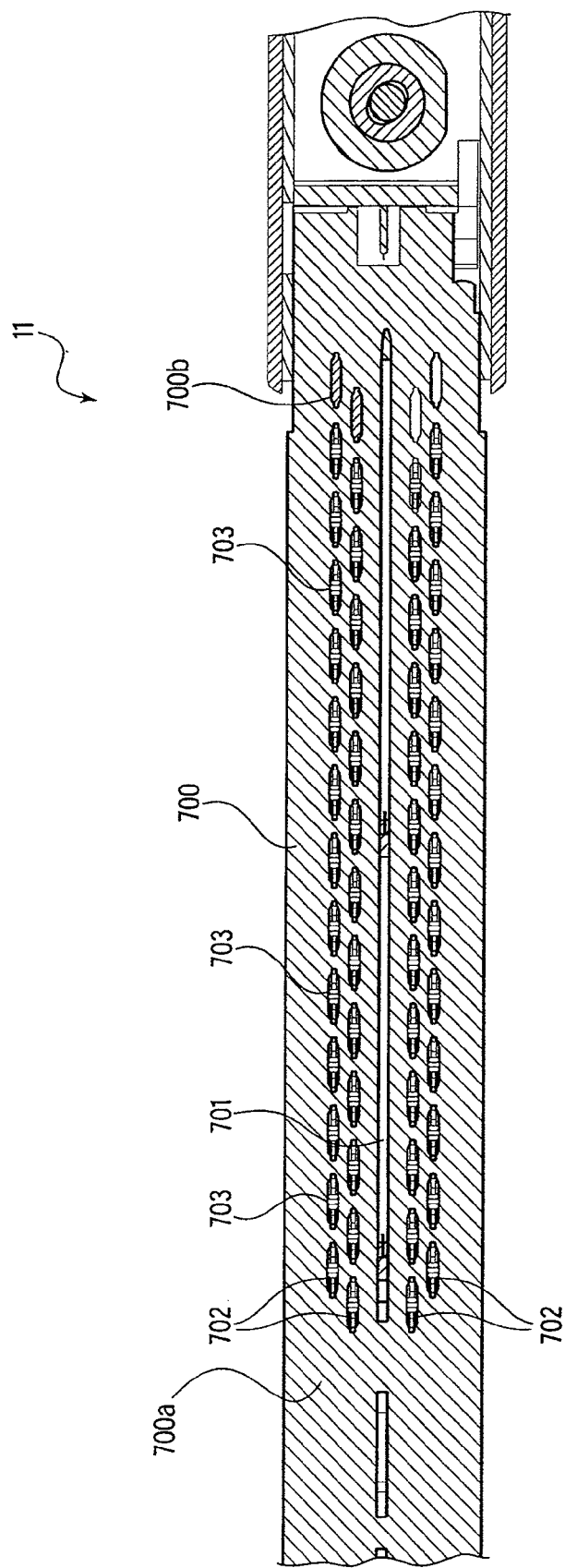
FIG. 8 is a cross-sectional view of the linear clamping, cutting and stapling attachment taken along the line 8-8 shown in FIG. 6(*b*)

FIG. 8 is a cross-sectional view of the linear clamping, cutting and stapling attachment taken along the line 8-8 shown in FIG. 6(b). Referring now to FIG. 8, the anvil member 700 includes a longitudinally-disposed slot 701 that extends from a distal end 700a to a proximal end 700b of the anvil member 700. The slot 701 is aligned with the blade 51 of the second jaw 80 so that blade 51 extends into and travels along the slot 701 when the blade is moved from the distal end 80a to the proximal end 80b of the second jaw 80. The anvil member 700 also includes a plurality of rows 702 of staple guides 703. The staple guides 703 are configured to receive the prongs 606b of the staples 606 when the surgical device 11 is fired and to bend the prongs 606b so as to close the staples 606. When the surgical device 11 is in the closed position, the rows 702 of the staple guides 703 align with the slots 604h of the staple tray 604 in the second jaw 80 so that the staples 606 maintained in the slots 604h of the staple tray 604 are pushed by the staple pushing fingers 607c of the staple pushers 607 into, and closed by, corresponding staple guides 703 of the anvil member 700.

Figure 9:
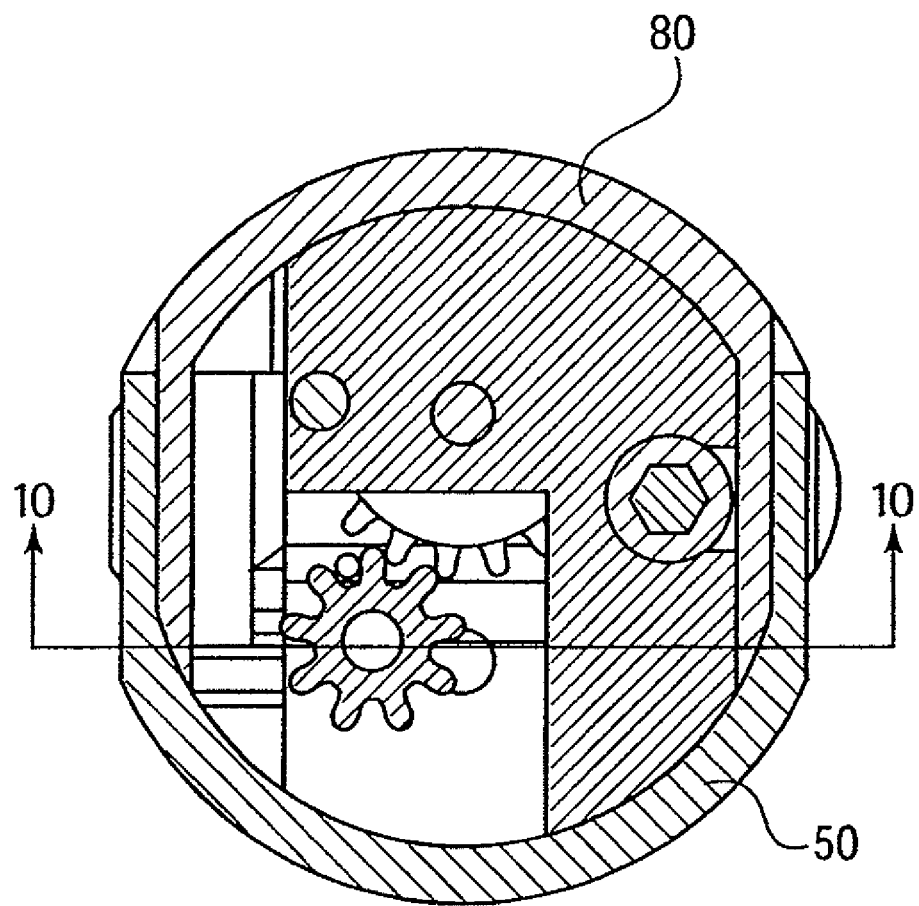
FIG. 9 is a cross-sectional view of the linear clamping, cutting and stapling attachment taken along the line 9-9 shown in FIG. 6(*b*)
Figure 10:
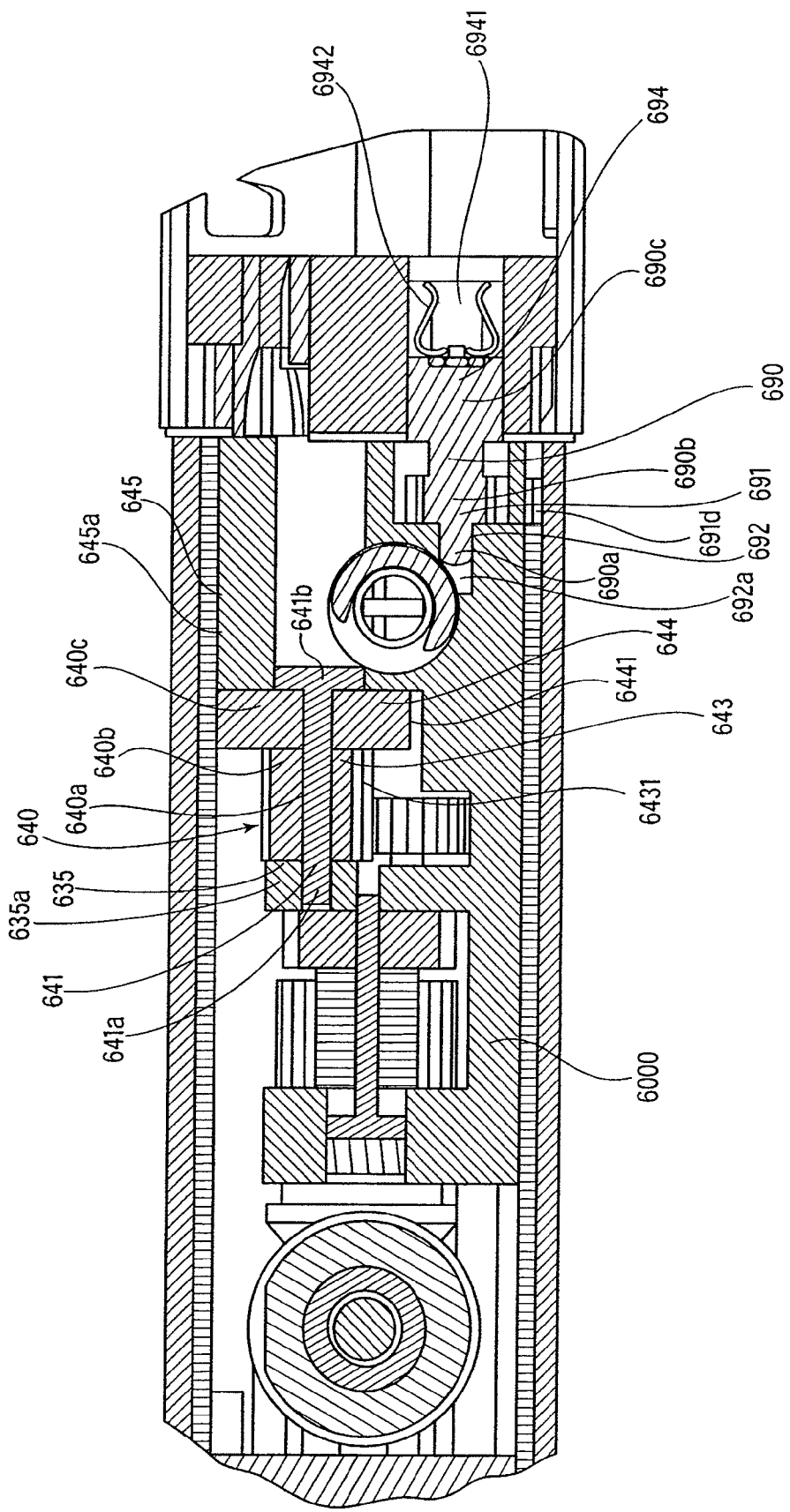
FIG. 10 is a cross-sectional view of the linear clamping, cutting and stapling attachment taken along the line 10-10 shown in FIG. 9.

FIG. 9 is a cross-sectional view of the linear clamping, cutting and stapling attachment taken along the line 9-9 shown in FIG. 6(b). FIG. 10 is a cross-sectional view of the linear clamping, cutting and stapling attachment taken along the line 10-10 shown in FIG. 9. FIG. 10 illustrates a gear cluster 640 that forms a part of the first driver 88. The gear cluster 640 has an interior central bore 640a through which a gear pin 641 extends. The gear pin 641 has a distal end 641a that is rotatably housed within an orifice 635a of the housing plate 635 of the gearbox 6000 and a proximal end 641b that rotatably extends through an orifice 645a in a vertically-disposed housing plate 645 of the gearbox 6000. The gear cluster 640 has several longitudinally disposed regions. A first region 640b of the gear cluster 640 defines a spur gear 643 having a plurality of circumferentially-disposed spur gear teeth 6431. A second region 640c of the gear cluster 640 also defines a spur gear 644 having a plurality of circumferentially-disposed spur gear teeth 6441. The surgical device 11 is configured such that the spur gear teeth 6431 of the spur gear 643 of the gear cluster 640 engage the spur gear teeth 6291 of the spur gear 629 of the gear cluster 625.

FIG. 10 also illustrates a fire shaft assembly 690 that forms a part of the second driver 98. As previously discussed with respect to FIGS. 3(a) to 3(d), the second driver 98 is coupled to a second motor 100 by a second drive shaft 102, and operates to drive the cutting and stapling element 104 to cut and staple a section of tissue 52. The fire shaft assembly 690 has several longitudinally disposed regions. A first region 690a of the fire shaft assembly 690 extends into and is rotatable within an orifice 692a of a vertically-disposed housing plate 692 of the gearbox 6000. A second region 690b of the fire shaft assembly 690 defines a spur gear 691 having a plurality of circumferentially-disposed spur gear teeth 6911. A third region 690c of the fire shaft assembly 690 defines a second drive socket 694. The second drive socket 694 includes a slot 6941 into which a drive clip 6942 is inserted. The drive clip 6942 is configured to be non-rotatably, releasably connected to a complementary second drive coupling 1668 of the second drive shaft 102, which is discussed in further detail below.

Figure 11:
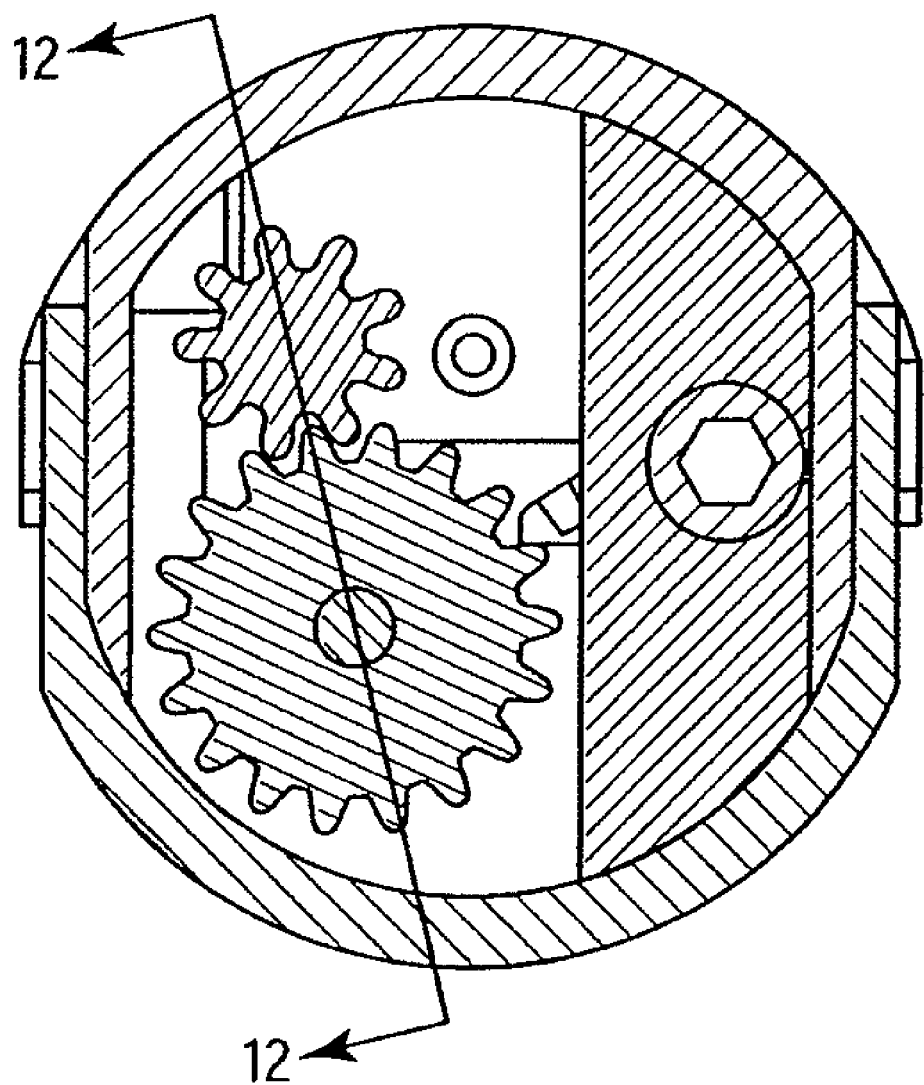
FIG. 11 is a cross-sectional view of the linear clamping, cutting and stapling attachment taken along the line 11-11 shown in FIG. 6(*b*)
Figure 12:
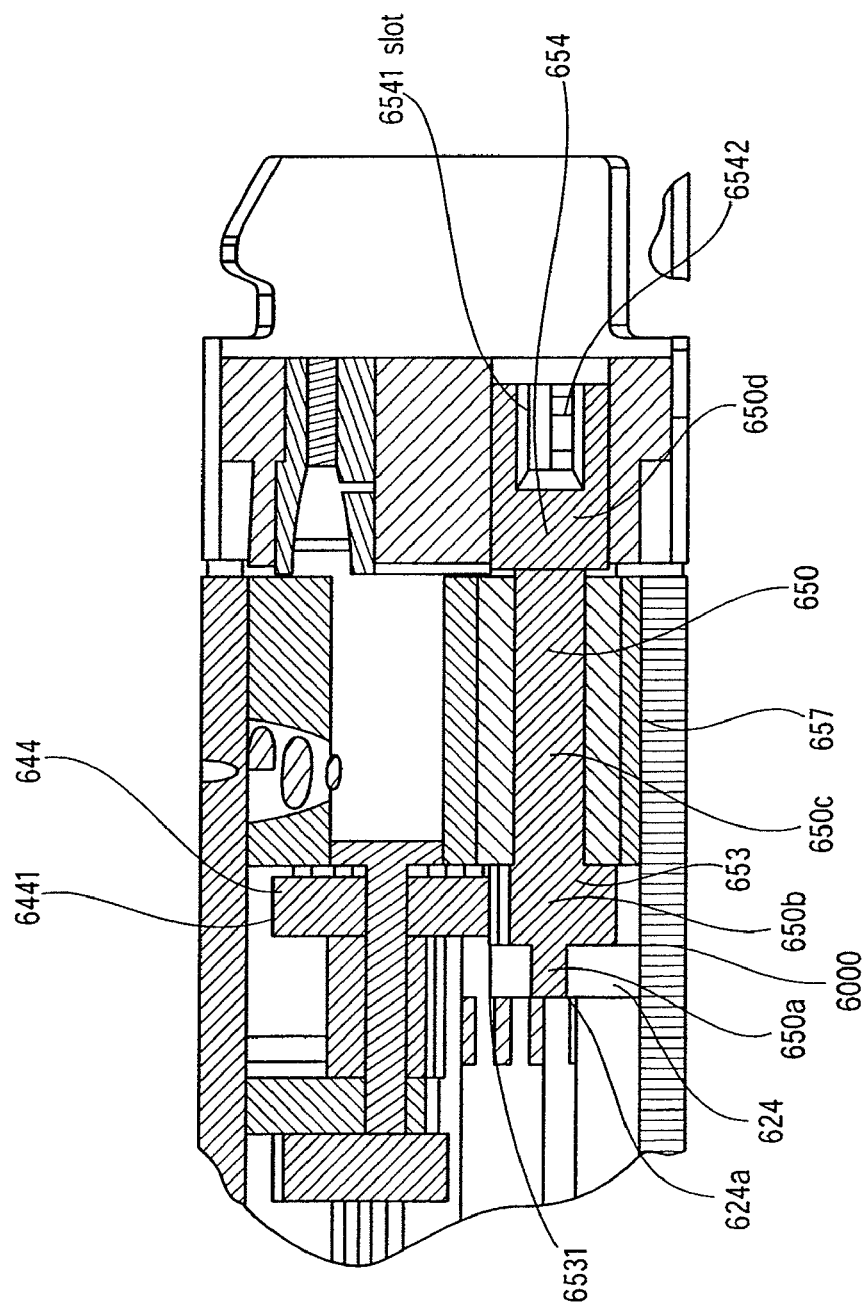
FIG. 12 is a cross-sectional view of the linear clamping, cutting and stapling attachment taken along the line 12-12 shown in FIG. 11.

FIG. 11 is a cross-sectional view of the linear clamping, cutting and stapling attachment taken along the line 11-11 shown in FIG. 6(b). FIG. 12 is a cross-sectional view of the linear clamping, cutting and stapling attachment taken along the line 12-12 shown in FIG. 11. FIG. 12 illustrates a clamp shaft assembly 650 that forms a part of the first driver 88. The clamp shaft assembly 650 has several longitudinally disposed regions. A first region 650a of the clamp shaft assembly 650 extends into and is rotatable within an orifice 624a of the housing plate 624 of the gearbox 6000. A second region 650b of the clamp shaft assembly 650 defines a spur gear 653 having a plurality of circumferentially-disposed spur gear teeth 6531. The surgical device 11 is configured such that the spur gear teeth 6531 of the spur gear 653 of the clamp shaft assembly 650 engage the spur gear teeth 6441 of the spur gear 644 of the gear cluster 640. A third region 650c of the clamp shaft assembly 650 defines a straight longitudinal shaft that is partially surrounded by a gear spacer 657 that maintains the longitudinal position of the clamp shaft assembly 650 by abutting against spur gear 653. A fourth region 650d of the clamp shaft assembly 650 defines a first drive socket 654. The first drive socket includes a slot 6541 into which a drive clip 6542 is inserted. The drive clip 6542 is configured to be non-rotatably, releasably connected to a complementary first drive coupling 1666 of the first drive shaft 94, which is discussed in further detail below.

Figure 13:
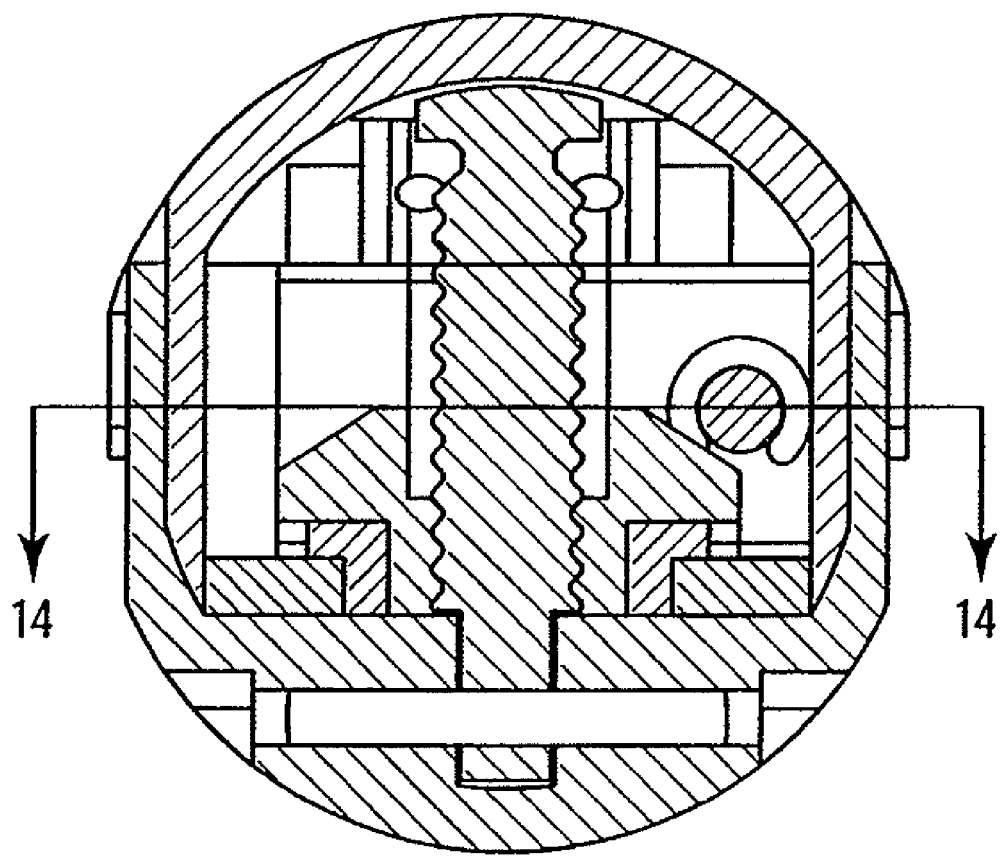
FIG. 13 is a cross-sectional view of the linear clamping, cutting and stapling attachment taken along the line 13-13 shown in FIG. 6(*b*)
Figure 14:
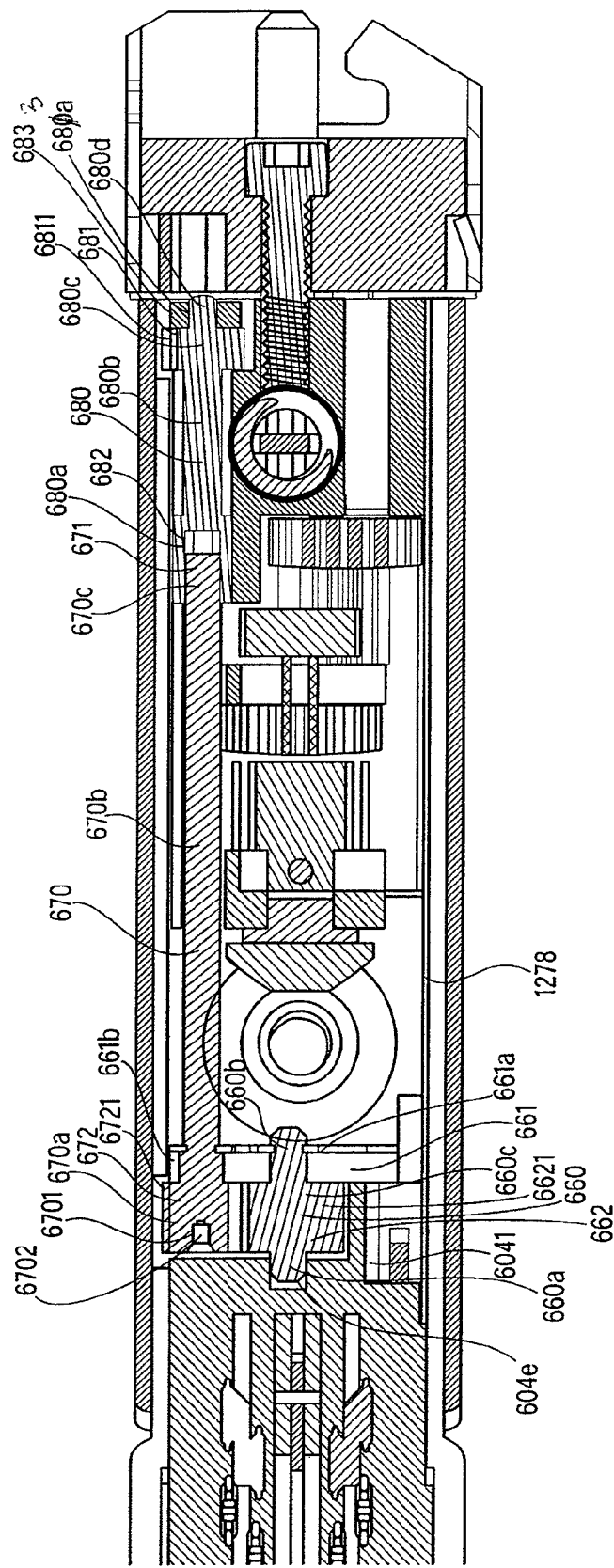
FIG. 14 is a cross-sectional view of the linear clamping, cutting and stapling attachment taken along the line 14-14 shown in FIG. 13.

FIG. 13 is a cross-sectional view of the linear clamping, cutting and stapling attachment taken along the line 13-13 shown in FIG. 6(b). FIG. 14 is a cross-sectional view of the linear clamping, cutting and stapling attachment taken along the line 14-14 shown in FIG. 13. FIG. 14 illustrates a shuttle idler gear 660 that forms a part of the second driver 98. The shuttle idler gear 660 has a first end 660a that extends into and is rotatably supported in an orifice 604e of a housing plate 6041 that is vertically and fixedly disposed within the surgical device 11. Similarly, the shuttle idler gear 660 has a second end 660b that extends through and is rotatably supported in an orifice 661a of a vertically-disposed housing plate 661 of the gearbox 6000. The shuttle idler gear 660 also has a central region 660c that defines a spur gear 662 having a plurality of circumferentially-disposed spur gear teeth 6621. The surgical device 11 is configured such that the spur gear teeth 6621 of the spur gear 662 of the shuttle idler gear 660 engage the spur gear teeth 6051 of the spur gear 605d at the proximal end of the wedge driver 605 of the replaceable staple cartridge 600.

FIG. 14 also illustrates a counter shaft assembly 670 that forms a part of the second driver 98. The counter shaft assembly 670 has several longitudinally disposed regions. A first region 670a of the counter shaft assembly 670 extends through and is rotatable within an orifice 661b of the housing plate 661 of the gearbox 6000. In addition, the first region 670a defines a spur gear 672 having a plurality of circumferentially-disposed spur gear teeth 6721. The example surgical device 11 is configured such that the spur gear teeth 6721 of the spur gear 672 of the counter shaft assembly 670 engage the spur gear teeth 6621 of the spur gear 662 of the shuttle idler gear 660. In addition, the first region 670a of the counter shaft assembly 670 includes an axially-tapered bore 6701 into which is insertable a pin 6702 extending from the proximal end 604d of the staple tray 604, thereby helping to insure that the staple cartridge 600 is properly inserted within, and properly engages, the first driver 88 of the second jaw 80. A second region 670b of the counter shaft assembly 670 defines a straight longitudinal shaft. A third region 670c of the counter shaft assembly 670 defines a coupling 671, e.g., a male, hexagonally-shaped coupling.

FIG. 14 also illustrates a counter shaft assembly 680 that forms a part of the second driver 98. The counter shaft assembly 680 has several longitudinally disposed regions. A first region 680a of the counter shaft assembly 680 defines a coupling 682, e.g., a female, hexagonally-shaped coupling, that is configured to be non-rotatably coupled to the coupling 671 of the counter shaft assembly 670. A second region 680b of the counter shaft assembly 680 defines a straight longitudinal shaft. A third region 680c of the counter shaft assembly 680 defines a spur gear 681 having a plurality of circumferentially-disposed spur gear teeth 6811. The surgical device 11 is configured such that the spur gear teeth 6811 of the spur gear 681 of the counter shaft assembly 680 engage the spur gear teeth 6911 of the spur gear 691 of the fire shaft assembly 690. A fourth region 680d of the counter shaft assembly 680 extends into and is rotatable within an orifice 683a of a guide bushing 683 that is mounted within the surgical device 11.

FIG. 14 further illustrates a flexible data transfer cable 1278. The flexible data transfer cable 1278, as previously discussed, electrically and logically connects the memory module 6041 retained in the slot 604i at the proximal end 604d of the staple tray 604 to the data connector 1272 of the keyplate assembly 710. Advantageously, in this example embodiment, the flexible data transfer cable 1278 is a flat data cable that extends along the interior surface 8010 of the second jaw 80 and that has minimal cross-sectional area, e.g., so as to avoid contact with the various gear arrangements described above.

According to one example embodiment of the present invention, the surgical device 11 may be configured as an attachment to, or may be integral with, an electro-mechanical surgical system, such as electro-mechanical driver system 1510. In another embodiment, the surgical device 11 may be configured as an attachment to, or may integral with, a purely mechanical device driver system, such as that illustrated in FIG. 1.

Figure 2:
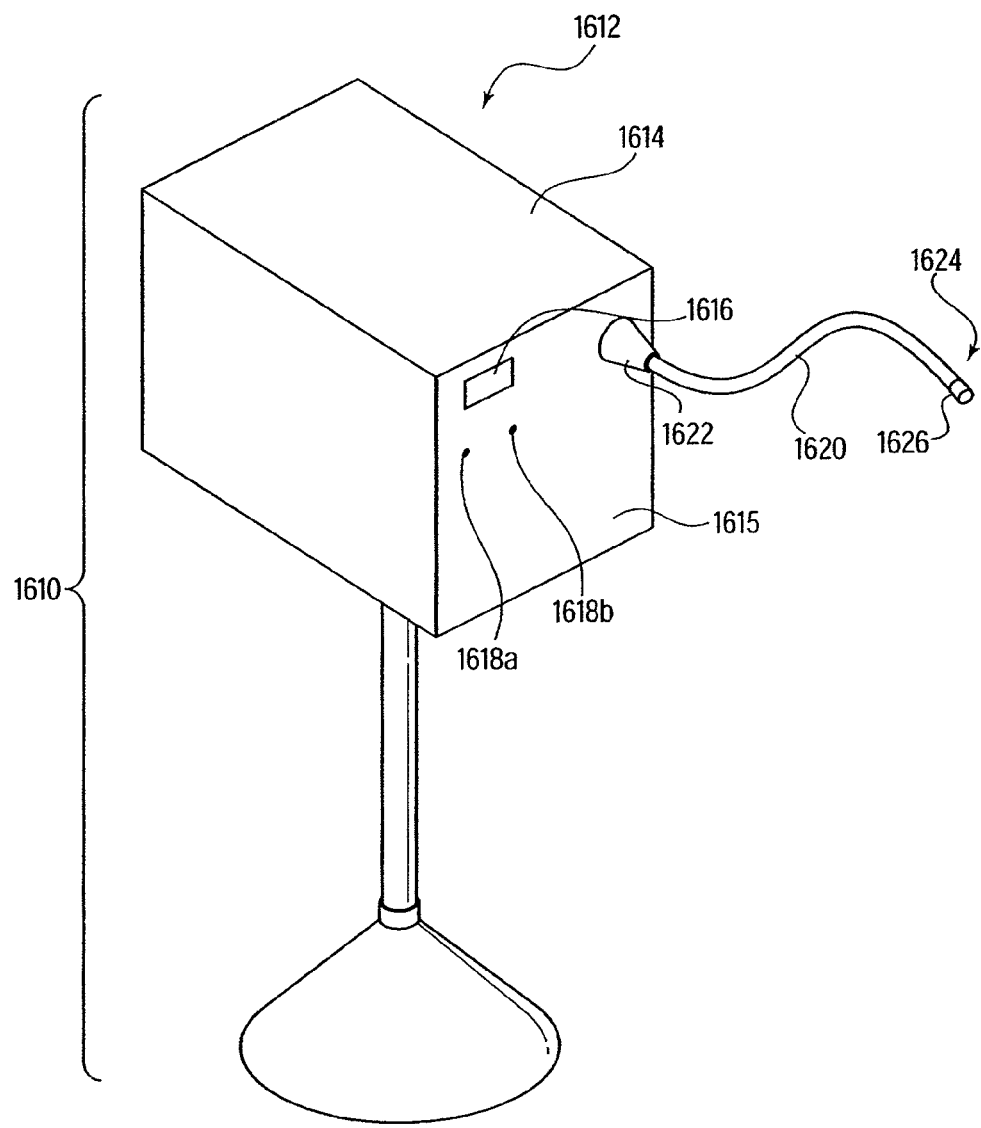
FIG. 2 is a perspective view of an electro-mechanical surgical system according to one example embodiment of the present invention.

FIG. 2 is a perspective view of an example embodiment of an electro-mechanical driver component 1610 according to the present invention. Such an electro-mechanical surgical system is described in, e.g., U.S. patent application Ser. No. 09/723,715, U.S. patent application Ser. No. 09/836,781, and U.S. patent application Ser. No. 09/887,789, each of which is expressly incorporated herein in their entirety by reference thereto. The electro-mechanical driver component 1610 may include, for example, a remote power console 1612, which includes a housing 1614 having a front panel 1615. Mounted on the front panel 1615 are a display device 1616 and indicators 1618*a*, 1618*b*. A flexible shaft 1620 may extend from the housing 1614 and may be detachably attached thereto via a first coupling 1622. The distal end 1624 of flexible shaft 1620 may include a second coupling 1626 adapted to detachably couple, e.g., the surgical device 11 described above, to the distal end 1624 of the flexible shaft 1620. The second coupling 1626 may also be adapted to detachably attach a different surgical instrument or attachment. In another example embodiment, the distal end 1624 of the flexible shaft 1620 may permanently attach to or be integral with a surgical instrument.

Figure 15:
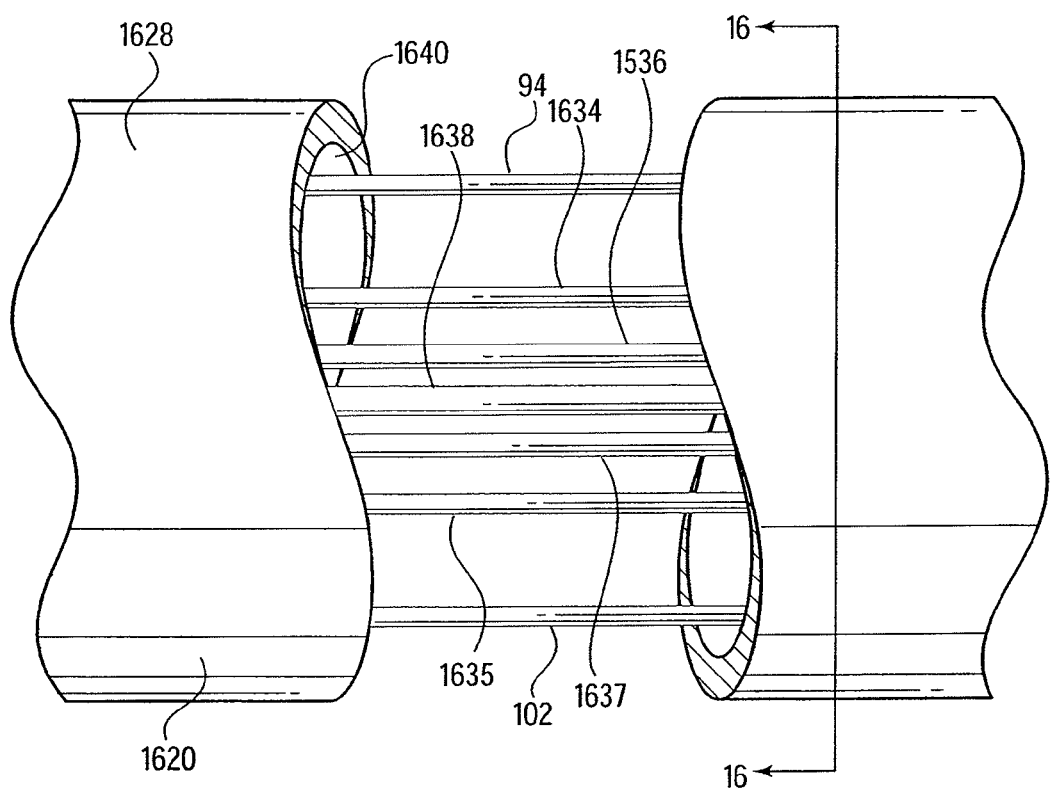
FIG. 15 is a side elevational view, partially in section, of a flexible shaft of the electro-mechanical surgical device according to one example embodiment of the present invention.
Figure 16:
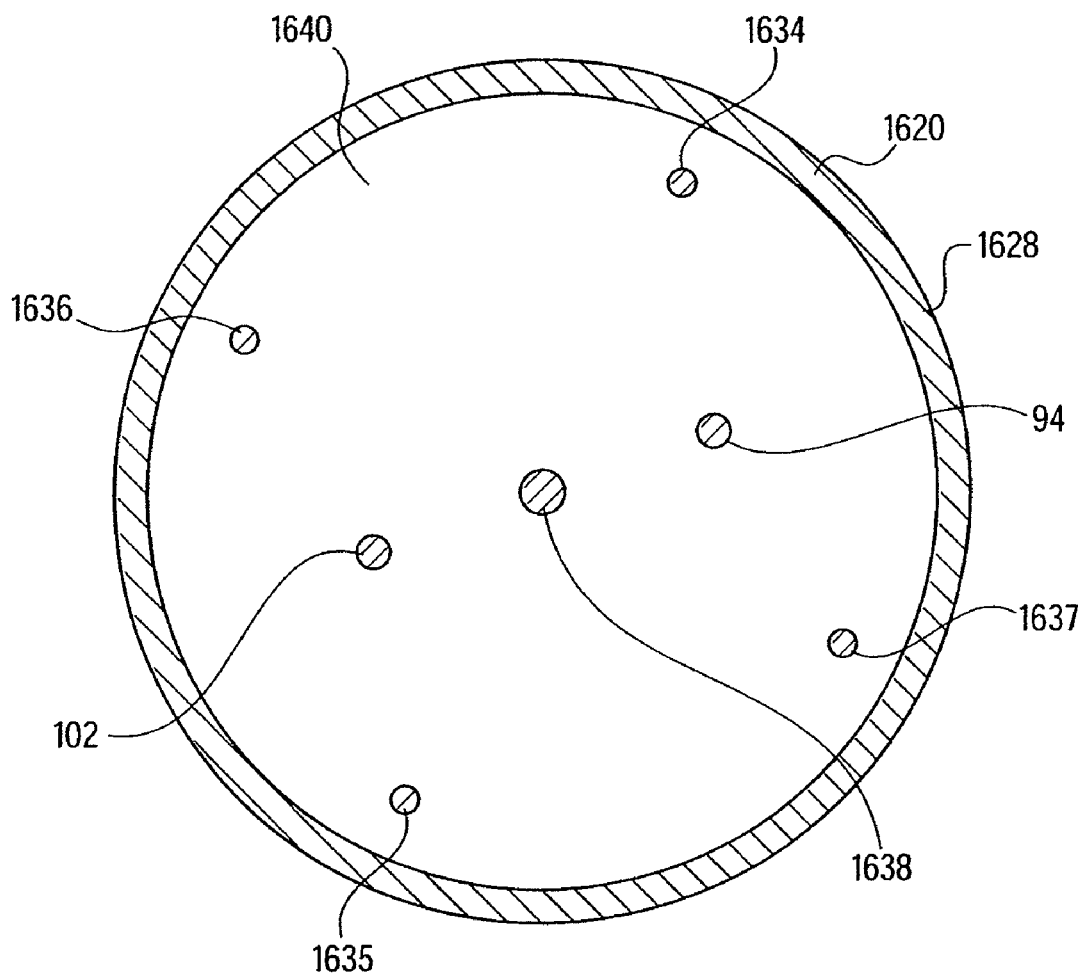
FIG. 16 is a cross-sectional view of the flexible shaft taken along the line 16-16 shown in FIG. 15.

Referring to FIG. 15, there is seen a side view, partially in section, of the flexible shaft 1620. According to one example embodiment, the flexible shaft 1620 includes a tubular sheath 1628, which may include a coating or other sealing arrangement configured to provide a fluid-tight seal between the interior channel 1640 thereof and the environment. The sheath 1628 may be formed of a tissue-compatible, sterilizable elastomeric material. The sheath 1628 may also be formed of a material that is autoclavable. Disposed within the interior channel 1640 of the flexible shaft 1620, and extending along the entire length thereof, may be a first rotatable drive shaft 94, a second rotatable drive shaft 102, a first steering cable 1634, a second steering cable 1635, a third steering cable 1636, a fourth steering cable 1637 and a data transfer cable 1638. FIG. 16 is a cross-sectional view of the flexible shaft 1620 taken along the line 16-16 illustrated in FIG. 15 and further illustrates the several cables 94, 102, 1634, 1635, 1636, 1637 and 1638. Each distal end of the steering cables 1634, 1635, 1636, 1637 is affixed to the distal end 1624 of the flexible shaft 1620. Each of the several cables 94, 102, 1634, 1635, 1636, 1637, 1638 may be contained within a respective sheath.

The first rotatable drive shaft 94 and the second rotatable drive shaft 102 may be configured, for example, as highly flexible drive shafts, such as, for example, braided or helical drive cables. It should be understood that such highly flexible drive cables may have limited torque transmission characteristics and capabilities. It should also be understood that the surgical device 11, or other attachments connected to the flexible shaft 1620, may require a higher torque input than the torque transmittable by the drive shafts 94, 102. The drive shafts 94, 102 may thus be configured to transmit low torque but high speed, the high-speed/low-torque being converted to low-speed/high-torque by gearing arrangements disposed, for example, at the distal end and/or the proximal end of the drive flexible shaft 1620, in the surgical instrument or attachment and/or in the remote power console 1612. It should be appreciated that such gearing arrangement(s) may be provided at any suitable location along the power train between the motors disposed in the housing 1614 and the attached surgical instrument or other attachment connected to the flexible shaft 1620. Such gearing arrangement(s) may include, for example, a spur gear arrangement, a planetary gear arrangement, a harmonic gear arrangement, cycloidal drive arrangement, an epicyclic gear arrangement, etc.

Figure 17:
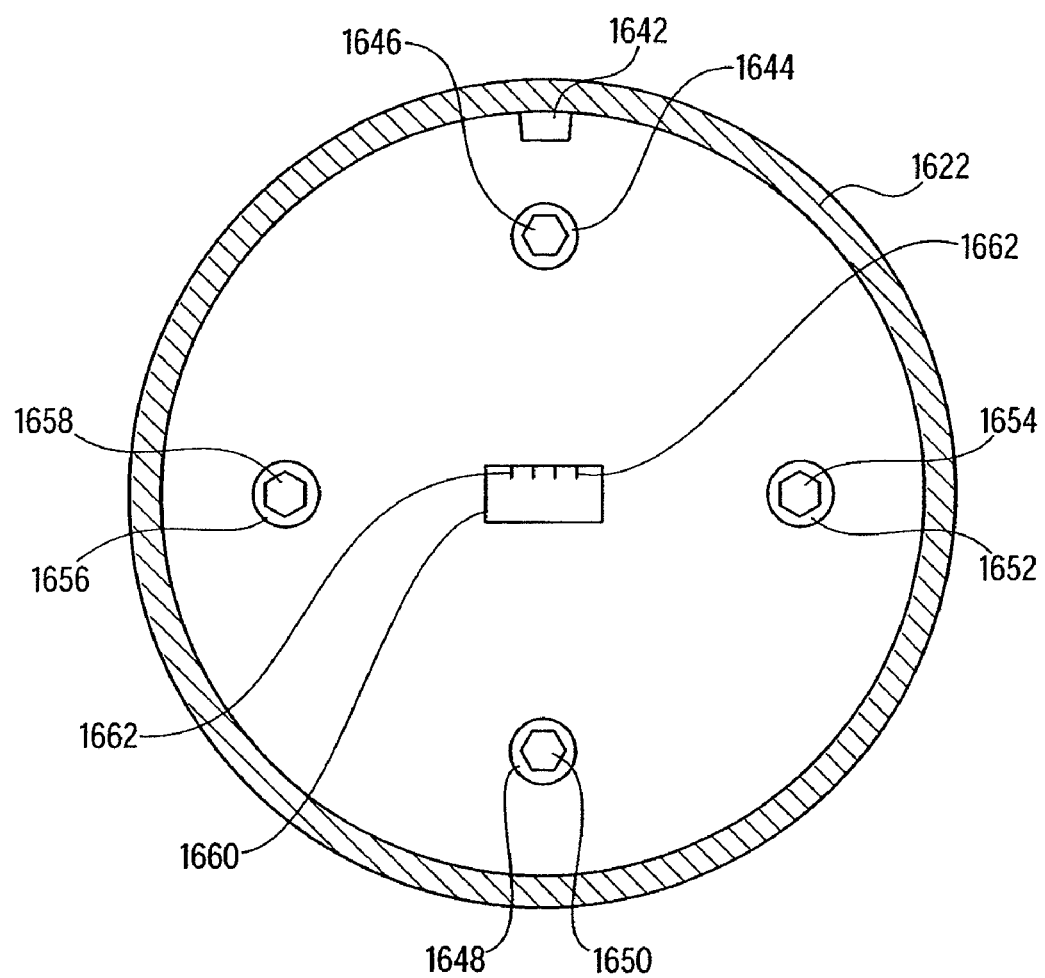
FIG. 17 is a rear end view of a first coupling of the flexible shaft illustrated in FIG. 15.

Referring now to FIG. 17, there is seen a rear end view of first coupling 1622. The first coupling 1622 includes a first connector 1644, a second connector 1648, a third connector 1652 and a fourth connector 1656, each rotatably secured to the first coupling 1622. Each of the connectors 1644, 1648, 1652, 1656 includes a respective recess 1646, 1650, 1654, 1658. As illustrated in FIG. 17, each recess 1646, 1650, 1654, 1658 may be hexagonally shaped. It should be appreciated, however, that the recesses 1646, 1650, 1654, 1658 may have any shape and configuration adapted to non-rotatably couple and rigidly attach the connectors 1644, 1648, 1652, 1656 to respective drive shafts of the motor arrangement contained within the housing 1612. It should be appreciated that complementary projections may be provided on respective drive shafts of the motor arrangement to thereby drive the drive elements of the flexible shaft 1620. It should also be appreciated that the recesses may be provided on the drive shafts and complementary projections may be provided on the connectors 1644, 1648, 1652, 1656. Any other coupling arrangement configured to non-rotatably and releasably couple the connectors 1644, 1648, 1652, 1656 and the drive shafts of the motor arrangement may be provided.

One of the connectors 1644, 1648, 1652, 1656 is non-rotatably secured to the first drive shaft 94, and another one of the connectors 1644, 1648, 1652, 1656 is non-rotatably secured to the second drive shaft 102. The remaining two of the connectors 1644, 1648, 1652, 1656 engage with transmission elements configured to apply tensile forces on the steering cables 1634, 1635, 1636, 1637 to thereby steer the distal end 1624 of the flexible shaft 1620. The data transfer cable 1638 is electrically and logically connected with data connector 1660. The data connector 1660 includes, for example, electrical contacts 1662, corresponding to and equal in number to the number of individual wires contained in the data cable 1638. The first coupling 1622 includes a key structure 1642 configured to properly orient the first coupling 1622 to a mating and complementary coupling arrangement disposed on the housing 1612. The key structure 1642 may be provided on either one, or both, of the first coupling 1622 and the mating and complementary coupling arrangement disposed on the housing 1612. The first coupling 1622 may include a quick-connect type connector, which may engage the first coupling 1622 to the housing 1612 by a simple pushing motion. Seals may be provided in conjunction with any of the several connectors 1644, 1648, 1652, 1656, 1660 to provide a fluid-tight seal between the interior of first coupling 1622 and the environment.

Figure 18:
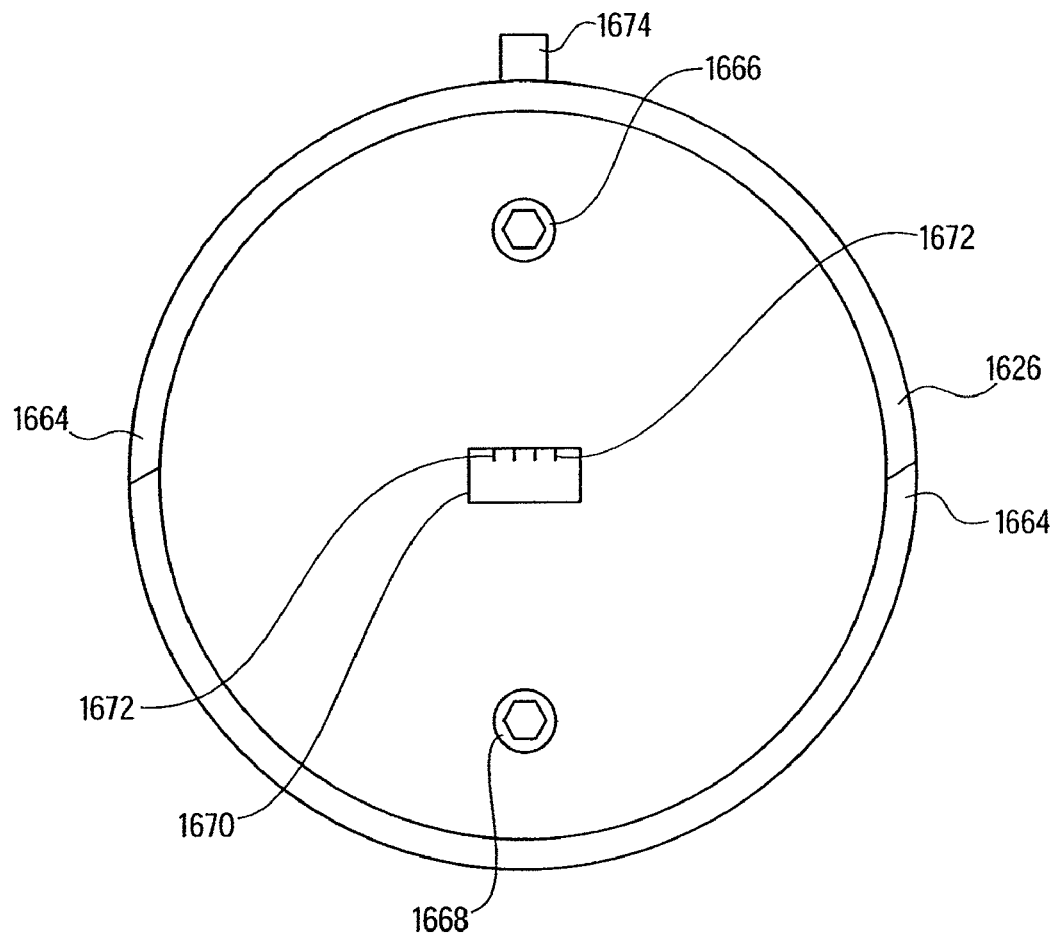
FIG. 18 is a front end view of a second coupling of the flexible shaft illustrated in FIG. 15.

Referring now to FIG. 18, there is seen a front end view of the second coupling 1626 of the flexible shaft 1620. In the example embodiment, the second coupling 1626 includes a first connector 1666 and a second connector 1668, each rotatably secured to the second coupling 1626 and each non-rotatably secured to a distal end of a respective one of the first and second drive shafts 94, 102. A quick-connect type fitting 1664 is provided on the second coupling 1626 to detachably secure the device 11 thereto. The quick-connect type fitting 1664 may be, for example, a rotary quick-connect type fitting, a bayonet type fitting, etc. and may be a fitting complementary to the quick connect sleeve 713 of the keyplate assembly 710 illustrated in FIG. 6(b). A key structure 1674 may be provided on the second coupling 1626 and may be configured to properly align the surgical device 11 to the second coupling 1626. The key structure or other arrangement configured to properly align the surgical device 11 to the flexible shaft 1620 may be provided on either one, or both, of the second coupling 1626 and the surgical device 11. In addition, the key structure may be provided on the device 11, as illustrated in FIG. 6(b) as the slots 713a of the quick connect sleeve 713. A data connector 1670 having electrical contacts 1672 is also provided in the second coupling 1626. Like the data connector 1660 of first coupling 1622, the data connector 1670 of the second coupling 1626 includes contacts 1672 electrically and logically connected to the respective wires of the data transfer cable 1638 and the contacts 1662 of the data connector 1660. Seals may be provided in conjunction with the connectors 1666, 1668, 1670 to provide a fluid-tight seal between the interior of the second coupling 1626 and the environment.

Disposed within the housing 1614 of the remote power console 1612 are electro-mechanical driver elements configured to drive the drive shafts 94, 102 and the steering cables 1634, 1635, 1636, 1637 to thereby operate the electro-mechanical driver component 1610 and the surgical device 11 attached to the second coupling 1626. In the example embodiment illustrated schematically in FIG. 19, five electric motors 96, 100, 1684, 1690, 1696, each operated via a power source, may be disposed in the remote power console 1612. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 19:
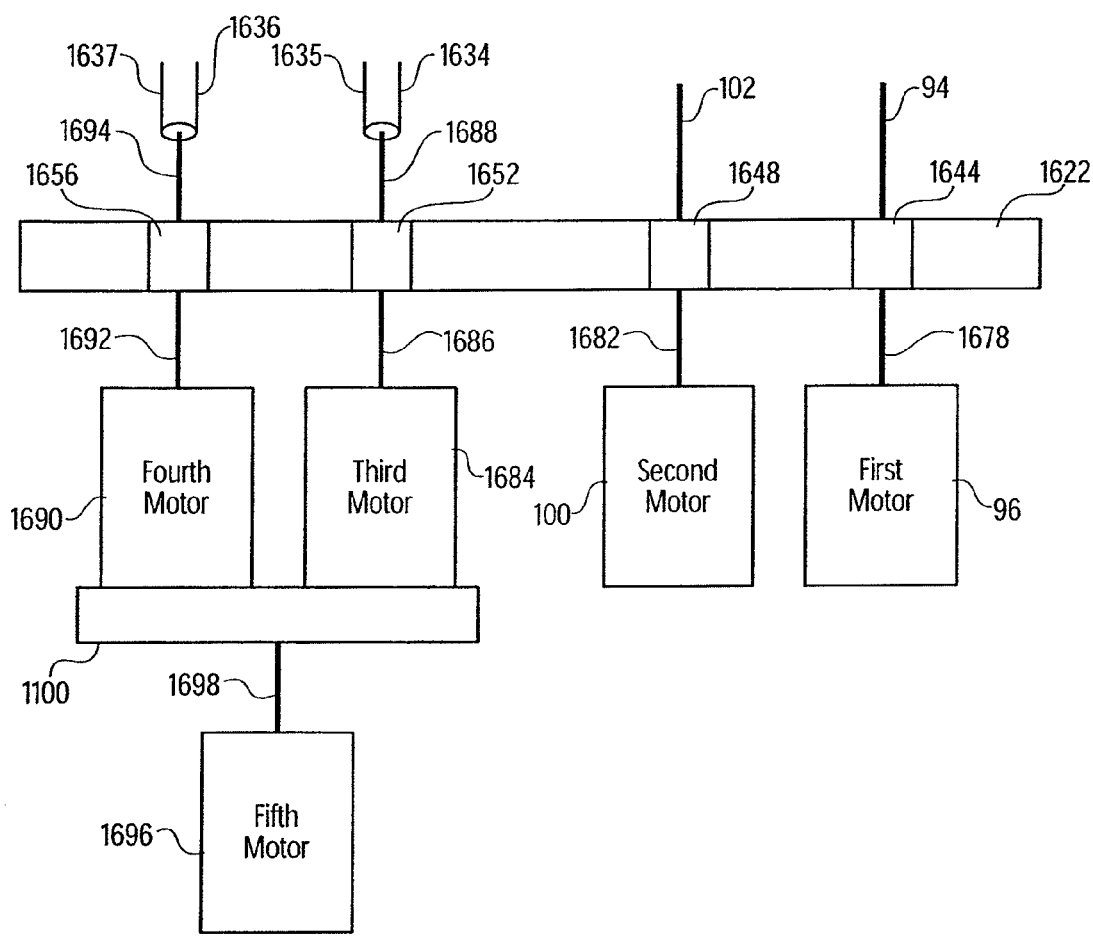
FIG. 19 is a schematic view illustrating a motor arrangement of the electro-mechanical surgical device illustrated in FIG. 2.

FIG. 19 illustrates schematically one possible arrangement of motors. An output shaft 1678 of a first motor 96 engages with the first connector 1644 of the first coupling 1622 when the first coupling 1622, and, therefore, the flexible shaft 1620, is engaged with the housing 1614 to thereby drive the first drive shaft 94 and the first connector 1666 of the second coupling 1626. Similarly, an output shaft 1682 of a second motor 100 engages the second connector 1648 of the first coupling 1622 when the first coupling 1622, and, therefore, flexible shaft 1620 is engaged with the housing 1614 to thereby drive the second drive shaft 102 and the second connector 1668 of the second coupling 1626. An output shaft 1686 of a third motor 1684 engages the third connector 1652 of the first coupling 1622 when the first coupling 1622, and, therefore, the flexible shaft 1620, is engaged with the housing 1614 to thereby drive the first and second steering cables 1634, 1635 via a first pulley arrangement 1688. An output shaft 1692 of a fourth motor 1690 engages the fourth connector 1656 of the first coupling 1622 when the first coupling 1622, and, therefore, the flexible shaft 1620, is engaged with the housing 1614 to thereby drive the third and fourth steering cables 1636, 1637 via a second pulley arrangement 1694. The third and fourth motors 1684, 1690 may be secured on a carriage 1100, which is selectively movable via an output shaft 1698 of a fifth motor 1696 between a first position and a second position to selectively engage and disengage the third and fourth motors 1684, 1690 with the respective pulley arrangement 1688, 1694 to thereby permit the flexible shaft 1620 to become taut and steerable or limp as necessary. It should be appreciated that other mechanical, electrical and/or electro-mechanical mechanisms, etc., may be used to selectively engage and disengage the steering mechanism. The motors may be arranged and configured as described, for example, in U.S. patent application Ser. No. 09/510,923, entitled "A Carriage Assembly for Controlling a Steering Wire Mechanism Within a Flexible Shaft," which is expressly incorporated herein in its entirety by reference thereto.

It should be appreciated that any one or more of the motors 96, 100, 1684, 1690, 1696 may be, for example, a high-speed/low-torque motor, a low-speed/high-torque motor, etc. As indicated above, the first rotatable drive shaft 94 and the second rotatable drive shaft 102 may be configured to transmit high speed and low torque. Thus, the first motor 96 and the second motor 100 may be configured as high-speed/low-torque motors. Alternatively, the first motor 96 and the second motor 100 may be configured as low-speed/high-torque motors with a torque-reducing/speed-increasing gear arrangement disposed between the first motor 96 and the second motor 100 and a respective one of the first rotatable drive shaft 94 and the second rotatable drive shaft 102. Such torque-reducing/speed-increasing gear arrangements may include, for example, a spur gear arrangement, a planetary gear arrangement, a harmonic gear arrangement, cycloidal drive arrangement, an epicyclic gear arrangement, etc. It should be appreciated that any such gear arrangement may be disposed within the remote power console 1612 or in the proximal end of the flexible shaft 1620, such as, for example, in the first coupling 1622. It should be appreciated that the gear arrangement(s) may be provided at the distal and/or proximal ends of the first rotatable drive shaft 94 and/or the second rotatable drive shaft 102 to prevent windup and breakage thereof.

Figure 20:
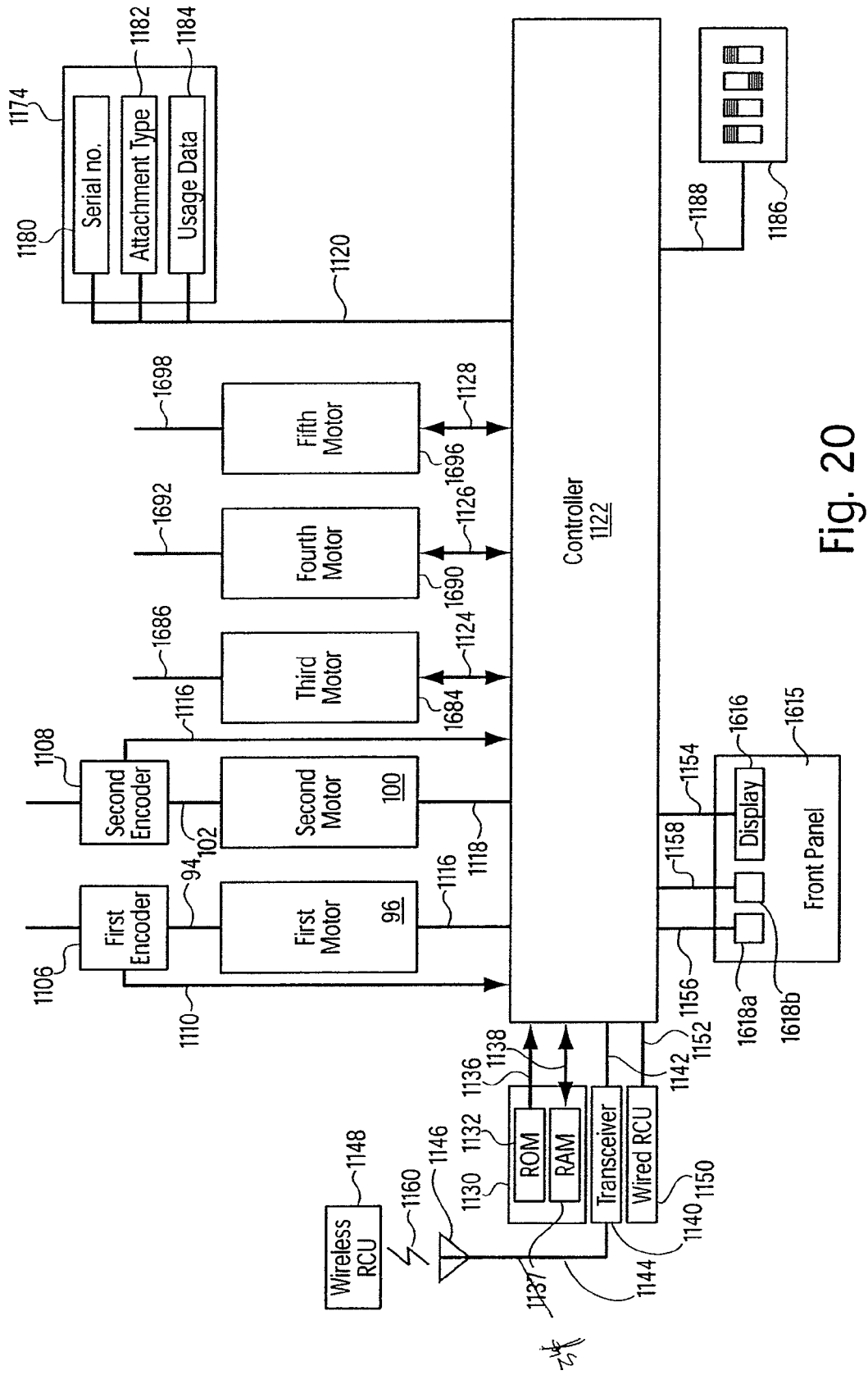
FIG. 20 is a schematic view of the electro-mechanical surgical device illustrated in FIG. 2.

Referring now to FIG. 20, there is seen a schematic view of the electro-mechanical driver component 1610. A controller 1122 is provided in the housing 1614 of remote power console 1612 and is configured to control all functions and operations of the electro-mechanical driver component 1610 and the linear clamping, cutting and stapling device 11 or other surgical instrument or attachment attached to the flexible shaft 1620. A memory unit 1130 is provided and may include memory devices, such as, a ROM component 1132, a RAM component 1134, etc. The ROM component 1132 is in electrical and logical communication with the controller 1122 via a line 1136, and the RAM component 1134 is in electrical and logical communication with controller 1122 via line 1138. The RAM component 1134 may include any type of random-access memory, such as, for example, a magnetic memory device, an optical memory device, a magneto-optical memory device, an electronic memory device, etc. Similarly, the ROM component 1132 may include any type of read-only memory, such as, for example, a removable memory device, such as a PC-Card or PCMCIA-type device. It should be appreciated that the ROM component 1132 and the RAM component 1134 may be configured as a single unit or may be separate units and that the ROM component 1132 and/or the RAM component 1134 may be provided in the form of a PC-Card or PCMCIA-type device.

The controller 1122 is further connected to the front panel 1615 of the housing 1614 and, more particularly, to the display device 1616 via a line 1154 and the indicators 1618a, 1618b via respective lines 1156, 1158. The lines 1116, 1118, 1124, 1126, 1128 electrically and logically connect controller 1122 to first, second, third, fourth and fifth motors 96, 100, 1684, 1690, 1696, respectively. A wired remote control unit ("RCU") 1150 is electrically and logically connected to the controller 1122 via a line 1152. A wireless RCU 1148 is also provided and communicates via a wireless link 1160 with a receiving/sending unit 1146 connected via a line 1144 to a transceiver 1140. The transceiver 1140 is electrically and logically connected to the controller 1122 via a line 1142. The wireless link 1160 may be, for example, an optical link, such as an infrared link, a radio link or any other form of wireless communication link.

A switch device 1186, which may include, for example, an array of DIP switches, may be connected to the controller 1122 via a line 1188. The switch device 1186 may be configured, for example, to select one of a plurality of languages used in displaying messages and prompts on the display device 1616. The messages and prompts may relate to, for example, the operation and/or the status of the electro-mechanical driver component 1610 and/or to the surgical device 11 attached thereto.

According to the example embodiment of the present invention, a first encoder 1106 is provided within the second coupling 1626 and is configured to output a signal in response to and in accordance with the rotation of the first drive shaft 94. A second encoder 1108 is also provided within the second coupling 626 and is configured to output a signal in response to and in accordance with the rotation of the second drive shaft 102. The signal output by each of the encoders 1106, 1108 may represent the rotational position of the respective drive shaft 94, 102 as well as the rotational direction thereof. Such encoders 1106, 1108 may include, for example, Hall-effect devices, optical devices, etc. Although the encoders 1106, 1108 are described as being disposed within the second coupling 1626, it should be appreciated that the encoders 1106, 1108 may be provided at any location between the motor system and the surgical device 11. It should be appreciated that providing the encoders 1106, 1108 within the second coupling 1626 or at the distal end of the flexible shaft 1620 may provide an accurate determination of the drive shaft rotation. If the encoders 1106, 1108 are disposed at the proximal end of the flexible shaft 1620, windup of the first and second rotatable drive shafts 94, 102 may result in measurement error.

Figure 21:
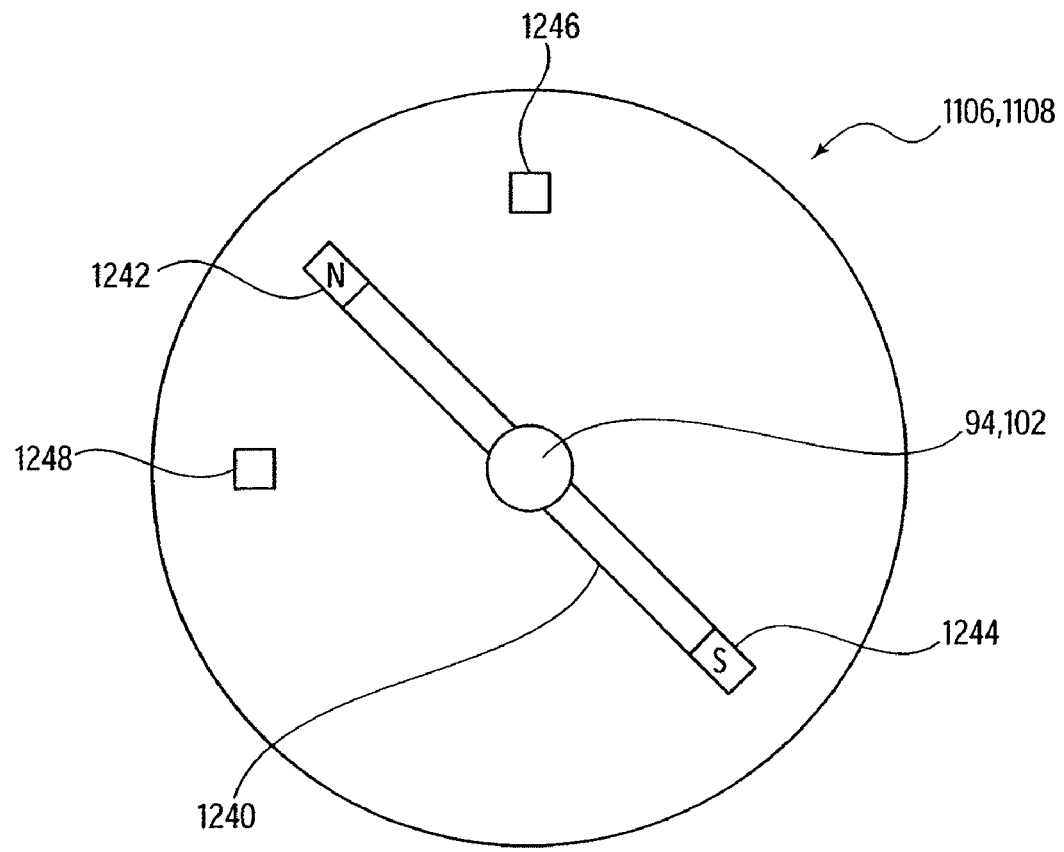
FIG. 21 is a schematic view of an encoder of the flexible shaft illustrated in FIG. 15.

FIG. 21 is a schematic view of an encoder 1106, 1108, which includes a Hall-effect device. Mounted non-rotatably on the drive shaft 94, 102 is a magnet 1240 having a north pole 1242 and a south pole 1244. The encoder 1106, 1108 further includes a first sensor 1246 and second sensor 1248, which are disposed approximately 90° apart relative to the longitudinal, or rotational, axis of the drive shaft 94, 102. The output of the sensors 1246, 1248 is persistent and changes its state as a function of a change of polarity of the magnetic field in the detection range of the sensor. Thus, based on the output signal from the encoders 1106, 1108, the angular position of the drive shaft 94, 102 may be determined within one-quarter revolution and the direction of rotation of the drive shaft 94, 102 may be determined. The output of each encoder 1106, 1108 is transmitted via a respective line 1110, 1112 of data transfer cable 1638 to controller 1122. The controller 1122, by tracking the angular position and rotational direction of the drive shafts 94, 102 based on the output signal from the encoders 1106, 1108, may thereby determine the position and/or state of the components of the surgical device connected to the electro-mechanical driver component 1610. That is, by counting the revolutions of the drive shaft 94, 102, the controller 1122 may determine the position and/or state of the components of the surgical device connected to the electro-mechanical driver component 1610.

For example, the advancement distance of the first jaw 50 relative to the second jaw 80 and of the wedge 603 may be functions of, and ascertainable on the basis of, the rotation of the respective drive shafts 94, 102. By ascertaining an absolute position of the first jaw 50 and the wedge 603 at a point in time, the relative displacement of the first jaw 50 and the wedge 603, based on the output signal from the encoders 1106, 1108 and the known pitches of the externally threaded rod 90 and of the wedge driver 605, may be used to ascertain the absolute position of the first jaw 50 and the wedge 603 at all times thereafter. The absolute position of the first jaw 50 and the wedge 603 may be fixed and ascertained at the time that the surgical device 11 is first coupled to the flexible shaft 1620. Alternatively, the position of the first jaw 50 and the wedge 603 relative to, for example, the second jaw 80 may be determined based on the output signal from the encoders 1106, 1108.

As discussed above in connection with FIG. 7, the surgical device 11 may include a data connector 1272 adapted by size and configuration to electrically and logically connect to connector 1670 of second coupling 1626. In the example embodiment, the data connector 1272 includes contacts 1276 equal in number to the number of contacts 1672 of connector 1670. The memory module 6041 is electrically and logically connected with the data connector 1272. Memory module 6041 may be in the form of, for example, an EEPROM, EPROM, etc. and may be contained, for example, within the staple tray 604 of the replaceable staple cartridge 600 in the second jaw 80 of the surgical device 11, as illustrated in FIG. 6(a).

Figure 22:
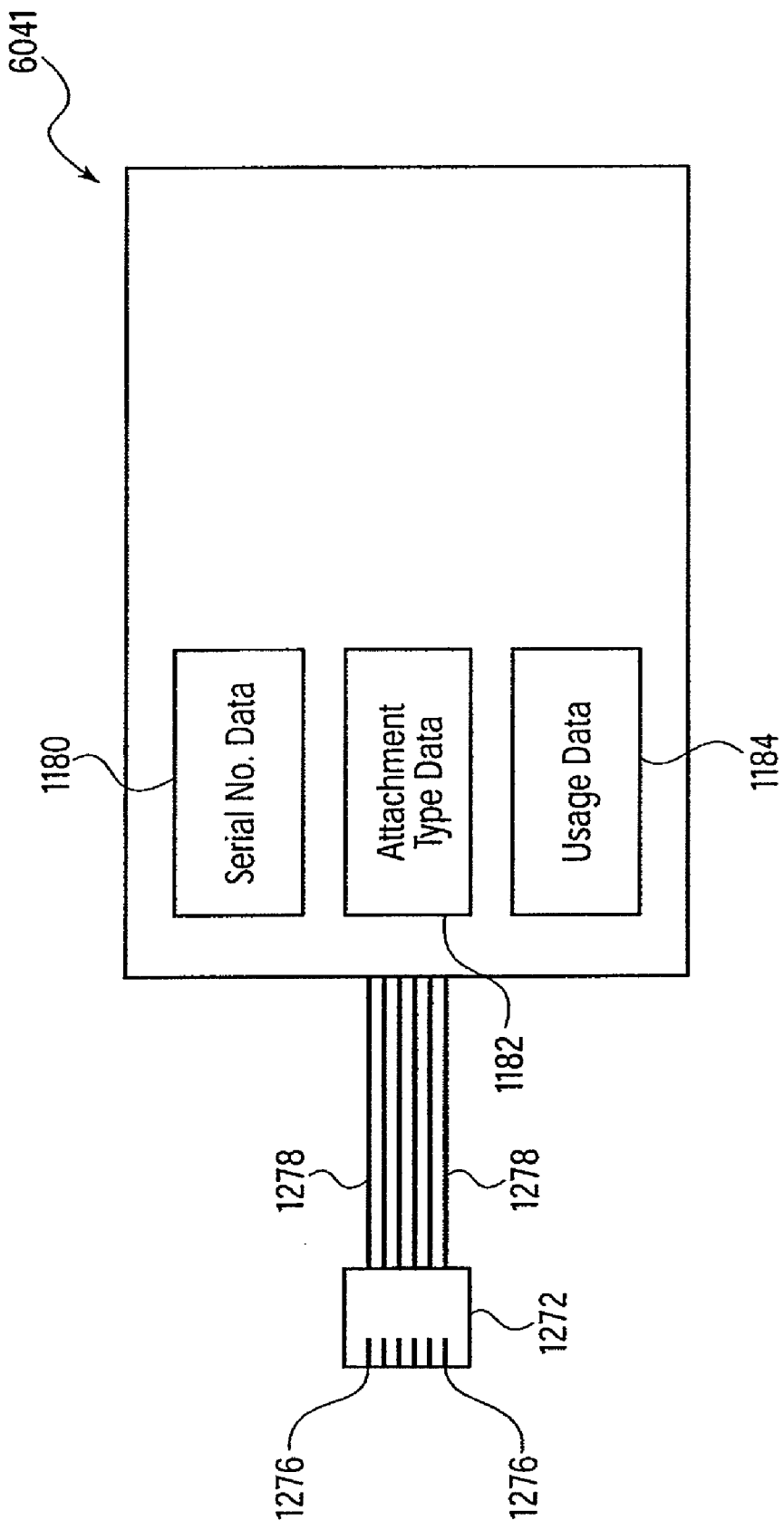
FIG. 22 is a schematic view of a memory device of a linear clamping, cutting and stapling device according to one example embodiment of the present invention.

FIG. 22 schematically illustrates the memory module 6041. As seen in FIG. 22, data connector 1272 includes contacts 1276, each electrically and logically connected to the memory module 6041 via a respective line, e.g., flexible data cable 1278. The memory module 6041 may be configured to store, for example, a serial number data 1180, an attachment type identifier (ID) data 1182 and a usage data 1184. The memory module 6041 may additionally store other data. Both the serial number data 1180 and the ID data 1182 may be configured as read-only data. The serial number data 1180 and/or the ID data 1182 may be stored in a read-only section of the memory module 6041. In the example embodiment, serial number data 1180 may be data uniquely identifying the particular surgical device, whereas the ID data 1182 may be data identifying the type of the attachment, such as, e.g., for an electro-mechanical driver component 1610 to which other types of surgical instruments or attachments are attachable. The usage data 1184 represents usage of the particular attachment, such as, for example, the number of times the first jaw 50 of the surgical device 11 has been opened and closed, or the number of times that the wedge 603 of the surgical device 11 has been advanced. The usage data 1184 may be stored in a read/write section of the memory module 6041.

It should be appreciated that the attachment attachable to the distal end 1624 of the flexible shaft 1620, e.g., surgical device 11, may be designed and configured to be used a single time or multiple times. The attachment may also be designed and configured to be used a predetermined number of times. Accordingly, the usage data 1184 may be used to determine whether the surgical device 11 has been used and whether the number of uses has exceeded the maximum number of permitted uses. As more fully described below, an attempt to use the attachment after the maximum number of permitted uses has been reached will generate an ERROR condition.

Referring again to FIG. 20, the controller 1122 is configured to read the ID data 1182 from the memory module 6041 of the surgical device 11 when the surgical device 11 is initially connected to the flexible shaft 1620. The memory module 6041 is electrically and logically connected to the controller 1122 via the line 1120 of the data transfer cable 1638. Based on the read ID data 1182, the controller 1122 is configured to read or select from the memory unit 1130, an operating program or algorithm corresponding to the type of surgical instrument or attachment connected to the flexible shaft 1620. The memory unit 1130 is configured to store the operating programs or algorithms for each available type of surgical instrument or attachment, the controller 1122 selecting and/or reading the operating program or algorithm from the memory unit 1130 in accordance with the ID data 1182 read from the memory module 6041 of an attached surgical instrument or attachment. As indicated above, the memory unit 1130 may include a removable ROM component 1132 and/or RAM component 1134. Thus, the operating programs or algorithms stored in the memory unit 1130 may be updated, added, deleted, improved or otherwise revised as necessary. The operating programs or algorithms stored in the memory unit 1130 may be customizable based on, for example, specialized needs of the user. A data entry device, such as, for example, a keyboard, a mouse, a pointing device, a touch screen, etc., may be connected to the memory unit 1130 via, for example, a data connector port, to facilitate the customization of the operating programs or algorithms. Alternatively or additionally, the operating programs or algorithms may be customized and preprogrammed into the memory unit 1130 remotely from the electro-mechanical driver component 1610. It should be appreciated that the serial number data 1180 and/or usage data 1184 may also be used to determine which of a plurality of operating programs or algorithms is read or selected from the memory unit 1130. It should be appreciated that the operating program or algorithm may alternatively be stored in the memory module 6041 of the surgical device 11 and transferred to the controller 1122 via the data transfer cable 1638. Once the appropriate operating program or algorithm is read by or selected by or transmitted to, the controller 1122, the controller 1122 causes the operating program or algorithm to be executed in accordance with operations performed by the user via the wired RCU 1150 and/or the wireless RCU 1148. As indicated hereinabove, the controller 1122 is electrically and logically connected with the first, second, third, fourth and fifth motors 96, 100, 1684, 1690, 1696 via respective lines 1116, 1118, 1124, 1126, 1128 and is configured to control such motors 96, 100, 1684, 1690, 1696 in accordance with the read, selected or transmitted operating program or algorithm via the respective lines 1116, 1118, 1124, 1126, 1128.

Figure 23:
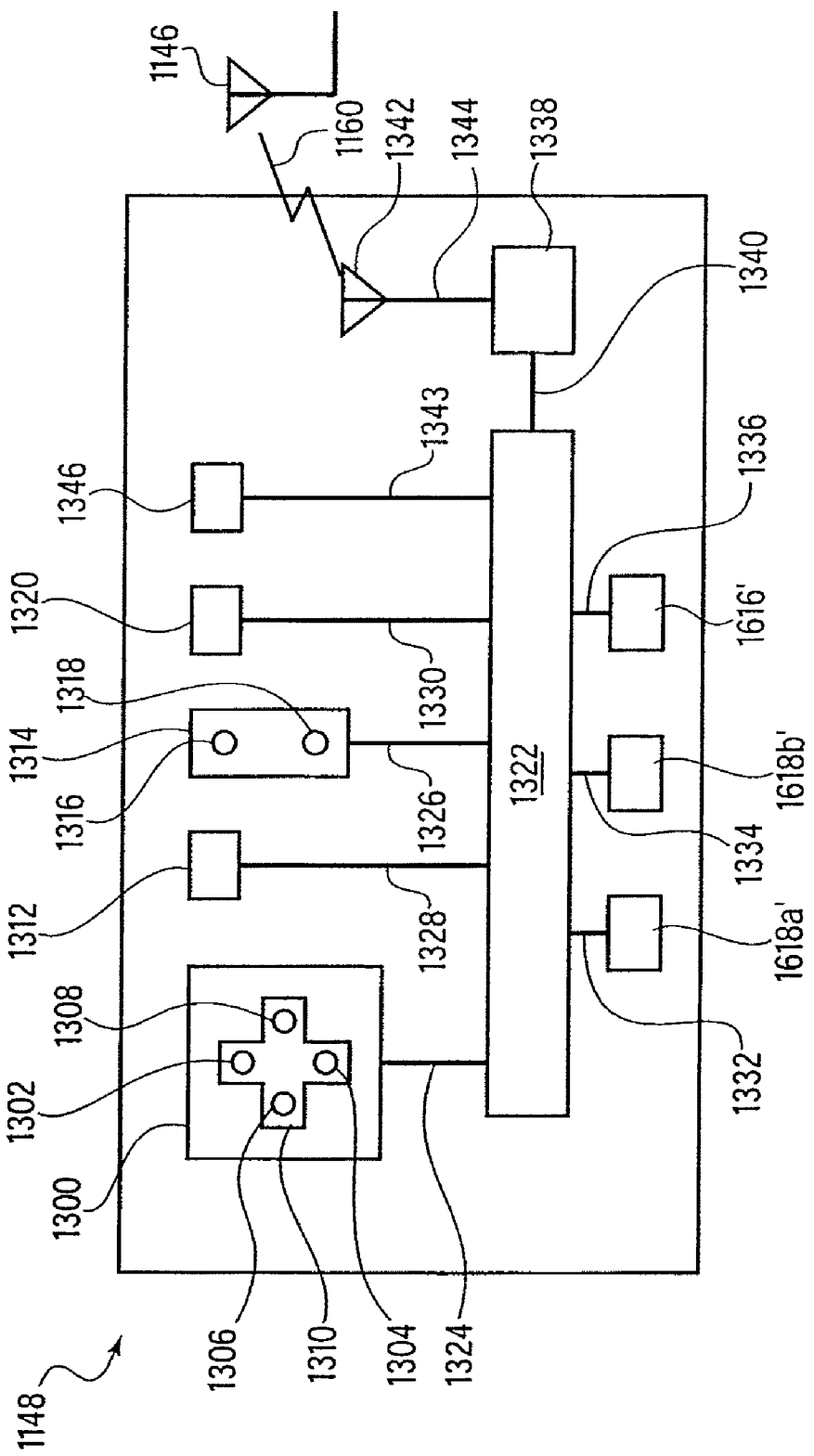
FIG. 23 is a schematic view of a wireless remote control unit of the electro-mechanical surgical device illustrated in FIG. 2.

Referring now to FIG. 23, there is seen a schematic view of wireless RCU 1148. Wireless RCU 1148 includes a steering controller 1300 having a plurality of switches 1302, 1304, 1306, 1308 arranged under a four-way rocker 1310. The operation of switches 1302, 1304, via rocker 1310, controls the operation of first and second steering cables 1634, 1635 via third motor 1684. Similarly, the operation of switches 1306, 1308, via rocker 1310, controls the operation of third and fourth steering cables 1636, 1637 via fourth motor 1692. It should be appreciated that rocker 1310 and switches 1302, 1304, 1306, 1308 are arranged so that the operation of switches 1302, 1304 steers the flexible shaft 1620 in the north-south direction and that the operation of switches 1306, 1308 steers the flexible shaft 1620 in the east-west direction. Reference herein to north, south, east and west is made to a relative coordinate system. Alternatively, a digital joystick, an analog joystick, etc. may be provided in place of rocker 1310 and switches 1302, 1304, 1306, 1308. Potentiometers or any other type of actuator may also be used in place of switches 1302, 1304, 1306, 1308.

The wireless RCU 1148 further includes a steering engage/disengage switch 1312, the operation of which controls the operation of fifth motor 696 to selectively engage and disengage the steering mechanism. The wireless RCU 1148 also includes a two-way rocker 1314 having first and second switches 1316, 1318 operable thereby. The operation of these switches 1316, 1318 controls certain functions of the electromechanical driver component 1610 and any surgical instrument or attachment, such as the surgical device 11, attached to the flexible shaft 1620 in accordance with the operating program or algorithm corresponding to the attached device. For example, operation of the two-way rocker 1314 may control the opening and closing of the first jaw 50 and the second jaw 80 of the surgical device 11. The wireless RCU 1148 is provided with yet another switch 1320, the operation of which may further control the operation of the electro-mechanical driver component 1610 and the device attached to the flexible shaft 1620 in accordance with the operating program or algorithm corresponding to the attached device. For example, operation of the switch 1320 may initiate the advancement of the wedge 603 of the surgical device 11.

The wireless RCU 1148 includes a controller 1322, which is electrically and logically connected with the switches 1302, 1304, 1306, 1308 via line 1324, with the switches 1316, 1318 via line 1326, with switch 1312 via line 1328 and with switch 1320 via line 1330. The wireless RCU 1148 may include indicators 1618a', 1618b', corresponding to the indicators 1618a, 1618b of front panel 1615, and a display device 1616', corresponding to the display device 1616 of the front panel 1615. If provided, the indicators 1618a', 1618b' are electrically and logically connected to controller 1322 via respective lines 1332, 1334, and the display device 1616' is electrically and logically connected to controller 1322 via line 1336. The controller 1322 is electrically and logically connected to a transceiver 1338 via line 1340, and the transceiver 1338 is electrically and logically connected to a receiver/transmitter 1342 via line 1344. A power supply, for example, a battery, may be provided in wireless RCU 1148 to power the same. Thus, the wireless RCU 1148 may be used to control the operation of the electro-mechanical driver component 1610 and the device 11 attached to the flexible shaft 1620 via wireless link 1160.

The wireless RCU 1148 may include a switch 1346 connected to a controller 1322 via line 1348. Operation of the switch 1346 transmits a data signal to the transmitter/receiver 1146 via wireless link 1160. The data signal includes identification data uniquely identifying the wireless RCU 1148. This identification data is used by the controller 1122 to prevent unauthorized operation of the electro-mechanical driver component 1610 and to prevent interference with the operation of the electro-mechanical driver component 610 by another wireless RCU. Each subsequent communication between the wireless RCU 1148 and the electro-mechanical device surgical 610 may include the identification data. Thus, the controller 1122 may discriminate between wireless RCUs and thereby allow only a single, identifiable wireless RCU 1148 to control the operation of the electro-mechanical driver component 1610 and the surgical device 11 attached to the flexible shaft 1620.

Based on the positions of the components of the surgical device attached to the flexible shaft 1620, as determined in accordance with the output signals from the encoders 1106, 1108, the controller 1122 may selectively enable or disable the functions of the electro-mechanical driver component 1610 as defined by the operating program or algorithm corresponding to the attached device. For example, for the surgical device 11, the firing function controlled by the operation of the switch 1320 may be disabled unless the space or gap between the first jaw 50 and the second jaw 80 is determined to be within an acceptable range.

Figure 24:
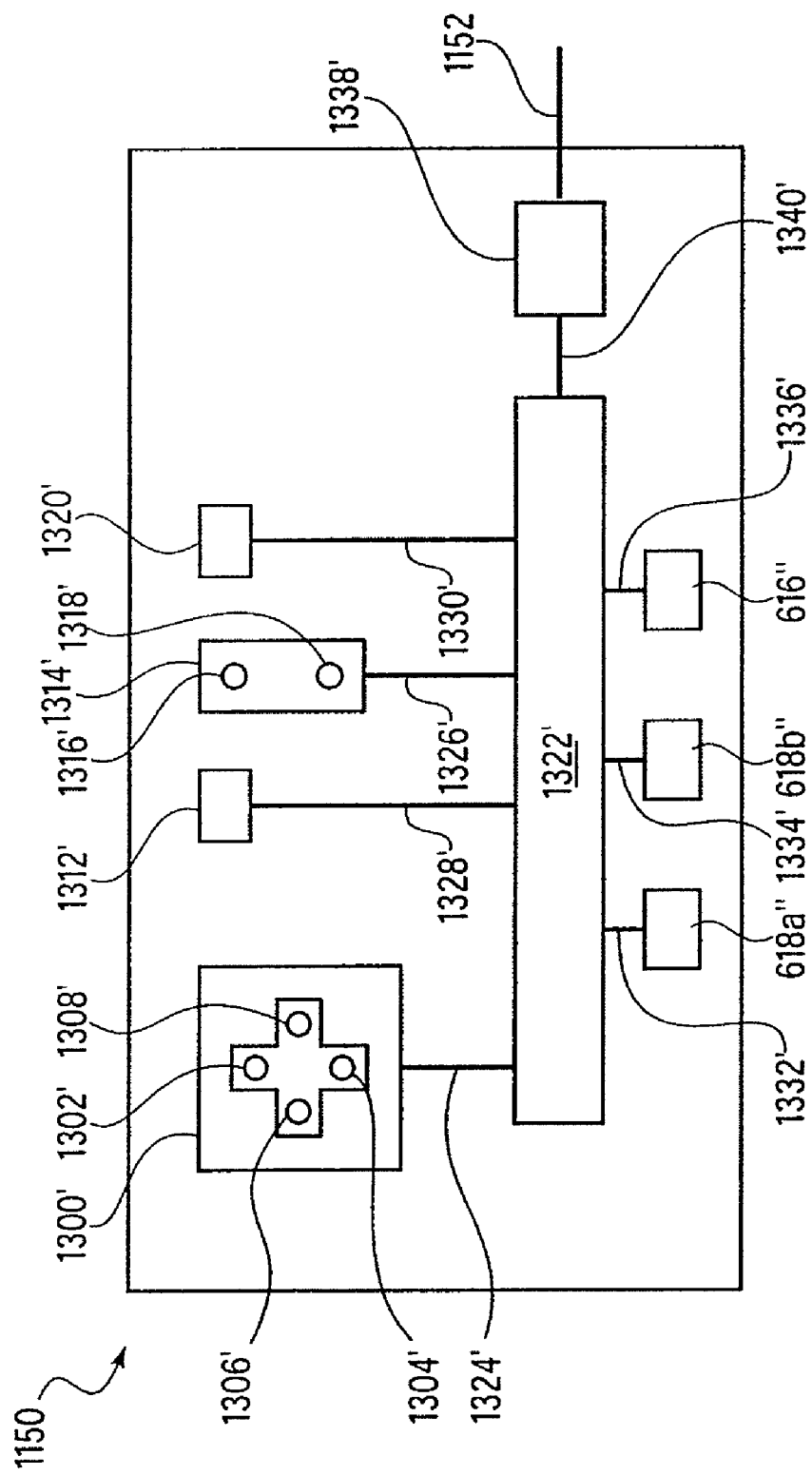
FIG. 24 is a schematic view of a wired remote control unit of the electro-mechanical surgical device illustrated in FIG. 2.

Referring now to FIG. 24, there is seen a schematic view of a wired RCU 1150. In the example embodiment, wired RCU 1150 includes substantially the same control elements as the wireless RCU 1148 and further description of such elements is omitted. Like elements are indicated in FIG. 24 with an accompanying prime. It should be appreciated that the functions of the electro-mechanical driver component 1610 and the device attached to the flexible shaft 1620, e.g., the surgical device 11, may be controlled by the wired RCU 1150 and/or by the wireless RCU 1148. In the event of a battery failure, for example, in the wireless RCU 1148, the wired RCU 1150 may be used to control the functions of the electro-mechanical driver component 1610 and the device attached to the flexible shaft 1620.

As described hereinabove, the front panel 1615 of the housing 1614 includes the display device 1616 and the indicators 1618a, 1618b. The display device 1616 may include an alpha-numeric display device, such as an LCD display device. The display device 1616 may also include an audio output device, such as a speaker, a buzzer, etc. The display device 1616 is operated and controlled by controller 1122 in accordance with the operating program or algorithm corresponding to the device attached to the flexible shaft 1620, e.g., the surgical device 11. If no surgical instrument or attachment is so attached, a default operating program or algorithm may be read by or selected by or transmitted to controller 1122 to thereby control the operation of the display device 1616 as well as the other aspects and functions of the electro-mechanical driver component 1610. If the surgical device 11 is attached to the flexible shaft 1620, the display device 1616 may display, for example, data indicative of the gap between the first jaw 50 and the second jaw 80 as determined in accordance with the output signal of encoders 1106, 1108, as more fully described hereinabove.

Similarly, the indicators 1618a, 1618b are operated and controlled by the controller 1122 in accordance with the operating program or algorithm corresponding to the device attached to the flexible shaft 1620, e.g., the surgical device 11. The indicator 1618a and/or the indicator 1618b may include an audio output device, such as a speaker, a buzzer, etc., and/or a visual indicator device, such as an LED, a lamp, a light, etc. If the surgical device 11 is attached to the flexible shaft 1620, the indicator 1618a may indicate, for example, that the electro-mechanical driver component 1610 is in a power ON state, and the indicator 618b may, for example, indicate whether the gap between the first jaw 50 and the second jaw 80 is determined to be within the acceptable range. It should be appreciated that although two indicators 1618a, 1618b are described, any number of additional indicators may be provided as necessary. Additionally, it should be appreciated that although a single display device 1616 is described, any number of additional display devices may be provided as necessary.

The display device 1616' and the indicators 1618a', 1618b' of wired RCU 1150 and the display device 1616" and indicators 1618a", 1618b" of the wireless RCU 1148 are similarly operated and controlled by respective controller 1322, 1322' in accordance with the operating program or algorithm of the device attached to the flexible shaft 1620.

As previously mentioned, the surgical device 11 may be employed to clamp, cut and staple a section of tissue. The operation of the surgical device 11 will now be described in connection with the removal of a cancerous or anomalous section of tissue in a patient's bowel, which is, of course, merely one type of tissue and one type of surgery that may be performed using the surgical device 11. Generally, in operation, after cancerous or anomalous section of tissue has been located in the gastrointestinal tract, the surgical device 11, which may initially be maintained in a closed position such as the position illustrated in FIG. 3(a), is inserted into a patient's abdomen, e.g., through a cannula (not shown). Preferably, the surgical device 11 has a staple tray 604 pre-loaded in the second jaw 80. Utilizing the remote actuation provided by the electro-mechanical driver system 1610, the first driver 88 is engaged to drive the first jaw 50 of the surgical device 11 into the open position relative to the second jaw 80. A section of tissue adjacent to the cancerous tissue is placed between the open first and second jaws 50, 80. Again, by remote actuation, the first driver 88 is caused to engage in reverse, and the first jaw 50 closes against the second jaw 80, clamping the section of tissue therebetween. Once the section of tissue has been sufficiently clamped, the second driver 98 is engaged by remote actuation, which causes the wedge 603 to advance from the distal end 604c of the staple tray 604 to the proximal end 604d thereof, thereby cutting and stapling the section of tissue. According to one example embodiment of the present invention, the second driver 98 is then engaged in reverse, which causes the wedge 603 to be retracted from the proximal end 604d to the distal end 604c of the staple tray 604. The surgical device 11 may then be removed from the patient's abdomen. Once removed, the first driver 88 may again be engaged, according to some example embodiments of the present invention, to drive the first jaw 50 of the surgical device 11 into the open position relative to the second jaw 80, enabling the spent replaceable staple cartridge 600 to be removed from the second jaw 80 of the surgical device 11 and a new replaceable staple cartridge 600 to be inserted into the second jaw 80. These steps are then repeated on the other side of the cancerous tissue, thereby removing the cancerous section of tissue, which is stapled on both ends to prevent spilling of bowel material into the abdomen. It is noted however, that alternative embodiments of the present invention are possible, wherein the surgical device 11 and/or the electro-mechanical driver component 1610 are configured to allow only a single use of the surgical device 11, as is described more fully below.

According to the example embodiment of the present invention, the surgical device 11 is coupled to the second coupling 1626 of the electro-mechanical driver component 1610 such that the first drive socket 654 engages the first drive shaft 94 of the electro-mechanical driver component 1610 and the second drive socket 694 engages the second drive shaft 102 of the electro-mechanical driver component 1610. Thus, rotation of the first driver 88 is effected by rotation of the first drive socket 654 which is effected by rotation of the first drive shaft 94 of the electro-mechanical driver component 1610. Clockwise or counter-clockwise rotation is achieved depending on the direction of the first motor 96. Similarly, rotation of the second driver 98 is effected by rotation of the second drive socket 694 which is effected by rotation of the second drive shaft 102 of the electro-mechanical driver component 1610. Again, clockwise or counter-clockwise rotation is achieved depending on the direction of the motor 100.

Once the surgical device 11 is inserted into the body of a patient, the first motor 96 corresponding to the first drive shaft 94 is activated, which engages the first drive socket 654 at the proximal end of the clamp shaft assembly 650, thereby causing the clamp shaft assembly 650 to turn in a first, e.g., clockwise, rotation direction. Since the spur gear teeth 6531 of the spur gear 653 of the clamp shaft assembly 650 are engaged with the spur gear teeth 6441 of the spur gear 644 of the gear cluster 640, the rotation of the clamp shaft assembly 650 causes the gear cluster 640 to rotate in a first direction, e.g., counter-clockwise, that is opposite to the direction of rotation of the clamp shaft assembly 650. Simultaneously, since the spur gear teeth 6431 of the spur gear 643 of the gear cluster 640 is engaged with the spur gear teeth 6291 of the spur gear 629 of the gear cluster 630, the rotation of the gear cluster 640 causes the gear cluster 630 to rotate in a first direction, e.g., clockwise, that is opposite to the direction of rotation of the clamp shaft assembly 640. At the same time, since the spur gear teeth 6331 of the spur gear 633 of the gear cluster 630 engage the spur gear teeth 6271 of the spur gear 627 of the gear cluster 625, and since the spur gear teeth 6341 of the spur gear 634 of the gear cluster 630 engage the spur gear teeth 6281 of the spur gear 628 of the gear cluster 625, the rotation of the gear cluster 630 causes the gear cluster 625 to rotate in a first direction, e.g., counter-clockwise, that is opposite to the direction of rotation of the clamp shaft assembly 630. The rotation of the gear cluster 625 causes the bevel gear 621, which, like the gear cluster 625 is also mounted on the bevel gear driver 620, to rotate in a first direction, e.g., counter-clockwise, that is the same as the direction of rotation of the gear cluster 625. Since the beveled gear teeth 621a of the bevel gear 621 are engaged with the beveled gear teeth 617b of the bevel gear nut 617, the rotation of the bevel gear 621 causes the bevel gear nut 617 to rotate within the bevel bearing 622 in a first, e.g., clockwise when viewed from the top, direction. The threads of the internally-threaded bore 617a of the bevel gear nut 617 engage the threads of the externally-threaded rod 90, such that rotation of the bevel gear nut 617 causes the externally-threaded rod 90, which does not rotate about its axis, to move in a downward direction, e.g., such that the stopper 90c at the upper end 90b of the externally threaded rod 90 moves away from the surface 8010 of the second jaw 80. Since the externally threaded rod 90 is coupled at its lower end 90a by a pin 92 to the first jaw 50, the first jaw 50 is thereby caused to separate from the second jaw 80. Continuous operation of the first motor 96 in this manner eventually places the surgical device 11 in a fully open position, e.g., whereby the externally-threaded rod 90 is in a fully extended position relative to the second jaw 80 and whereby the second end 707b of the stop member 707 is biased by the spring 705 so as to contact the cylindrical housing wall 708. In this fully open position, a space is provided between the first jaw 50 and the second jaw 80, as illustrated in FIG. 3(a).

A section of the tissue is then placed between the first jaw 50 and the second jaw 80. Thereafter, the first motor 96 is operated in reverse such that the first drive shaft 94 engages the first drive socket 654 in order to cause the clamp shaft assembly 650 to turn in a second, e.g., counter-clockwise, rotation direction. The rotation of the clamp shaft assembly 650 causes the gear cluster 640 to rotate in a second direction, e.g., clockwise, which in turn causes the gear cluster 630 to rotate in a second direction, e.g., counter-clockwise. This rotation of the gear cluster 630 causes the gear cluster 625 to rotate in a second direction, e.g., clockwise, which in turn causes the bevel gear 621 to rotate in a second direction, e.g., clockwise. This rotation of the bevel gear 621 causes the bevel gear nut 617 to rotate within the bevel bearing 622 in a second; e.g., counter-clockwise when viewed from the top, direction, thereby causing the externally-threaded rod 90 to move in an upward direction and causing the first jaw 50 to move toward the second jaw 80. As the externally-threaded rod 90 is gradually retracted to a fully retracted position, e.g., the point at which the stopper 90c of the externally threaded rod 90 contacts the top surface of the second jaw 80, the surgical device 11 is gradually moved first into the partially closed position illustrated in FIG. 3(b), then into the partially closed position illustrated in FIG. 3(c), and eventually into the fully closed position illustrated in FIG. 3(d). Thus, continuous operation of the first motor 96 in this manner eventually places the surgical device 11 in the closed position, e.g., the position illustrated in FIG. 3(d).

Next, the operator determines that it is safe and/or appropriate to begin the cutting and stapling procedure. To begin the stapling and cutting procedure, the second motor 100 of the electro-mechanical driver component 1610 corresponding to the second drive shaft 102 is activated, which engages the second drive socket 694 at a proximal end of the fire shaft assembly 690, thereby causing the fire shaft assembly 690 to turn in a first, e.g., clockwise, rotation direction. Since the spur gear teeth 6911 of the spur gear 691 of the fire shaft assembly 690 are engaged with the spur gear teeth 6811 of the spur gear 681 of the counter shaft assembly 680, this rotation of the first shaft assembly 690 causes rotation of the counter shaft assembly 680 in a direction that is opposite, e.g., counter-clockwise, to the direction of rotation of the fire shaft assembly 690. Since the female, hexagonally-shaped coupling 682 of the counter shaft assembly 680 is non-rotatably coupled to the male, hexagonally-shaped coupling 671 of the counter shaft assembly 670, rotation of the counter shaft assembly 680 in this direction, e.g., counter-clockwise, causes the counter shaft assembly 670 to rotate in the same direction, e.g., counter-clockwise, as the counter shaft assembly 680. Since the spur gear teeth 6721 of the spur gear 672 of the counter shaft assembly 670 are engaged with the spur gear teeth 6621 of the spur gear 662 of the shuttle idler gear 660, this rotation of the counter shaft assembly 670 causes rotation of the shuttle idler gear 660 in a direction that is opposite, e.g., clockwise, to the direction of rotation of the counter shaft assembly 670. Furthermore, since the spur gear teeth 6621 of the spur gear 662 of the shuttle idler gear 660 are engaged with the spur gear teeth 6051 of the spur gear 605d at the proximal end of the wedge driver 605 of the replaceable staple cartridge 600, this rotation of the shuttle idler gear 660 causes rotation of the wedge driver 605 in a direction that is opposite, e.g., counter-clockwise, to the direction of rotation of the shuttle idler gear 660. Preferably, and as illustrated in the example embodiment discussed herein, when the replaceable staple cartridge 600 is initially inserted in the second jaw 80 of the surgical device 11, the wedge 603 and the blade 51 associated therewith are positioned at the distal end 604c of the staple tray 604. Since the threads of the internally threaded bore 603a of the wedge 603 are engaged with the threads of the externally threaded region 605b of the wedge driver 605, this rotation of the wedge driver 605 causes the wedge 603 to move from the distal end 604c toward the proximal end 604d of the staple tray 604 through the central channel 604e of the staple tray 604. Continuous operation of the second motor 100 in this manner will move the wedge 603 fully through the central channel 604e. As previously discussed in connection with FIG. 6(b), the blade 51 is initially positioned such that the cutting edge 51a is in a retracted position. As the wedge 603 moves proximally through the central channel 604e, the contact face 653 of the blade 51 contacts the actuating lip 615a of the housing 615, which causes the blade 51 to rotate relative to the wedge 603. Eventually the blade 51 is rotated relative to the wedge 603 such that the cutting edge 51a of the blade 51 is in an extended position, e.g., the cutting edge 51a faces the proximal end 604d of the staple tray 604. The blade 51 is maintained in this position until the wedge 603 has been moved to the proximal end 604d of the staple tray 604, the blade 51 having thereby cut through the section of tissue. As the wedge 603 is being moved towards the proximal end 604b of the staple tray 604, the sloped edges 603b of the wedge 603 engage, e.g., push down on, the respective top surfaces 607a of the staple pushers 607, thereby causing the staple pushing fingers 607c of the staple pushers 607 to push the staples 606, which are initially disposed within the respective slots 604h of the staple tray 604, out of the slots 604h. The prongs 606b of the staples 606 are pushed through the clamped section of tissue and against the staple guides 703 of the anvil member 700, which bend and close the staples 606, thereby stapling the section of tissue. When the wedge 603 is moved proximally fully through the central channel 604e of the staple tray 604, all of the staples 606 are pushed through the staple tray 604 and are thus closed.

Having cut and stapled the section of tissue, the surgical device 11 may be removed from the patient's body, again through a cannula. According to one embodiment of the present invention, the wedge 603 and the blade 51 may then be returned to their original position at the distal end 604c of the staple tray 604. Alternatively, the staple cartridge 600 is removed from the second jaw 80 without first retracting the wedge 603 and the blade 51, in order that a new staple cartridge 600 be loaded into the second jaw or that the surgical device 11 may be separated from the flexible drive shaft 1620 to be replaced by a new surgical device 11, as desired. In the former described embodiment, e.g., whereby the wedge 603 and the blade 51 are returned to their original position at the distal end 604c of the staple tray 604, the second motor 100 of the electro-mechanical driver component 1610 is engaged in reverse such that the second drive shaft 102, via the second drive socket 694, causes the fire shaft assembly 690 to turn in a second, e.g., counter-clockwise, rotation direction. This rotation of the first shaft assembly 690 causes rotation of the counter shaft assembly 680 in a second direction, e.g., clockwise, which in turn causes the counter shaft assembly 670 to rotate in the same direction, e.g., clockwise. This rotation of the counter shaft assembly 670 causes rotation of the shuttle idler gear 660 in a second direction, e.g., counter-clockwise, which in turn causes rotation of the wedge driver 605 in a second direction, e.g., clockwise. This rotation of the wedge driver 605 causes the wedge 603 to move from the proximal end 604d toward the distal end 604c of the staple tray 604 through the central channel 604e of the staple tray 604. Continuous operation of the second motor 100 in this manner will move the wedge 603 fully through the central channel 604e and back to the distal end 604c of the staple tray 604.

When the surgical device 11 is removed from the patient's body, the first driver 88 may again be engaged, according to some example embodiments of the present invention, to drive the first jaw 50 of the surgical device 11 into the open position relative to the second jaw 80, enabling the spent replaceable staple cartridge 600 to be removed from the second jaw 80 of the surgical device 11 and a new replaceable staple cartridge 600 to be inserted into the second jaw 80. These steps, e.g., inserting the surgical device 11 into the body of the patient, opening the first and second jaws, clamping the first and second jaws onto a section of tissue, cutting and stapling the section of tissue, returning the wedge and the blade to their initial positions and removing the surgical device 11 from the patient's body, are then repeated on the other side of the cancerous tissue, thereby transecting the cancerous section of tissue, which is stapled on both ends to prevent spilling of bowel material into the abdomen.

The reloadability of the surgical device 11, as described above, permits the operator to perform useful steps during the operation of the surgical device 11. For example, once the surgical device 11 is initially placed in the open position, the staple cartridge 600 may be accessed by the operator and may be inspected to determine whether the staples 606 are ready for the procedure and/or whether the need exists to replace the staple cartridge 600 with a more suitable staple cartridge 600. Similarly, once a clamping, cutting and stapling operation has been performed and the set of staples 606 has been used, the staple cartridge 600 may be accessed by the operator again in order to replace the staple cartridge 600 with another staple cartridge 600 or to insert another set of staples 606 into the same staple cartridge 600. Advantageously, the replaceable staple cartridge 600 is removable when the upper jaw 80 and the lower jaw 50 are in the open position, so as to prevent the staple cartridge 600 from being inadvertently removed when the upper jaw 80 and the lower jaw 50 are clamped onto a section of tissue to be cut and stapled.

According to an alternative embodiment of the present invention, the surgical device 11 is non-reloadable, e.g., the staple cartridge 600 is not removable from the second jaw 80 by an operator. Thus, after the surgical device 11 has been actuated once to staple a section of tissue using the staples 606 in the staple cartridge 600, the surgical device 11 cannot be actuated again to staple another section of tissue using a new set of staples 606 or a new staple cartridge 600. By configuring the surgical device 11 so as to be non-reloadable, the risk of contamination or infection is reduced, since the surgical device 11 may not be intentionally or unintentionally used on two different patients and may not be re-used on a single patient. Once a first surgical device 11 has been used, the first surgical device 11 may be separated from the electro-mechanical driver component 1610 and replaced with a second surgical device 11 so that the same clamping, cutting and stapling procedure may be performed on a different section of the tissue, e.g., on the opposite side of the anomalous or cancerous tissue. Once the second end of the bowel is also clamped, cut and stapled, the second surgical device 11 may be separated from the electro-mechanical driver component 1610, and the operator may discard the devices. In an alternative example embodiment, the staple cartridge 600 is configured such that, when a first set of staples 606 in the staple cartridge 600 has been used, the operator may replace the staples 606 in the same staple cartridge 600 and reuse the same staple cartridge 600.

In accordance with still another example embodiment of the present invention, the surgical device 11 may provide limited reloadability, whereby, for example, the surgical device 11 is configured to permit the staple cartridge 600 to be replaced once, so that the clamping, cutting and stapling operation may be performed twice on a single patient, e.g., on opposite sides of a cancerous section of tissue, but does not permit the staple cartridge 600 to be replaced more than twice. In still another example embodiment of the present invention, the surgical device 11 is configured to maintain within the staple cartridge 600 two sets of staples 606, a first set of which is used on one side of a cancerous section of tissue and a second set of which is used on the other side of the cancerous section of tissue. It should be understood that the surgical device 11 may be configured for any predetermined number of uses and that usage may be determined in accordance with the usage data 1184.

According to an alternative example embodiments of the present invention, the surgical device 11 may be configured to provide more than one range of operation. This feature may provide the advantage that sections of tissue having different thicknesses may be more appropriately accommodated by the surgical device 11. For example, according to one example embodiment of the invention, the surgical device 11 may be configured to vary the distance between the first jaw 50 and the second jaw 80 when the surgical device 11 is in the closed position, or to vary the distance that the wedge 603 is moved in the second jaw 80 in order for the wedge 603 to reach a fully extended position. According to one example embodiment, the surgical device 11 may be reloadable so as to use two or more different sizes of staple cartridge, e.g., staple cartridges that have different thicknesses or that house staples 606 having different lengths. In this embodiment, an operator may select to employ one of two or more different staple cartridges 600 having different size staples 606 disposed therein. Accordingly, the memory module 6401 may include data that is readable by the controller 1122 in order that the controller 1122 may recognize the staple cartridge 600 as being of a particular size. The controller 1122 may then vary the number of turns of the first drive shaft 94 during operation so that the distance between the first jaw 50 and the second jaw 80 when the surgical device 11 is moved into the closed position corresponds to the thickness of the tissue to be cut and stapled. Similarly, the controller 1122 may then vary the number of turns of the second drive shaft 102 during operation so that the position of the wedge 603 and the blade 51 when moved into the extended position corresponds to the thickness of the tissue to be cut and stapled. In accordance with another example embodiment of the invention, different sizes of a non-reloadable surgical device 11 may be used, wherein each size of the non-reloadable surgical device 11 corresponds to a different thickness of tissue to be cut and stapled. In this embodiment, the memory module 6401 of the surgical device 11 may include data readable by the controller 1122 in order that the controller 1122 may recognize the surgical device 11 as corresponding to a particular thickness of tissue to be cut and stapled. In still another example embodiment of the invention, the controller 1122 is configured to provide more than one range of operation by enabling an operator to select settings that correspond to different thicknesses of tissue to be cut or stapled. For example, according to one example embodiment, the controller 1122 is configured to actuate the first drive shaft 94 to close first jaw 50 to a first position relative to the second jaw 80 in order to clamp a section of tissue disposed therebetween. The operator may then select whether to actuate the second drive shaft 102 in order to cut and staple the tissue, or whether to actuate the first drive shaft 94 again in order to close the first jaw 50 to a second position relative to the second jaw 80. This embodiment may provide the advantage that an operator is not required to pre-select a particular size of the surgical device 11, or to pre-select a replaceable cartridge for the surgical device 11, before the section of tissue to be cut and stapled has been exposed and its thickness determined. This may prevent an operator from pre-selecting a wrong size or from needing to keep an inventory of more than one size available for use.

As previously mentioned, one problem of conventional cutting and stapling devices is that the opposing jaws of the mechanism do not adequately prevent a section of tissue clamped therebetween from escaping out from between the distal ends of the jaws during the operation of the device. This follows because the scissor-type gripping elements of conventional clamping, cutting and stapling devices, such as the device illustrated in FIG. 1, pivot relative to each other around a fixed pivot point at a proximal end of the gripping elements. Thus, since the distance between the gripping elements is always less at a proximal end of the gripping elements than at the distal ends of the gripping elements, the clamping force on a section of tissue disposed between the gripping elements is greatest near the proximal ends of the gripping elements and gradually decreases in the distal direction. The relatively high clamping force at the proximal ends of the gripping elements coupled with the relatively low clamping force at the distal ends of the gripping elements causes the section of tissue to be pushed towards, and eventually out from between, the distal ends of the gripping elements. Thus, the section of tissue may not be adequately cut and stapled, and the inadequately cut and stapled end of the tissue may permit its contents to spill into the open abdomen of the patient, increasing the likelihood of infection and other complications.

In contrast, and as previously described in detail in connection with FIGS. 3(a) to 3(d), the surgical device 11 of the present invention, in accordance with various embodiments thereof, may provide a biasing element that biases the distal ends 50a, 80a of the first and second jaws 50, 80 towards each other during the operation of the surgical device 11. Specifically, according to one example embodiment of the present invention, the surgical device 11 provides a spring 82 at the proximal ends of the surgical device 11 that biases the distal ends 50a, 80a of the first and second jaws 50, 80 towards each other during the operation of the surgical device 11. Thus, the clamping force between the distal ends 50a, 80a of the first and second jaws 50, 80 is greater in the surgical device 11 than the clamping force between the distal ends of the jaws of a conventional clamping, cutting and stapling device. The increased clamping force at the distal ends 50a, 80a of the first and second jaws 50, 80 may prevent a section of tissue which is disposed between the first and second jaws 50, 80 from escaping out from between the distal ends 50a, 80a of the first and second jaws 50, 80.

Thus, the several aforementioned objects and advantages of the present invention are most effectively attained. Those skilled in the art will appreciate that numerous modifications of the exemplary embodiment described hereinabove may be made without departing from the spirit and scope of the invention. Although a single exemplary embodiment of the present invention has been described and disclosed in detail herein, it should be understood that this invention is in no sense limited thereby.

What is claimed is:

1. A surgical device, comprising:
a first jaw having a distal end;
a second jaw having a distal end, wherein the second jaw is disposed in opposed correspondence with the first jaw, and wherein the first jaw is pivotably coupled to the second jaw;
at least one of a cutting element and a stapling element disposed within the second jaw;
a driver configured to move at least one of the cutting element and the stapling element proximally from the distal end toward a proximal end of the second jaw to at least one of cut and staple a section of tissue disposed between the first and second jaws; and
a biasing element that biases the distal end of the first jaw towards the distal end of the second jaw; and
a stopping element that limits a distance that a proximal end of the first jaw may be separated from a proximal end of the second jaw by the biasing element;
wherein the first jaw is pivotable relative to the second jaw around the stopping element;
wherein, when closing the jaws, the first jaw is initially pivotable relative to the second jaw around the stopping element and eventually pivotable relative to the second jaw around a point other than the stopping element; and
wherein the point other than the stopping element around which the first jaw is eventually pivotable relative to the second jaw is a point at which the distal end of the first jaw contacts the distal end of the second jaw.

2. The device according to claim 1, wherein the biasing element is a spring.

3. The device according to claim 1, wherein the first jaw and the second jaw have proximal ends, and the biasing element is a spring located between the proximal end of the first jaw and the proximal end of the second jaw.

4. The device according to claim 1, wherein the biasing element causes the distal end of the first jaw to contact the distal end of the second jaw prior to the driver completing the closing of the jaws.

5. The device according to claim 1, wherein the point other than the stopping element around which the first jaw is eventually pivotable relative to the second jaw around is a section of tissue disposed between the first jaw and the second jaw.

6. The device according to claim 1, wherein the first jaw has a first length and the second jaw has a second length, where the second length is greater than the first length.

7. An electro-mechanical surgical system, comprising:
an elongated shaft;
a first axially rotatable drive shaft disposed within the elongated shaft;
a surgical device configured to detachably couple to a distal end of the elongated shaft, wherein the surgical device includes:
a first jaw having a distal end;
a second jaw having a distal end, wherein the second jaw is disposed in opposed correspondence with the first jaw, and wherein the first jaw is pivotably coupled to the second jaw;
at least one of a cutting element and a stapling element disposed within the second jaw;
a first driver configured to move at least one of the cutting element and the stapling element proximally from the distal end toward a proximal end of the second jaw to at least one of cut and staple a section of tissue disposed between the first and second jaws;
a biasing element that biases the distal end of the first jaw towards the distal end of the second jaw; and
a motor system configured to drive the first drive shaft;
wherein the surgical device further comprises a stopping element that limits a distance that a proximal end of the first jaw may be separated from a proximal end of the second jaw by the biasing element;
wherein the first jaw is pivotable relative to the second jaw around the stopping element;
wherein, when closing the jaws, the first jaw is initially pivotable relative to the second jaw around the stopping element and eventually pivotable relative to the second jaw around a point other than the stopping element; and
wherein the point other than the stopping element around which the first jaw is eventually pivotable relative to the second jaw is a point at which the distal end of the first jaw contacts the distal end of the second jaw.

8. The electro-mechanical surgical system according to claim 7, wherein the biasing element causes the distal end of the first jaw to contact the distal end of the second jaw prior to the first driver completing the closing of the jaws.

9. The electro-mechanical surgical system according to claim 7, wherein the point other than the stopping element around which the first jaw is eventually pivotable relative to the second jaw around is a section of tissue disposed between the first jaw and the second jaw.

10. The electro-mechanical surgical system according to claim 7, wherein the first jaw has a first length and the second jaw has a second length, where the second length is greater than the first length.

11. The electro-mechanical surgical system according to claim 7, further including a housing, wherein a proximal end of the elongated shaft extends from the housing.

12. The electro-mechanical surgical system according to claim 11, further including a control system configured to control the motor system.

13. The electro-mechanical surgical system according to claim 12, wherein the control system is disposed within the housing.

14. The electro-mechanical surgical system according to claim 12, further including a remote control unit configured to communicate with the control system to control the motor system via the control system.

15. The electro-mechanical surgical system according to claim 14, wherein the remote control unit includes at least one of a wired remote control unit and a wireless remote control unit.

16. The electro-mechanical surgical system according to claim 12, further including a sensor corresponding to the first drive shaft, the sensor outputting a signal in response to and corresponding to a rotation of the first drive shaft.

17. The electro-mechanical surgical system according to claim 16, wherein the control system is configured to determine, based on the output signal of the sensor, at least one of a rotational position and a direction of rotation of the first drive shaft.

18. The electro-mechanical surgical system according to claim 12, wherein the control system includes a first memory unit.

19. The electro-mechanical surgical system according to claim 18, wherein the first memory unit is configured to store a plurality of operating programs, at least one of the operating programs corresponding to operating parameters for the surgical device attached to the distal end of the elongated shaft.

20. The electro-mechanical surgical system according to claim 19, wherein the control system is configured to identify the surgical device attached to a distal end of the elongated shaft as at least one of the cutting element and the stapling element, wherein the at least one of the cutting element and the stapling element is one of a plurality of types of surgical devices attachable to the distal end of the elongated shaft, the control system being configured to at least one of read and select the operating program from the first memory unit corresponding to the at least one of the cutting element and the stapling element.

21. The electro-mechanical surgical system according to claim 18, wherein the control system is configured to identify the surgical device that is attached to the elongated shaft via a data read from a second memory unit disposed within the surgical device.

22. The electro-mechanical surgical system according to claim 21, further including a data cable disposed within the elongated shaft, the data cable being logically and electrically coupled to the control system and being logically and electrically coupleable to the second memory unit.

* * * * *